US010271866B2

(12) United States Patent
Clark, III et al.

(10) Patent No.: US 10,271,866 B2
(45) Date of Patent: *Apr. 30, 2019

(54) MODULAR SYSTEMS FOR TREATING TISSUE

(71) Applicant: Ulthera, Inc., Mesa, AZ (US)

(72) Inventors: Robert L. Clark, III, Hayward, CA (US); James E. Chomas, Boulder, CO (US); Adnan I. Merchant, Fremont, CA (US); Ben F. Brian, III, Menlo Park, CA (US)

(73) Assignee: ULTHERA, INC., Mesa, AZ (US)

( * ) Notice: Subject to any disclaimer, the term of this patent is extended or adjusted under 35 U.S.C. 154(b) by 341 days.

This patent is subject to a terminal disclaimer.

(21) Appl. No.: 15/339,585

(22) Filed: Oct. 31, 2016

(65) Prior Publication Data
US 2017/0042608 A1  Feb. 16, 2017

Related U.S. Application Data

(63) Continuation of application No. 14/296,353, filed on Jun. 4, 2014, now Pat. No. 9,510,849, which is a (Continued)

(51) Int. Cl.
*A61B 17/32* (2006.01)
*A61B 17/34* (2006.01)
(Continued)

(52) U.S. Cl.
CPC ............ *A61B 17/32002* (2013.01); *A61B 17/320016* (2013.01); *A61B 17/32093* (2013.01);
(Continued)

(58) Field of Classification Search
CPC ..... A61B 17/00; A61B 17/32; A61B 17/3202; A61B 17/320016; A61B 17/32016;
(Continued)

(56) References Cited

U.S. PATENT DOCUMENTS 2,370,529 A    2/1945   Fuller
2,490,409 A    12/1949  Brown
(Continued)

FOREIGN PATENT DOCUMENTS

CA    1232837    2/1988
CA    1239092    7/1988
(Continued)

OTHER PUBLICATIONS

U.S. Appl. No. 11/292,950 (U.S. Pat. No. 7,967,763), filed Dec. 2, 2005 (Jun. 28, 2011), Method for Treating Subcutaneous Tissues.
(Continued)

*Primary Examiner* — David C Eastwood
(74) *Attorney, Agent, or Firm* — Knobbe, Martens, Olson & Bear LLP

(57) ABSTRACT

Devices and methods for performing subcutaneous surgery in a minimally invasive manner are provided. The methods include application of reduced air pressure in a recessed area of a handpiece placed over a section of skin and drawing the section of skin and subcutaneous tissue into the recessed area. In a subsequent step a tool is inserted through a tool conduit in the handpiece and through the skin into the subcutaneous tissue, enabling the performance of the desired surgery. Common surgical procedures include dissection and ablation. The devices and methods can be directed at the treatment of skin conditions like atrophic scars, wrinkles, or other cosmetic issues, at treatments like or promoting wound healing or preventing hyperhidrosis, or can be used for creating space for various implants.

20 Claims, 45 Drawing Sheets

Related U.S. Application Data continuation of application No. 14/060,437, filed on Oct. 22, 2013, now Pat. No. 9,358,064, which is a continuation-in-part of application No. 13/712,429, filed on Dec. 12, 2012, now Pat. No. 9,011,473, which is a continuation of application No. 12/787,382, filed on May 25, 2010, now Pat. No. 8,518,069.

(60) Provisional application No. 61/232,385, filed on Aug. 7, 2009, provisional application No. 61/286,750, filed on Dec. 15, 2009.

(51) Int. Cl.

| | | |
|---|---|---|
| *A61B 17/3209* | (2006.01) | |
| *A61B 18/14* | (2006.01) | |
| *A61M 37/00* | (2006.01) | |
| *A61B 18/18* | (2006.01) | |
| *A61B 90/00* | (2016.01) | |
| *A61B 17/3201* | (2006.01) | |
| *A61B 18/06* | (2006.01) | |
| *A61B 18/00* | (2006.01) | |
| *A61N 7/02* | (2006.01) | |
| *A61F 2/00* | (2006.01) | |
| *A61B 18/20* | (2006.01) | |
| *A61B 17/00* | (2006.01) | |
| *A61B 17/30* | (2006.01) | |
| *A61N 7/00* | (2006.01) | |
| *A61B 18/08* | (2006.01) | |

(52) U.S. Cl.
CPC .......... *A61B 17/3403* (2013.01); *A61B 18/14* (2013.01); *A61B 18/1477* (2013.01); *A61B 18/18* (2013.01); *A61B 90/02* (2016.02); *A61M 37/00* (2013.01); *A61B 17/3201* (2013.01); *A61B 18/06* (2013.01); *A61B 18/082* (2013.01); *A61B 18/1402* (2013.01); *A61B 18/1815* (2013.01); *A61B 18/20* (2013.01); *A61B 2017/00119* (2013.01); *A61B 2017/00761* (2013.01); *A61B 2017/308* (2013.01); *A61B 2017/32006* (2013.01); *A61B 2017/320028* (2013.01); *A61B 2017/320052* (2013.01); *A61B 2017/320056* (2013.01); *A61B 2017/3405* (2013.01); *A61B 2017/3407* (2013.01); *A61B 2017/3409* (2013.01); *A61B 2018/0016* (2013.01); *A61B 2018/0047* (2013.01); *A61B 2018/00291* (2013.01); *A61B 2018/00434* (2013.01); *A61B 2018/00452* (2013.01); *A61B 2018/00458* (2013.01); *A61B 2018/00571* (2013.01); *A61B 2018/00577* (2013.01); *A61B 2018/00601* (2013.01); *A61B 2018/00607* (2013.01); *A61B 2018/00648* (2013.01); *A61B 2018/00702* (2013.01); *A61B 2018/00791* (2013.01); *A61B 2018/00875* (2013.01); *A61B 2018/143* (2013.01); *A61B 2018/1415* (2013.01); *A61B 2018/1425* (2013.01); *A61B 2018/1432* (2013.01); *A61B 2090/0811* (2016.02); *A61B 2090/0815* (2016.02); *A61B 2218/002* (2013.01); *A61F 2/0059* (2013.01); *A61F 2/0063* (2013.01); *A61N 7/02* (2013.01); *A61N 2007/0008* (2013.01)

(58) Field of Classification Search
CPC .... A61B 17/32093; A61B 2017/32004; A61B 2017/320052; A61B 18/14; A61B 18/18; A61B 18/20; A61B 18/1477; A61B 19/24; A61N 1/306; A61N 1/327; A61N 1/328; A61N 1/403; A61M 37/00
See application file for complete search history.

(56) References Cited

U.S. PATENT DOCUMENTS

| | | |
|---|---|---|
| 2,738,172 A | 3/1956 | Spiess et al. |
| 2,945,496 A | 7/1960 | Fosdal |
| 2,961,382 A | 11/1960 | Singher et al. |
| 3,129,944 A | 4/1964 | Amos et al. |
| 3,324,854 A | 6/1967 | Weese |
| 3,590,808 A | 7/1971 | Muller |
| 3,735,336 A | 5/1973 | Long |
| 3,964,482 A | 6/1976 | Gerstel et al. |
| 3,991,763 A | 11/1976 | Genese |
| 4,150,669 A | 4/1979 | Latorre |
| 4,188,952 A | 2/1980 | Loschilov et al. |
| 4,211,949 A | 7/1980 | Brisken et al. |
| 4,212,206 A | 7/1980 | Hartemann et al. |
| 4,231,368 A | 11/1980 | Becker et al. |
| 4,248,231 A | 2/1981 | Herczog et al. |
| 4,249,923 A | 2/1981 | Walda |
| 4,276,885 A | 7/1981 | Tickner et al. |
| 4,299,219 A | 11/1981 | Norris, Jr. |
| 4,309,989 A | 1/1982 | Fahim |
| 4,373,458 A | 2/1983 | Dorosz et al. |
| 4,382,441 A | 5/1983 | Svedman |
| 4,466,442 A | 8/1984 | Hilmann et al. |
| 4,497,325 A | 2/1985 | Wedel |
| 4,536,180 A | 8/1985 | Johnson |
| 4,549,533 A | 10/1985 | Cain |
| 4,608,043 A | 8/1986 | Larkin |
| 4,641,652 A | 2/1987 | Hutterer et al. |
| 4,646,754 A | 3/1987 | Seale |
| 4,657,756 A | 4/1987 | Rasor et al. |
| 4,673,387 A | 6/1987 | Phillips et al. |
| 4,681,119 A | 7/1987 | Rasor et al. |
| 4,684,479 A | 8/1987 | D'Arrigo |
| 4,688,570 A | 8/1987 | Kramer et al. |
| 4,689,986 A | 9/1987 | Carson et al. |
| 4,718,433 A | 1/1988 | Feinstein |
| 4,720,075 A | 1/1988 | Peterson et al. |
| 4,751,921 A | 6/1988 | Park |
| 4,762,915 A | 8/1988 | Kung et al. |
| 4,774,958 A | 10/1988 | Feinstein |
| 4,796,624 A | 1/1989 | Trott et al. |
| 4,797,285 A | 1/1989 | Barenholz et al. |
| 4,815,462 A | 3/1989 | Clark |
| 4,844,080 A | 7/1989 | Frass et al. |
| 4,844,470 A | 7/1989 | Hammon et al. |
| 4,844,882 A | 7/1989 | Widder et al. |
| 4,886,491 A | 12/1989 | Parisi et al. |
| 4,900,540 A | 2/1990 | Ryan et al. |
| 4,919,986 A | 4/1990 | Lay et al. |
| 4,920,954 A | 5/1990 | Alliger et al. |
| 4,936,281 A | 6/1990 | Stasz |
| 4,936,303 A | 6/1990 | Detwiler et al. |
| 4,957,656 A | 9/1990 | Cerny et al. |
| 5,022,414 A | 6/1991 | Muller |
| 5,040,537 A | 8/1991 | Katakura |
| 5,050,537 A | 9/1991 | Fox |
| 5,069,664 A | 12/1991 | Guess et al. |
| 5,083,568 A | 1/1992 | Shimazaki et al. |
| 5,088,499 A | 2/1992 | Unger |
| 5,100,390 A | 3/1992 | Lubeck et al. |
| 5,131,600 A | 7/1992 | Klimpel |
| 5,143,063 A | 9/1992 | Fellner |
| 5,149,319 A | 9/1992 | Unger |
| 5,158,071 A | 10/1992 | Umemura et al. |
| 5,170,604 A | 12/1992 | Hedly |
| 5,178,433 A | 1/1993 | Wagner |
| 5,203,785 A | 4/1993 | Slater |
| 5,209,720 A | 5/1993 | Unger |
| 5,215,104 A | 6/1993 | Steinert |
| 5,215,680 A | 6/1993 | D'Arrigo |
| 5,216,130 A | 6/1993 | Line et al. |

(56) References Cited

U.S. PATENT DOCUMENTS

| | | |
|---|---|---|
| 5,219,401 A | 6/1993 | Cathignol et al. |
| 5,261,922 A | 11/1993 | Hood |
| 5,308,334 A | 5/1994 | Sancoff |
| 5,310,540 A | 5/1994 | Giddey et al. |
| 5,312,364 A | 5/1994 | Jacobs |
| 5,315,998 A | 5/1994 | Tachibana et al. |
| 5,316,000 A | 5/1994 | Chapelon et al. |
| 5,320,607 A | 6/1994 | Ishibashi |
| 5,342,380 A | 8/1994 | Hood |
| 5,352,436 A | 10/1994 | Wheatley et al. |
| 5,354,307 A | 10/1994 | Porowski |
| 5,380,411 A | 1/1995 | Schlief |
| 5,383,858 A | 1/1995 | Reilly et al. |
| 5,385,561 A | 1/1995 | Cerny |
| 5,409,126 A | 4/1995 | DeMars |
| 5,413,574 A | 5/1995 | Fugo |
| 5,415,160 A | 5/1995 | Ortiz et al. |
| 5,417,654 A | 5/1995 | Kelman |
| 5,419,761 A | 5/1995 | Narayanan et al. |
| 5,419,777 A | 5/1995 | Hofling et al. |
| 5,425,580 A | 6/1995 | Beller |
| 5,437,640 A | 8/1995 | Schwab |
| 5,441,490 A | 8/1995 | Svedman |
| 5,449,351 A | 9/1995 | Zohmann |
| 5,457,041 A | 10/1995 | Ginaven et al. |
| 5,476,368 A | 12/1995 | Rabenau et al. |
| 5,478,315 A | 12/1995 | Brothers |
| 5,494,038 A | 2/1996 | Wang et al. |
| 5,507,790 A | 4/1996 | Weiss |
| 5,522,797 A | 6/1996 | Grimm |
| 5,533,981 A | 7/1996 | Mandro et al. |
| 5,545,123 A | 8/1996 | Ortiz et al. |
| 5,556,406 A | 9/1996 | Gordon et al. |
| 5,562,693 A | 10/1996 | Devlin et al. |
| 5,569,242 A | 10/1996 | Lax et al. |
| 5,571,131 A | 11/1996 | Ek et al. |
| 5,573,002 A | 11/1996 | Pratt |
| 5,573,497 A | 11/1996 | Chapelon |
| 5,590,657 A | 1/1997 | Cain |
| 5,601,526 A | 2/1997 | Chapelon |
| 5,601,584 A | 2/1997 | Obaji et al. |
| 5,607,441 A | 3/1997 | Sierocuk et al. |
| 5,639,443 A | 6/1997 | Schutt et al. |
| 5,649,947 A | 7/1997 | Auerbach et al. |
| 5,662,646 A | 9/1997 | Fumich |
| 5,681,026 A | 10/1997 | Durand |
| 5,690,657 A | 11/1997 | Koepnick |
| 5,695,460 A | 12/1997 | Siegel et al. |
| 5,716,326 A | 2/1998 | Dannan |
| 5,733,572 A | 3/1998 | Unger et al. |
| 5,755,753 A | 5/1998 | Knowlton |
| 5,766,198 A | 6/1998 | Li |
| 5,772,688 A | 6/1998 | Muroki |
| 5,778,894 A | 7/1998 | Dorogi et al. |
| 5,792,140 A | 8/1998 | Tu |
| 5,795,311 A | 8/1998 | Wess |
| 5,797,627 A | 8/1998 | Salter et al. |
| 5,810,765 A | 9/1998 | Oda |
| 5,817,054 A | 10/1998 | Grimm |
| 5,817,115 A * | 10/1998 | Nigam ............... A61F 9/013 606/166 |
| 5,827,204 A | 10/1998 | Grandia et al. |
| 5,827,216 A | 10/1998 | Igo et al. |
| 5,865,309 A | 2/1999 | Futagawa et al. |
| 5,871,524 A | 2/1999 | Knowlton |
| 5,884,631 A | 3/1999 | Silberg |
| 5,885,232 A | 3/1999 | Guitay |
| 5,902,272 A | 5/1999 | Eggers et al. |
| 5,911,700 A | 6/1999 | Mozsary et al. |
| 5,911,703 A | 6/1999 | Slate et al. |
| 5,918,757 A | 7/1999 | Przytulla et al. |
| 5,919,219 A | 7/1999 | Knowlton |
| 5,935,142 A | 8/1999 | Hood |
| 5,935,143 A | 8/1999 | Hood |
| 5,942,408 A | 8/1999 | Christensen et al. |
| 5,948,011 A | 9/1999 | Knowlton |
| 5,961,475 A | 10/1999 | Guitay |
| 5,964,776 A | 10/1999 | Peyman |
| 5,976,153 A | 11/1999 | Fishel et al. |
| 5,976,163 A * | 11/1999 | Nigam ............... A61F 9/0133 606/166 |
| 5,980,517 A | 11/1999 | Gough |
| 5,983,131 A | 11/1999 | Weaver et al. |
| 5,984,915 A | 11/1999 | Loeb et al. |
| 5,993,423 A | 11/1999 | Choi |
| 5,997,501 A | 12/1999 | Gross et al. |
| 6,035,897 A | 3/2000 | Kozyuk |
| 6,039,048 A | 3/2000 | Silberg |
| 6,042,539 A | 3/2000 | Harper et al. |
| 6,047,215 A | 4/2000 | McClure et al. |
| 6,048,337 A | 4/2000 | Svedman |
| 6,066,131 A | 5/2000 | Mueller et al. |
| 6,071,239 A | 6/2000 | Cribbs et al. |
| 6,083,236 A | 7/2000 | Feingold |
| 6,102,887 A | 8/2000 | Altman |
| 6,113,558 A | 9/2000 | Rosenschein et al. |
| 6,117,152 A | 9/2000 | Huitema |
| RE36,939 E | 10/2000 | Tachibana et al. |
| 6,128,958 A | 10/2000 | Cain |
| 6,132,755 A | 10/2000 | Eicher et al. |
| 6,139,518 A | 10/2000 | Mozary et al. |
| 6,155,989 A | 12/2000 | Collins |
| 6,162,232 A | 12/2000 | Shadduck |
| 6,176,854 B1 | 1/2001 | Cone |
| 6,183,442 B1 | 2/2001 | Athanasiou et al. |
| 6,193,672 B1 | 2/2001 | Clement |
| 6,200,291 B1 | 3/2001 | Di Pietro |
| 6,200,313 B1 | 3/2001 | Abe et al. |
| 6,203,540 B1 | 3/2001 | Weber |
| 6,230,540 B1 | 3/2001 | Weber |
| 6,210,393 B1 | 4/2001 | Brisken |
| 6,214,018 B1 | 4/2001 | Kreizman et al. |
| 6,237,604 B1 | 5/2001 | Burnside et al. |
| 6,241,753 B1 | 6/2001 | Knowlton |
| 6,254,580 B1 | 7/2001 | Svedman |
| 6,254,614 B1 | 7/2001 | Jesseph |
| 6,258,056 B1 | 7/2001 | Turley et al. |
| 6,258,378 B1 | 7/2001 | Schneider et al. |
| 6,261,272 B1 | 7/2001 | Gross et al. |
| 6,273,877 B1 | 8/2001 | West et al. |
| 6,277,116 B1 | 8/2001 | Utely et al. |
| 6,280,401 B1 | 8/2001 | Mahurkar |
| 6,287,274 B1 | 9/2001 | Sussman et al. |
| 6,302,863 B1 | 10/2001 | Tankovich |
| 6,309,355 B1 | 10/2001 | Cain et al. |
| 6,311,090 B1 | 10/2001 | Knowlton |
| 6,312,439 B1 | 11/2001 | Gordon |
| 6,315,756 B1 | 11/2001 | Tankovich |
| 6,315,777 B1 | 11/2001 | Comben |
| 6,319,230 B1 | 11/2001 | Palasis et al. |
| 6,321,109 B2 | 11/2001 | Ben-Haim et al. |
| 6,325,801 B1 | 12/2001 | Monnier |
| 6,338,710 B1 | 1/2002 | Takahashi et al. |
| 6,350,276 B1 | 2/2002 | Knowlton |
| 6,366,206 B1 | 4/2002 | Ishikawa |
| 6,375,634 B1 | 4/2002 | Carroll |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,391,020 B1 | 5/2002 | Kurtz et al. |
| 6,391,023 B1 | 5/2002 | Weber et al. |
| 6,397,098 B1 | 5/2002 | Uber, III et al. |
| 6,405,090 B1 | 6/2002 | Knowlton |
| 6,409,665 B1 | 6/2002 | Scott et al. |
| 6,413,216 B1 | 7/2002 | Cain et al. |
| 6,413,255 B1 | 7/2002 | Stern |
| 6,425,912 B1 | 7/2002 | Knowlton |
| 6,430,446 B1 | 8/2002 | Knowlton |
| 6,430,466 B1 | 8/2002 | Knowlton |
| 6,432,101 B1 | 8/2002 | Weber et al. |
| 6,436,078 B1 | 8/2002 | Svedman |
| 6,438,424 B1 | 8/2002 | Knowlton |

(56) References Cited

U.S. PATENT DOCUMENTS

| | | |
|---|---|---|
| 6,440,096 B1 | 8/2002 | Lastovich et al. |
| 6,440,121 B1 | 8/2002 | Weber et al. |
| 6,443,914 B1 | 9/2002 | Costantino |
| 6,450,979 B1 | 9/2002 | Miwa |
| 6,451,240 B1 | 9/2002 | Sherman et al. |
| 6,453,202 B1 | 9/2002 | Knowlton |
| 6,454,730 B1 | 9/2002 | Hechel et al. |
| 6,461,350 B1 | 10/2002 | Underwood et al. |
| 6,461,378 B1 | 10/2002 | Knowlton |
| 6,464,680 B1 | 10/2002 | Brisken et al. |
| 6,470,216 B1 | 10/2002 | Knowlton |
| 6,470,218 B1 | 10/2002 | Behl |
| 6,479,034 B1 | 11/2002 | Unger et al. |
| 6,500,141 B1 | 12/2002 | Irion et al. |
| 6,506,611 B2 | 1/2003 | Bienert et al. |
| 6,511,463 B1 | 1/2003 | Wood et al. |
| 6,514,220 B2 | 2/2003 | Melton |
| 6,517,498 B1 | 2/2003 | Burbank et al. |
| 6,537,242 B1 | 3/2003 | Palmer |
| 6,537,246 B1 | 3/2003 | Unger et al. |
| 6,544,201 B1 | 4/2003 | Guitay |
| 6,569,176 B2 | 5/2003 | Jesseph |
| 6,572,839 B2 | 6/2003 | Sugita |
| 6,575,930 B1 | 6/2003 | Trombley, III et al. |
| 6,582,442 B2 | 6/2003 | Simon et al. |
| 6,585,678 B1 | 7/2003 | Tachibana et al. |
| 6,599,305 B1 | 7/2003 | Feingold |
| 6,602,251 B2 | 8/2003 | Burbank et al. |
| 6,605,079 B2 | 8/2003 | Shanks et al. |
| 6,605,080 B1 | 8/2003 | Altshuler et al. |
| 6,607,498 B2 | 8/2003 | Eshel |
| 6,611,707 B1 | 8/2003 | Prausnitz et al. |
| 6,615,166 B1 | 9/2003 | Guheen et al. |
| 6,623,457 B1 | 9/2003 | Rosenberg |
| 6,626,854 B2 | 9/2003 | Friedman et al. |
| 6,629,949 B1 | 10/2003 | Douglas |
| 6,638,767 B2 | 10/2003 | Unger et al. |
| 6,645,162 B2 | 11/2003 | Friedman et al. |
| 6,662,054 B2 | 12/2003 | Kreindel et al. |
| 6,663,616 B1 | 12/2003 | Roth et al. |
| 6,663,618 B2 | 12/2003 | Weber et al. |
| 6,663,820 B2 | 12/2003 | Arias et al. |
| 6,685,657 B2 | 2/2004 | Jones |
| 6,687,537 B2 | 2/2004 | Bernabei |
| 6,695,781 B2 | 2/2004 | Rabiner |
| 6,695,808 B2 | 2/2004 | Tom |
| 6,702,779 B2 | 3/2004 | Connelly et al. |
| 6,725,095 B2 | 4/2004 | Fenn et al. |
| 6,730,061 B1 | 5/2004 | Cuschieri et al. |
| 6,743,211 B1 | 6/2004 | Prausnitz et al. |
| 6,743,214 B2 | 6/2004 | Heil et al. |
| 6,743,215 B2 | 6/2004 | Bernabei |
| 6,749,624 B2 | 6/2004 | Knowlton |
| 6,770,071 B2 | 8/2004 | Woloszko et al. |
| 6,780,171 B2 | 8/2004 | Gabel et al. |
| 6,795,727 B2 | 9/2004 | Giammarusti |
| 6,795,728 B2 | 9/2004 | Chornenky et al. |
| 6,817,988 B2 | 11/2004 | Bergeron et al. |
| 6,826,429 B2 | 11/2004 | Johnson et al. |
| 6,855,133 B2 | 2/2005 | Svedman |
| 6,882,884 B1 | 4/2005 | Mosk et al. |
| 6,883,729 B2 | 4/2005 | Putvinski et al. |
| 6,889,090 B2 | 5/2005 | Kreindel |
| 6,892,099 B2 | 5/2005 | Jaafar et al. |
| 6,896,659 B2 | 5/2005 | Conston et al. |
| 6,896,666 B2 | 5/2005 | Kochamba |
| 6,896,674 B1 | 5/2005 | Woloszko et al. |
| 6,902,554 B2 | 6/2005 | Huttner |
| 6,905,480 B2 | 6/2005 | McGuckin et al. |
| 6,910,671 B1 | 6/2005 | Korkus et al. |
| 6,916,328 B2 | 7/2005 | Brett et al. |
| 6,918,907 B2 | 7/2005 | Kelly et al. |
| 6,918,908 B2 * | 7/2005 | Bonner ............ A61B 18/1485 600/114 |
| 6,920,883 B2 | 7/2005 | Bessette et al. |
| 6,926,683 B1 | 8/2005 | Kochman et al. |
| 6,931,277 B1 | 8/2005 | Yuzhakov et al. |
| 6,945,937 B2 | 9/2005 | Culp et al. |
| 6,957,186 B1 | 10/2005 | Guheen et al. |
| 6,960,205 B2 * | 11/2005 | Jahns ............... A61B 18/1492 606/41 |
| 6,971,994 B1 | 12/2005 | Young |
| 6,974,450 B2 | 12/2005 | Weber |
| 6,994,691 B2 | 2/2006 | Ejlersen |
| 6,994,705 B2 | 2/2006 | Nebis et al. |
| 7,066,922 B2 | 6/2006 | Angel et al. |
| 7,083,580 B2 | 8/2006 | Bernabei |
| 7,115,108 B2 | 10/2006 | Wilkinson et al. |
| 7,149,698 B2 | 12/2006 | Guheen et al. |
| 7,153,306 B2 | 12/2006 | Ralph et al. |
| 7,169,115 B2 | 1/2007 | Nobis et al. |
| 7,184,614 B2 | 2/2007 | Slatkine |
| 7,184,826 B2 | 2/2007 | Cormier et al. |
| 7,186,252 B2 | 3/2007 | Nobis et al. |
| 7,217,265 B2 | 5/2007 | Hennings et al. |
| 7,223,275 B2 | 5/2007 | Shiuey |
| 7,226,446 B1 | 6/2007 | Mody et al. |
| 7,238,183 B2 | 7/2007 | Kreindel |
| 7,250,047 B2 | 7/2007 | Anderson et al. |
| 7,252,641 B2 | 8/2007 | Thompson et al. |
| 7,258,674 B2 | 8/2007 | Cribbs et al. |
| 7,278,991 B2 | 10/2007 | Morris et al. |
| 7,306,095 B1 | 12/2007 | Bourque et al. |
| 7,315,826 B1 | 1/2008 | Guheen et al. |
| 7,331,951 B2 | 2/2008 | Eschel et al. |
| 7,335,158 B2 | 2/2008 | Taylor |
| 7,338,551 B2 | 3/2008 | Kozyuk |
| 7,347,855 B2 | 3/2008 | Eshel et al. |
| 7,351,295 B2 | 4/2008 | Pawlik et al. |
| 7,374,551 B2 | 5/2008 | Liang |
| 7,376,460 B2 | 5/2008 | Bernabei |
| 7,392,080 B2 | 6/2008 | Eppstein et al. |
| 7,410,476 B2 | 8/2008 | Wilkinson et al. |
| 7,419,798 B2 | 9/2008 | Ericson |
| 7,437,189 B2 | 10/2008 | Matsumura et al. |
| 7,442,192 B2 | 10/2008 | Knowlton |
| 7,452,358 B2 | 11/2008 | Stern et al. |
| 7,455,663 B2 | 11/2008 | Bikovsky |
| 7,470,237 B2 | 12/2008 | Beckman et al. |
| 7,473,251 B2 | 1/2009 | Knowlton et al. |
| 7,479,104 B2 | 1/2009 | Lau et al. |
| 7,494,488 B2 | 2/2009 | Weber |
| 7,507,209 B2 | 3/2009 | Nezhat et al. |
| 7,524,318 B2 | 4/2009 | Young et al. |
| 7,546,918 B2 | 6/2009 | Gollier et al. |
| 7,559,905 B2 | 7/2009 | Kagosaki et al. |
| 7,566,318 B2 | 7/2009 | Haefner |
| 7,585,281 B2 | 9/2009 | Nezhat et al. |
| 7,588,547 B2 | 9/2009 | Deem et al. |
| 7,588,557 B2 | 9/2009 | Nakao |
| 7,601,128 B2 | 10/2009 | Deem et al. |
| 7,625,354 B2 | 12/2009 | Hochman |
| 7,625,371 B2 | 12/2009 | Morris et al. |
| 7,678,097 B1 | 3/2010 | Peluso et al. |
| 7,740,600 B2 | 6/2010 | Slatkine et al. |
| 7,762,964 B2 | 7/2010 | Slatkine et al. |
| 7,762,965 B2 | 7/2010 | Slatkine et al. |
| 7,770,611 B2 | 8/2010 | Houwaert et al. |
| 7,771,374 B2 | 8/2010 | Slatkine et al. |
| 7,824,348 B2 | 11/2010 | Barthe et al. |
| 7,828,827 B2 | 11/2010 | Gartstein et al. |
| 7,842,008 B2 | 11/2010 | Clarke et al. |
| 7,901,421 B2 | 3/2011 | Shiuey et al. |
| 7,935,139 B2 | 5/2011 | Slatkine et al. |
| 7,938,824 B2 | 5/2011 | Chornenky et al. |
| 7,967,763 B2 | 6/2011 | Deem et al. |
| 7,985,199 B2 | 7/2011 | Kornerup et al. |
| 8,025,658 B2 | 9/2011 | Chong et al. |
| 8,083,715 B2 | 12/2011 | Sonoda et al. |
| 8,086,322 B2 | 12/2011 | Schouenborg |
| 8,103,355 B2 | 1/2012 | Mulholland et al. |
| 8,127,771 B2 | 3/2012 | Hennings |
| 8,133,191 B2 | 3/2012 | Rosenberg et al. |
| 8,256,429 B2 | 9/2012 | Hennings et al. |

(56) References Cited

U.S. PATENT DOCUMENTS

| | | |
|---|---|---|
| 8,348,867 B2 | 1/2013 | Deem et al. |
| 8,357,146 B2 | 1/2013 | Hennings et al. |
| 8,366,643 B2 | 2/2013 | Deem et al. |
| 8,401,668 B2 | 3/2013 | Deem et al. |
| 8,406,894 B2 | 3/2013 | Johnson et al. |
| 8,439,940 B2 | 5/2013 | Chomas et al. |
| 8,518,069 B2 | 8/2013 | Clark, III et al. |
| 8,535,302 B2 | 9/2013 | Ben-Haim et al. |
| 8,540,705 B2 | 9/2013 | Mehta |
| 8,573,227 B2 | 11/2013 | Hennings et al. |
| 8,608,737 B2 | 12/2013 | Mehta et al. |
| 8,636,665 B2 | 1/2014 | Slayton et al. |
| 8,652,123 B2 | 2/2014 | Gurtner et al. |
| 8,663,112 B2 | 3/2014 | Slayton et al. |
| 8,671,622 B2 | 3/2014 | Thomas |
| 8,672,848 B2 | 3/2014 | Slayton et al. |
| 8,676,338 B2 | 3/2014 | Levinson |
| 8,685,012 B2 | 4/2014 | Hennings et al. |
| 8,753,339 B2 | 6/2014 | Clark, III et al. |
| 8,758,366 B2 | 6/2014 | McLean et al. |
| 8,771,263 B2 | 7/2014 | Epshtein et al. |
| 8,825,176 B2 | 9/2014 | Johnson et al. |
| 8,834,547 B2 | 9/2014 | Anderson et al. |
| 8,868,204 B2 | 10/2014 | Edoute et al. |
| 8,882,753 B2 | 11/2014 | Mehta et al. |
| 8,882,758 B2 | 11/2014 | Nebrigie et al. |
| 8,894,678 B2 | 11/2014 | Clark, III et al. |
| 8,900,261 B2 | 12/2014 | Clark, III et al. |
| 8,900,262 B2 | 12/2014 | Clark, III et al. |
| 8,979,882 B2 | 3/2015 | Drews et al. |
| 9,011,473 B2 * | 4/2015 | Clark, III ......... A61B 17/32093 606/167 |
| 9,039,722 B2 | 5/2015 | Clark, III et al. |
| 9,345,456 B2 | 5/2016 | Tsonton et al. |
| 9,364,246 B2 | 6/2016 | Clark, III et al. |
| 2001/0001829 A1 | 5/2001 | Sugimura et al. |
| 2001/0004702 A1 | 6/2001 | Peyman |
| 2001/0014805 A1 | 8/2001 | Burbank et al. |
| 2001/0053887 A1 | 12/2001 | Douglas et al. |
| 2002/0029053 A1 | 3/2002 | Gordon |
| 2002/0082528 A1 | 6/2002 | Friedman et al. |
| 2002/0082589 A1 | 6/2002 | Friedman et al. |
| 2002/0099356 A1 | 7/2002 | Unger et al. |
| 2002/0111569 A1 | 8/2002 | Rosenschein |
| 2002/0120238 A1 | 8/2002 | McGuckin et al. |
| 2002/0120260 A1 | 8/2002 | Morris et al. |
| 2002/0120261 A1 | 8/2002 | Morris et al. |
| 2002/0130126 A1 | 9/2002 | Rosenberg |
| 2002/0134733 A1 | 9/2002 | Kerfoot |
| 2002/0137991 A1 | 9/2002 | Scarantino |
| 2002/0143326 A1 | 10/2002 | Foley et al. |
| 2002/0169394 A1 | 11/2002 | Eppstein et al. |
| 2002/0177846 A1 | 11/2002 | Muller |
| 2002/0185557 A1 | 12/2002 | Sparks |
| 2002/0193784 A1 | 12/2002 | McHale et al. |
| 2002/0193831 A1 | 12/2002 | Smith, III |
| 2003/0006677 A1 | 1/2003 | Okuda et al. |
| 2003/0009153 A1 | 1/2003 | Brisken et al. |
| 2003/0069502 A1 | 4/2003 | Makin et al. |
| 2003/0074023 A1 | 4/2003 | Kaplan et al. |
| 2003/0083536 A1 | 5/2003 | Eshel et al. |
| 2003/0120269 A1 | 6/2003 | Bessette et al. |
| 2003/0130628 A1 | 7/2003 | Duffy |
| 2003/0130655 A1 | 7/2003 | Woloszko et al. |
| 2003/0130711 A1 | 7/2003 | Pearson et al. |
| 2003/0139740 A1 | 7/2003 | Kreindel |
| 2003/0139755 A1 | 7/2003 | Dybbs |
| 2003/0153905 A1 | 8/2003 | Edwards et al. |
| 2003/0153960 A1 | 8/2003 | Chornenky et al. |
| 2003/0158566 A1 | 8/2003 | Brett |
| 2003/0171670 A1 | 9/2003 | Gumb et al. |
| 2003/0187371 A1 | 10/2003 | Vortman et al. |
| 2003/0212350 A1 | 11/2003 | Tadlock |
| 2003/0228254 A1 | 12/2003 | Klaveness et al. |
| 2003/0233083 A1 | 12/2003 | Houwaert |
| 2003/0233110 A1 | 12/2003 | Jesseph |
| 2004/0006566 A1 | 1/2004 | Taylor et al. |
| 2004/0019299 A1 | 1/2004 | Ritchart et al. |
| 2004/0019371 A1 | 1/2004 | Jaafar et al. |
| 2004/0023844 A1 | 2/2004 | Pettis et al. |
| 2004/0030263 A1 | 2/2004 | Dubrul et al. |
| 2004/0039312 A1 | 2/2004 | Hillstead et al. |
| 2004/0058882 A1 | 3/2004 | Eriksson et al. |
| 2004/0073144 A1 | 4/2004 | Carava |
| 2004/0073206 A1 | 4/2004 | Foley et al. |
| 2004/0079371 A1 | 4/2004 | Gray |
| 2004/0097967 A1 | 5/2004 | Ignon |
| 2004/0106867 A1 | 6/2004 | Eshel et al. |
| 2004/0120861 A1 | 6/2004 | Petroff |
| 2004/0122483 A1 | 6/2004 | Nathan et al. |
| 2004/0138712 A1 | 7/2004 | Tamarkin et al. |
| 2004/0158150 A1 | 8/2004 | Rabiner |
| 2004/0162546 A1 | 8/2004 | Liang et al. |
| 2004/0162554 A1 | 8/2004 | Lee et al. |
| 2004/0167558 A1 | 8/2004 | Igo et al. |
| 2004/0186425 A1 | 9/2004 | Schneider et al. |
| 2004/0200909 A1 | 10/2004 | McMillan et al. |
| 2004/0202576 A1 | 10/2004 | Aceti et al. |
| 2004/0206365 A1 | 10/2004 | Knowlton |
| 2004/0210214 A1 | 10/2004 | Knowlton |
| 2004/0215101 A1 | 10/2004 | Rioux et al. |
| 2004/0215110 A1 | 10/2004 | Kreindel |
| 2004/0220512 A1 | 11/2004 | Kreindel |
| 2004/0236248 A1 | 11/2004 | Svedman |
| 2004/0236252 A1 | 11/2004 | Muzzi et al. |
| 2004/0243159 A1 | 12/2004 | Shiuey |
| 2004/0243160 A1 | 12/2004 | Shiuey et al. |
| 2004/0251566 A1 | 12/2004 | Kozyuk |
| 2004/0253148 A1 | 12/2004 | Leaton |
| 2004/0253183 A1 | 12/2004 | Uber, III et al. |
| 2004/0264293 A1 | 12/2004 | Laugharn et al. |
| 2005/0010197 A1 | 1/2005 | Lau et al. |
| 2005/0015024 A1 | 1/2005 | Babaev |
| 2005/0027242 A1 | 2/2005 | Gabel et al. |
| 2005/0033338 A1 | 2/2005 | Ferree |
| 2005/0049543 A1 | 3/2005 | Anderson et al. |
| 2005/0055018 A1 | 3/2005 | Kreindel |
| 2005/0080333 A1 | 4/2005 | Piron et al. |
| 2005/0085748 A1 | 4/2005 | Culp et al. |
| 2005/0102009 A1 | 5/2005 | Costantino |
| 2005/0131439 A1 | 6/2005 | Brett et al. |
| 2005/0136548 A1 | 6/2005 | McDevitt |
| 2005/0137525 A1 | 6/2005 | Wang et al. |
| 2005/0139142 A1 | 6/2005 | Kelley et al. |
| 2005/0154309 A1 | 7/2005 | Etchells et al. |
| 2005/0154314 A1 | 7/2005 | Quistgaard |
| 2005/0154443 A1 | 7/2005 | Linder et al. |
| 2005/0163711 A1 | 7/2005 | Nycz et al. |
| 2005/0182385 A1 | 8/2005 | Epley |
| 2005/0182462 A1 | 8/2005 | Chornenky et al. |
| 2005/0191252 A1 | 9/2005 | Mutsui |
| 2005/0197663 A1 | 9/2005 | Schwartz et al. |
| 2005/0203497 A1 | 9/2005 | Speeg |
| 2005/0215987 A1 | 9/2005 | Slatkine |
| 2005/0234527 A1 | 10/2005 | Slatkine |
| 2005/0256536 A1 | 11/2005 | Grundeman et al. |
| 2005/0268703 A1 | 12/2005 | Funck et al. |
| 2006/0036300 A1 | 2/2006 | Kreindel |
| 2006/0058678 A1 | 3/2006 | Vitek et al. |
| 2006/0074313 A1 | 4/2006 | Slayton |
| 2006/0074314 A1 | 4/2006 | Slayton et al. |
| 2006/0079921 A1 * | 4/2006 | Nezhat ............... A61B 17/3403 606/185 |
| 2006/0094988 A1 | 5/2006 | Tosaya et al. |
| 2006/0100555 A1 | 5/2006 | Cagle et al. |
| 2006/0102174 A1 | 5/2006 | Hochman |
| 2006/0111744 A1 | 5/2006 | Makin et al. |
| 2006/0122509 A1 | 6/2006 | Desilets |
| 2006/0206040 A1 | 9/2006 | Greenberg |
| 2006/0206117 A1 | 9/2006 | Harp |
| 2006/0211958 A1 | 9/2006 | Rosenberg et al. |
| 2006/0235371 A1 | 10/2006 | Wakamatsu et al. |
| 2006/0235732 A1 | 10/2006 | Miller et al. |
| 2006/0241672 A1 | 10/2006 | Zadini et al. |

(56) References Cited

U.S. PATENT DOCUMENTS

| | | |
|---|---|---|
| 2006/0241673 A1 | 10/2006 | Zadini |
| 2006/0259102 A1 | 11/2006 | Slatkine |
| 2006/0264809 A1 | 11/2006 | Hansmann et al. |
| 2006/0264926 A1* | 11/2006 | Kochamba .......... A61M 5/14248 606/41 |
| 2006/0293722 A1 | 12/2006 | Slatkine et al. |
| 2007/0005091 A1 | 1/2007 | Zadini et al. |
| 2007/0010810 A1 | 1/2007 | Kochamba |
| 2007/0016234 A1 | 1/2007 | Daxer |
| 2007/0027411 A1 | 2/2007 | Ella et al. |
| 2007/0031482 A1 | 2/2007 | Castro et al. |
| 2007/0035201 A1 | 2/2007 | Desilets et al. |
| 2007/0041961 A1 | 2/2007 | Hwang et al. |
| 2007/0043295 A1 | 2/2007 | Chomas et al. |
| 2007/0055156 A1 | 3/2007 | Desilets et al. |
| 2007/0055179 A1 | 3/2007 | Deem et al. |
| 2007/0060989 A1 | 3/2007 | Deem et al. |
| 2007/0118077 A1 | 5/2007 | Clarke et al. |
| 2007/0118166 A1 | 5/2007 | Nobis et al. |
| 2007/0129708 A1 | 6/2007 | Edwards et al. |
| 2007/0142881 A1 | 6/2007 | Hennings |
| 2007/0156096 A1* | 7/2007 | Sonoda .......... A61M 37/00 604/174 |
| 2007/0179515 A1 | 8/2007 | Matsutani et al. |
| 2007/0191827 A1 | 8/2007 | Lischinsky et al. |
| 2007/0197907 A1 | 8/2007 | Bruder et al. |
| 2007/0197917 A1 | 8/2007 | Bagge |
| 2007/0239075 A1 | 10/2007 | Rosenberg et al. |
| 2007/0239079 A1 | 10/2007 | Manstein et al. |
| 2007/0255355 A1 | 11/2007 | Altshuler et al. |
| 2007/0270745 A1* | 11/2007 | Nezhat .......... A61B 5/6834 604/115 |
| 2007/0282318 A1 | 12/2007 | Spooner et al. |
| 2007/0293849 A1 | 12/2007 | Hennings et al. |
| 2008/0014627 A1 | 1/2008 | Merchant et al. |
| 2008/0015435 A1 | 1/2008 | Cribbs et al. |
| 2008/0015624 A1* | 1/2008 | Sonoda .......... A61M 5/158 606/185 |
| 2008/0027328 A1 | 1/2008 | Klopotek et al. |
| 2008/0027384 A1 | 1/2008 | Wang et al. |
| 2008/0058603 A1 | 3/2008 | Edelstein et al. |
| 2008/0058851 A1 | 3/2008 | Edelstein et al. |
| 2008/0091126 A1 | 4/2008 | Greenburg |
| 2008/0091182 A1 | 4/2008 | Mehta |
| 2008/0109023 A1 | 5/2008 | Greer |
| 2008/0147084 A1 | 6/2008 | Bleich et al. |
| 2008/0172012 A1 | 7/2008 | Hiniduma-Lokuge et al. |
| 2008/0183164 A1 | 7/2008 | Elkins et al. |
| 2008/0188835 A1 | 8/2008 | Hennings et al. |
| 2008/0195036 A1 | 8/2008 | Merchant et al. |
| 2008/0200845 A1 | 8/2008 | Sokka et al. |
| 2008/0200864 A1 | 8/2008 | Holzbaur et al. |
| 2008/0215039 A1 | 9/2008 | Slatkine et al. |
| 2008/0234609 A1 | 9/2008 | Kreindel et al. |
| 2008/0249526 A1 | 10/2008 | Knowlton |
| 2008/0262527 A1 | 10/2008 | Eder et al. |
| 2008/0269668 A1 | 10/2008 | Keenan et al. |
| 2008/0269687 A1 | 10/2008 | Chong et al. |
| 2008/0306476 A1 | 12/2008 | Hennings et al. |
| 2008/0319356 A1 | 12/2008 | Cain et al. |
| 2008/0319358 A1 | 12/2008 | Lai |
| 2009/0012434 A1 | 1/2009 | Anderson |
| 2009/0018522 A1 | 1/2009 | Weintraub et al. |
| 2009/0024192 A1 | 1/2009 | Mulholland |
| 2009/0048544 A1 | 2/2009 | Rybyanets |
| 2009/0088823 A1 | 4/2009 | Barak et al. |
| 2009/0093864 A1 | 4/2009 | Anderson |
| 2009/0118722 A1 | 5/2009 | Ebbers et al. |
| 2009/0124973 A1 | 5/2009 | D'Agostino et al. |
| 2009/0125013 A1 | 5/2009 | Sypniewski et al. |
| 2009/0156958 A1 | 6/2009 | Mehta |
| 2009/0171255 A1 | 7/2009 | Rybyanets et al. |
| 2009/0192441 A1 | 7/2009 | Gelbart et al. |
| 2009/0198189 A1 | 8/2009 | Simons et al. |
| 2009/0221938 A1 | 9/2009 | Rosenberg et al. |
| 2009/0240188 A1 | 9/2009 | Hyde et al. |
| 2009/0248004 A1 | 10/2009 | Altshuler et al. |
| 2009/0270789 A1 | 10/2009 | Maxymiv et al. |
| 2009/0275879 A1 | 11/2009 | Deem et al. |
| 2009/0275899 A1 | 11/2009 | Deem et al. |
| 2009/0275967 A1 | 11/2009 | Stokes et al. |
| 2009/0326439 A1 | 12/2009 | Chomas et al. |
| 2009/0326441 A1 | 12/2009 | Iliescu et al. |
| 2009/0326461 A1 | 12/2009 | Gresham |
| 2010/0004536 A1 | 1/2010 | Rosenberg |
| 2010/0016761 A1 | 1/2010 | Rosenberg |
| 2010/0017750 A1 | 1/2010 | Rosenberg et al. |
| 2010/0022999 A1 | 1/2010 | Gollnick et al. |
| 2010/0030262 A1 | 2/2010 | McLean et al. |
| 2010/0049178 A1 | 2/2010 | Deem et al. |
| 2010/0057056 A1 | 3/2010 | Gurtner et al. |
| 2010/0137799 A1* | 6/2010 | Imai .......... A61M 5/158 604/115 |
| 2010/0210915 A1 | 8/2010 | Caldwell et al. |
| 2010/0228182 A1 | 9/2010 | Clark, III et al. |
| 2010/0228207 A1 | 9/2010 | Ballakur et al. |
| 2010/0331875 A1* | 12/2010 | Sonoda .......... A61M 5/158 606/185 |
| 2011/0028898 A1 | 2/2011 | Clark et al. |
| 2011/0295230 A1 | 12/2011 | O'Dea |
| 2012/0022504 A1 | 1/2012 | Epshtein et al. |
| 2012/0116375 A1 | 5/2012 | Hennings |
| 2012/0136280 A1 | 5/2012 | Rosenberg et al. |
| 2012/0136282 A1 | 5/2012 | Rosenberg et al. |
| 2012/0165725 A1 | 6/2012 | Chomas et al. |
| 2012/0197242 A1 | 8/2012 | Rosenberg |
| 2012/0277587 A1 | 11/2012 | Adanny et al. |
| 2012/0316547 A1 | 12/2012 | Hennings et al. |
| 2013/0023855 A1 | 1/2013 | Hennings et al. |
| 2013/0096596 A1 | 4/2013 | Schafer |
| 2013/0197315 A1 | 8/2013 | Foley |
| 2013/0197427 A1 | 8/2013 | Merchant et al. |
| 2013/0296744 A1 | 11/2013 | Taskinen et al. |
| 2014/0025050 A1 | 1/2014 | Anderson |
| 2014/0031803 A1 | 1/2014 | Epshtein et al. |
| 2014/0107742 A1 | 4/2014 | Mehta |
| 2014/0228834 A1 | 8/2014 | Adanny et al. |
| 2014/0249609 A1 | 9/2014 | Zarsky et al. |
| 2014/0257272 A1 | 9/2014 | Clark, III et al. |
| 2014/0276693 A1 | 9/2014 | Altshuler et al. |
| 2014/0277025 A1 | 9/2014 | Clark, III et al. |
| 2014/0277047 A1 | 9/2014 | Clark, III et al. |
| 2014/0277048 A1 | 9/2014 | Clark, III et al. |
| 2014/0316393 A1 | 10/2014 | Levinson |
| 2015/0064165 A1 | 3/2015 | Perry et al. |

FOREIGN PATENT DOCUMENTS

| | | |
|---|---|---|
| CN | 1159908 | 9/1997 |
| CN | 1484520 A | 3/2004 |
| CN | 1823687 | 8/2006 |
| CN | 2007/20159899 | 12/2007 |
| CN | 2011/31982 | 10/2008 |
| CN | 101795641 | 8/2010 |
| DE | 3838530 | 5/1990 |
| DE | 4426421 | 2/1996 |
| EP | 148116 | 7/1985 |
| EP | 0224934 | 12/1986 |
| EP | 0278074 | 1/1987 |
| EP | 0327490 | 2/1989 |
| EP | 0384831 | 2/1990 |
| EP | 0953432 | 3/1999 |
| FR | 2643252 | 2/1989 |
| GB | 1216813 | 12/1970 |
| GB | 1577551 | 2/1976 |
| GB | 2327614 | 3/1999 |
| JP | 57-139358 | 8/1982 |
| JP | 2126848 | 5/1990 |
| JP | 2180275 | 7/1990 |
| JP | 5215591 | 8/1993 |
| JP | 2000-190976 | 7/2000 |
| JP | 2001516625 | 10/2001 |
| JP | 2002-017742 | 1/2002 |
| JP | 2002-528220 | 9/2002 |

(56) References Cited

FOREIGN PATENT DOCUMENTS

| | | |
|---|---|---|
| JP | 2004-283420 | 10/2004 |
| JP | 2004283420 | 10/2004 |
| JP | 2005087519 | 4/2005 |
| WO | WO 1980/02365 | 11/1980 |
| WO | WO1989/05159 | 6/1989 |
| WO | WO1989/05160 | 6/1989 |
| WO | WO1989/09593 | 10/1989 |
| WO | WO1990/01971 | 3/1990 |
| WO | WO1992/09238 | 6/1992 |
| WO | WO1995/15118 | 6/1995 |
| WO | WO 9729701 | 8/1997 |
| WO | WO9913936 | 3/1999 |
| WO | WO9942138 | 8/1999 |
| WO | WO 2000/36982 | 6/2000 |
| WO | WO 03/030984 | 4/2003 |
| WO | WO 03/941597 | 5/2003 |
| WO | WO2003/047689 | 6/2003 |
| WO | WO2004/000116 | 12/2003 |
| WO | WO2004/069153 | 8/2004 |
| WO | WO2005/009865 | 2/2005 |
| WO | WO2005/105282 | 11/2005 |
| WO | WO2005/105818 | 11/2005 |
| WO | WO2006/053588 | 5/2006 |
| WO | WO 2007/035177 | 3/2007 |
| WO | WO 2007/052662 | 5/2007 |
| WO | WO2007102161 | 9/2007 |
| WO | WO2008/055243 | 5/2008 |
| WO | WO2008/139303 | 11/2008 |
| WO | WO2010/020021 | 2/2010 |
| WO | WO2011/017663 | 2/2011 |
| WO | WO 2012/087506 | 6/2012 |
| WO | WO2013/059263 | 4/2013 |
| WO | WO 2014/009875 | 1/2014 |
| WO | WO 2014/009826 | 3/2014 |
| WO | WO 2014/060977 | 4/2014 |
| WO | WO 2014/097288 | 6/2014 |
| WO | WO 2014/108888 | 7/2014 |
| WO | WO 2014/141229 | 9/2014 |

OTHER PUBLICATIONS

U.S. Appl. No. 11/334,794 (U.S. Pat. No. 7,588,547), filed Jan. 17, 2006 (Sep. 15, 2009), Method and System for Treating Subcutaneous Tissues.
U.S. Appl. No. 12/467,234 (U.S. Pat. No. 8,348,867), filed May 15, 2009 (Jan. 8, 2013), Method for Treating Subcutaneous Tissues.
U.S. Appl. No. 12/467,240, filed May 15, 2009, Apparatus for Treating Subcutaneous Tissues.
U.S. Appl. No. 12/559,488 (U.S. Pat. No. 8,336,643), filed Sep. 14, 2009 (Feb. 5, 2013), System and Method for Treating Subcutaneous Tissues.
U.S. Appl. No. 11/334,805 (U.S. Pat. No. 7,601,128), filed Jan. 17, 2006 (Oct. 13, 2009), Apparatus for Treating Subcutaneous Tissues.
U.S. Appl. No. 11/771,932 (U.S. Pat. No. 9,248,317), filed Jun. 29, 2007 (Feb. 2, 2016), Devices and Methods for Selectively Lysing Cells.
U.S. Appl. No. 11/771,945, filed Jun. 29, 2007, Devices and Methods for Selectively Lysing Cells.
U.S. Appl. No. 11/771,951, filed Jun. 29, 2007, Devices and Methods for Selectively Lysing Cells.
U.S. Appl. No. 13/799,377 (U.S. Pat. No. 9,079,001), filed Mar. 13, 2013 (Jul. 14, 2015), Devices and Methods for Selectively Lysing Cells.
U.S. Appl. No. 14/536,375 (U.S. Pat. No. 9,272,124), filed Nov. 7, 2014 (Mar. 1, 2016), Systems and Devices for Selective Cell Lysis and Methods of Using Same.
U.S. Appl. No. 11/771,960, filed Jun. 29, 2007, Devices and Methods for Selectively Lysing Cells.
U.S. Appl. No. 11/771,966, filed Jun. 29, 2007, Devices and Methods for Selectively Lysing Cells.
U.S. Appl. No. 11/771,972, filed Jun. 29, 2007, Devices and Methods for Selectively Lysing Cells.
U.S. Appl. No. 11/515,634, filed Sep. 5, 2006, Apparatus and Method for Disrupting Subcutaneous Structures.
U.S. Appl. No. 12/555,746, filed Sep. 8, 2009, High Pressure Pre-Burst for Improved Fluid Delivery.
U.S. Appl. No. 12/247,853, filed Oct. 8, 2008, Ultrasound Apparatus With Treatment Lens.
U.S. Appl. No. 12/787,377 (U.S. Pat. No. 9,358,033), filed May 25, 2010 (Jun. 7, 2016), Fluid-Jet Dissection System and Method for Reducing the Appearance of Cellulite.
U.S. Appl. No. 15/151,370, filed May 10, 2016, Fluid-Jet Dissection System and Method for Reducing the Appearance of Cellulite.
U.S. Appl. No. 12/247,879, filed Oct. 8, 2008, Device and Method for Monitoring a Treatment Area.
U.S. Appl. No. 12/409,366 (U.S. Pat. No. 8,167,280), filed Mar. 23, 2009 (May 1, 2012), Bubble Generator Having Disposable Bubble Cartridges.
U.S. Appl. No. 12/787,382 (U.S. Pat. No. 8,518,069), filed May 25, 2010 (Aug. 27, 2013), Dissection Handpiece and Method for Reducing the Appearance of Cellulite.
U.S. Appl. No. 13/712,429 (U.S. Pat. No. 9,011,473), filed Dec. 12, 2012 (Apr. 21, 2015), Dissection Handpiece and Method for Reducing the Appearance of Cellulite.
U.S. Appl. No. 13/772,718 (U.S. Pat. No. 8,753,339), filed Feb. 21, 2013 (Jun. 17, 2014), Dissection Handpiece and Method for Reducing the Appearance of Cellulite.
U.S. Appl. No. 13/712,694 (U.S. Pat. No. 9,005,229), filed Dec. 12, 2012 (Apr. 14, 2015), Dissection Handpiece and Method for Reducing the Appearance of Cellulite.
U.S. Appl. No. 13/772,753 (U.S. Pat. No. 8,574,251), filed Feb. 21, 2013 (Nov. 5, 2013), Dissection Handpiece and Method for Reducing the Appearance of Cellulite.
U.S. Appl. No. 13/957,744 (U.S. Pat. No. 9,179,928), filed Aug. 2, 2013 (Nov. 10, 2015), Dissection Handpiece and Method for Reducing the Appearance of Cellulite.
U.S. Appl. No. 14/290,843 (U.S. Pat. No. 8,900,261), filed May 29, 2014 (Dec. 2, 2014), Tissue Treatment System for Reducing the Appearance of Cellulite.
U.S. Appl. No. 14/290,852 (U.S. Pat. No. 8,900,262), filed May 29, 2014 (Dec. 2, 2014), Device for Dissection of Subcutaneous Tissue.
U.S. Appl. No. 14/290,907 (U.S. Pat. No. 8,899,881), filed May 29, 2014 (Mar. 17, 2015), Methods and Handpiece for Use in Tissue Dissection.
U.S. Appl. No. 14/290,847 (U.S. Pat. No. 8,906,054), filed May 29, 2014 (Dec. 9, 2014), Apparatus for Reducing the Appearance of Cellulite.
U.S. Appl. No. 14/290,857 (U.S. Pat. No. 8,920,452), filed May 29, 2014 (Dec. 30, 2014), Methods of Tissue Release to Reduce the Appearance of Cellulite.
U.S. Appl. No. 14/290,858 (U.S. Pat. No. 8,894,678), filed May 29, 2014 (Nov. 25, 2014), Cellulite Treatment Methods.
U.S. Appl. No. 14/579,721 (U.S. Pat. No. 9,078,688), filed Dec. 22, 2014 (Jul. 14, 2015), Handpiece for Use in Tissue Dissection.
U.S. Appl. No. 14/579,821 (U.S. Pat. No. 9,044,259), filed Dec. 22, 2014 (Jun. 2, 2015), Methods for Dissection of Subcutaneous Tissue.
U.S. Appl. No. 15/162,431 (U.S. Pat. No. 9,757,145), filed May 23, 2016 (Sep. 12, 2017), Dissection Handpiece and Method for Reducing the Appearance of Cellulite.
U.S. Appl. No. 15/673,096, filed Aug. 9, 2017, Handpieces for Tissue Treatment.
U.S. Appl. No. 13/533,745 (U.S. Pat. No. 9,364,246), filed Jun. 26, 2012 (Jun. 14, 2016), Dissection Handpiece and Method for Reducing the Appearance of Cellulite.
U.S. Appl. No. 14/060,437 (U.S. Pat. No. 9,358,064), filed Oct. 22, 2013 (Jun. 7, 2016), Handpiece and Methods for Performing Subcutaneous Surgery.
U.S. Appl. No. 14/296,353 (U.S. Pat. No. 9,510,849), filed Jun. 4, 2014 (Dec. 6, 2016), Devices and Methods for Performing Subcutaneous Surgery.
U.S. Appl. No. 15/339,585, filed Oct. 31, 2016, Modular Systems for Treating Tissue.

(56) References Cited

OTHER PUBLICATIONS

U.S. Appl. No. 12/852,029 (U.S. Pat. No. 9,486,274), filed Aug. 6, 2010 (Nov. 8, 2016), Dissection Handpiece and Method for Reducing the Appearance of Cellulite.
U.S. Appl. No. 15/277,761, filed Sep. 27, 2016, Methods for Efficiently Reducing the Appearance of Cellulite.
U.S. Appl. No. 12/975,966 (U.S. Pat. No. 8,439,940), filed Dec. 22, 2010 (May 14, 2013), Dissection Handpiece With Aspiration Means for Reducing the Appearance of Cellulite.
U.S. Appl. No. 14/698,315, filed Apr. 28, 2015, System for Tissue Dissection and Aspiration.
U.S. Appl. No. 13/788,293 (U.S. Pat. No. 9,039,722), filed Feb. 27, 2013 (May 26, 2015), Dissection Handpiece With Aspiration Means for Reducing the Appearance of Cellulite.
U.S. Appl. No. 12/245,647, filed Oct. 3, 2008, Ultrasound Device Including Acoustic Coupling Gel Dispenser.
U.S. Appl. No. 12/260,359, filed Oct. 29, 2008, Ultrasound Enhancing Target for Treating Subcutaneous Tissue.
U.S. Appl. No. 12/419,905, filed Apr. 7, 2009, Fiber Growth Promoting Implants for Reducing the Appearance of Cellulite.
International Search Report dated Apr. 9, 2012 from corresponding International Patent Application No. PCT/US11/62449.
Albrecht, T., et al., Guidelines for the Use of Contrast Agents in Ultrasound, Ultraschall in Med 2004, Jan. 2004, nn. 249-256, vol. 25.
Bindal, Dr. V. V., et al., Environmental Health Criteria for Ultrasound, International Programme on Chemical Safety, 1982, on. 1-153, World Health Organization.
Boyer, J. et al., Undermining in Cutaneous Surgery, Dermatol Surg 27:1, Jan. 2001, pp. 75-78, Blackwell Science, Inc.
Brown, Ph.D., S., Director of Plastic Surgery Research, UT Southwestern Medical Center, Dallas, USA What Happens After Treatment With the UltroShape Device, UltraShape Ltd., Tel Aviv, Israel (2005).
Cartensen, E.L., Allerton Conference for Ultrasonics in Biophysics and Bioengineering: Cavitation, Ultrasound in Med. & Biol., 1987, on. 687-688, vol. 13, Perzamon Journals Ltd.
Chang, Peter P., et al., Thresholds for Inertial Cavitation in Albunex Suspensions Under Pulsed Ultrasound Conditions, IEEE Transactions on Ultrasonics, Ferroelectrics, and Frequency Control, Jan. 2001, pp. 161-170, vol. 48, No. I.
Chen, Wen-Shiang, Ultrasound Contrast Agent Behavior near the Fragmentation Threshold, 2000 IEEE Ultrasonics Symposium, 2000, pp. 1935-1938.
Dijkmans, P.A., et al., Microbubbles and Ultrasound: From Diagnosis to Therapy, Eur J Echocardiography, 2004, pp. 245-256, vol. 5, Elsevier Ltd., The Netherlands.
Farlex "Chamber" <URL: http://www.thefreedictionary.com/chamber>, retrieved Jun. 16, 2013, 4pages.
Feril, L.B., et al., Enhanced Ultrasound-Induced Apoptosis and Cell Lysis by a Hypnotic Medium, International Journal of Radiation Biology, Feb. 2004, PO. 165-175, vol. 2, Taylor & Francis Ltd., United Kingdom.
Feril, Jr., Loreto B., et al., Biological Effects of Low Intensity Ultrasound: The Mechanism Involved, and its Implications on Therapy and on Biosafety of Ultrasound, J. Radial. Res., 2004, nn. 479-489, vol. 45.
Forsberg, Ph.D., F., et al., On the Usefulness of the Mechanical Index Displayed on Clinical Ultrasound Scanners for Predicting Contrast Microbubble Destruction, J Ultrasound Med, 2005, pp. 443-450, vol. 24, American Institute of Ultrasound in Medicine.
Green, Jeremy B. et al. Therapeutic approaches to cellulite. Seminars in Cutaneous Medicine and Surgery, vol. 34, Sep. 2015.
Green, Jeremy B. et al. Cellfina observations: pearls and pitfalls, Seminars in Cutaneouse Medicine and Surgery, vol. 34, Sep. 2015.
Hanscom, D.R., Infringement Search Report prepared for K. Angela Macfarlane, Esq., Chief Technology Counsel, The Foundry, Nov. 15, 2005.
Hexsel, D. et al, Side-By-Side Comparison of Areas with and without Cellulite Depressions Using Magnetic Resonance Imaging, American Society for Dermatologic Surgery, Inc., 2009, pp. 1-7,Wiley Periodicals, Inc.
Hexsel, M.D., Doris Maria, et al., Subcision: a Treatment for Cellulite, International journal of Dermatology 2000, on. 539-544, vol. 39.
Holland, Christy K., et al,, In Vitro Detection of Cavitation Induced by a Diagnostic Ultrasound System, IEEE Transactions on Ultrasonics, Ferroelectrics, and Frequency Control, Jan. 1992, pp. 95-101, vol. 39, No. I.
Internet Web Site—www.icin.nllread/project 21, The Interuniversity Cardiology Institute of the Netherlands, 3 pgs., visited Dec. 22, 2005.
Internet Web Site—www.turnwoodinternational.comiCellulite.htm, Acthyderm Treating Cellulite, Aug. 5, 2005, 4pgs., visited Jan. 12, 2006.
Khan, M. et al., Treatment of cellulite—Part I. Pathophysiology, J Am Acad Dermatol, 2009, vol. 62, No. 3, pp. 361-370.
Khan, M. et al., Treatment of cellulite—Part II. Advances and controversies, JAm Acad Dermatol, 2009, vol. 62, No. 3, pp. 373-384.
Kaminer, Michael S. et al. Multicenter Pivotal Study of Vacuum-Assisted Precise Tissue Release for the Treatment of Cellulite. American Society for Dermatologic Surgery, Inc. Sermatol Surg 2015:41:336-347 (2015).
Lawrence, M.D., N., et al., The Efficacy of External Ultrasound-Assisted Liposuction: A Randomized Controlled Trial, Dermatol SUII!, Apr. 2000, nn. 329-332, vol. 26, Blackwell Science, Inc.
Letters to the Editor on the Thermal Motions of Small Bubbles, Ultrasound in Med. & Biol., 1984, pp. L377-L379, Pergamon Press Ltd., U.S.A.
Michaelson, Solomon M., et al., Fundamental and Applied Aspects of Nonionizing Radiation, Rochester International Conference on Environmental Toxicity, 75h, 1974, pp. 275-299, Plenum Press, New York and London.
Miller, Douglas 1., A Review of the Ultrasonic Bioeffects of Microsonation, Gas-Body Activiation, and Related Cavitation-Like Phenomena, Ultrasound in Med. & Biol., 1987, pp. 443-470, vol. 13, Pergamon Journals Ltd.
Miller, Douglas 1., et al., Further Investigations of ATP Release From Human Erythrocytes Exposed to Ultrasonically Activated Gas-Filled Pores, Ultrasound in Med. & Biol., 1983, pp. 297-307, vol. 9, No. 3, Pergamon Press Ltd., Great Britain.
Miller, Douglas L., et al., On the Oscillation Mode of Gas-filled Micropores, 1. Acoust. Soc. Am., 1985, pp. 946-953, vol. 77 (3).
Miller, Douglas L., Gas Body Activation, Ultrasonics, Nov. 1984, pp. 261-269, vol. 22, No. 6, Butterworth & Co. Ltd.
Miller, Douglas L., Microstreaming Shear as a Mechanism of Cell Death in Elodea Leaves Exposed to Ultrasound, Ultrasound in Med. & Biol., 1985, op. 285-292, vol. II, No. 2, Pergamon Press, U.S.A.
Miller, Morton W., et al., A Review of In Vitro Bioeffects of Inertial Ultrasonic Cavitation From a Mechanistic Perspective, Ultrasound in Med. & Biol., 1996, nn. 1131-1154, vol. 22, No. 9.
Nyborg, Dr. Wesley L., Physical Mechanisms for Biological Effects of Ultrasound, HEW Publicaton (FDA) 78-8062, Sep. 1977, pp. I-59, U.S. Department of Health, Education, and Welfare, Rockville, Maryland.
Orentreich, D. et al., Subcutaneous Incisionless (Subcision) Surgery for the Correction of Depressed Scars and Wrinkles, Dermatol Surg, 1995:21,1995, pp. 543-549, Esevier Science Inc.
Carstensen et al., Biological Effects of Acoustic Cavitation, University of Rochester, Rochester, New York, May 13-16, 1985.
Rohrich,R.J., et al., Comparative Lipoplasty Analysis of in Vivo-Treated Adipose Tissue, Plastic and Reconstructive Surgery, May 2000, 105(6), pp. 2152-2158.
Sasaki, Gordon H. MD, Comparison of Results of Wire Subcision Peformed Alone, With Fills, and/or With Adjacent Surgical Procedures, Aesthetic Surgery Journal, vol. 28, No. 6, Nov./Dec. 2008, p. 619-626.
Scheinfeld, M.D., J.D. Faad, N.S., Liposuction Techniques: External Ultrasound-Assisted, eMedicine.com, Inc., 2005.

(56) References Cited

OTHER PUBLICATIONS

Villarraga, M.D., H.R., et al., Destruction of Contrast Microbubbles During Ultrasound Imaging at Conventional Power Output, Journal of the American Society of Echocardiography, Oct. 1997, pp. 783-791.
Vivino, Alfred A., et al., Stable Cavitation at low Ultrasonic Intensities Induces Cell Death and Inhibits H-TdR Incorporation by Con-A-Stimulated Murine Lymphocytes In Vitro, Ultrasound in Med. & Biol., 1985, pp. 751-759, vol. II, No. 5, Pergamon Press Ltd.
Weaver, James C. Electroporation; a general phenomenon for manipulating cells and tissues. J Cell Biochem. Apr. 1993; 51(4):426-35.
Patent Search, CTX System Microbubble Cavitation, Nov. 11, 2005.

\* cited by examiner

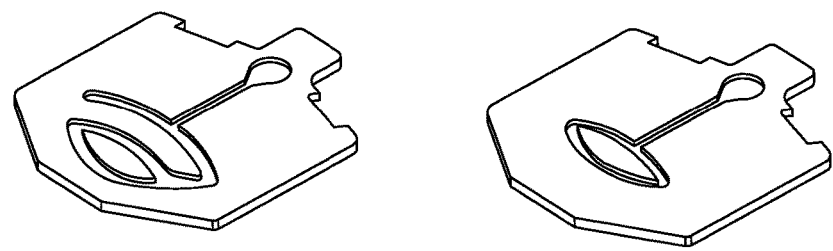
FIG. 6B
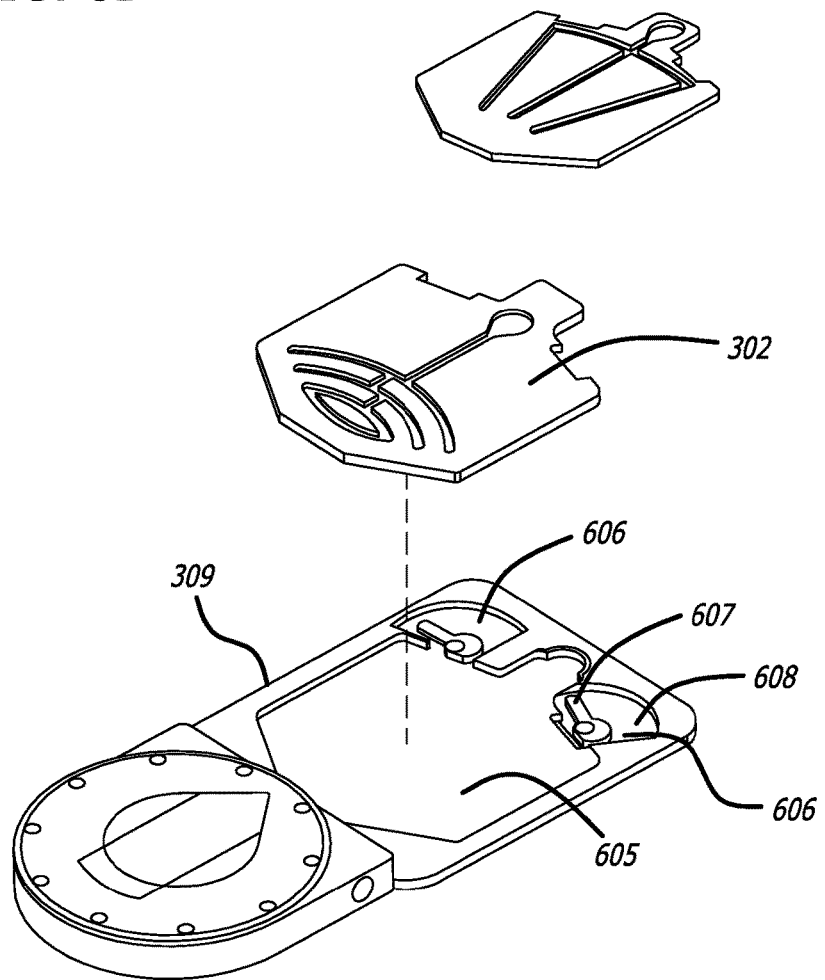

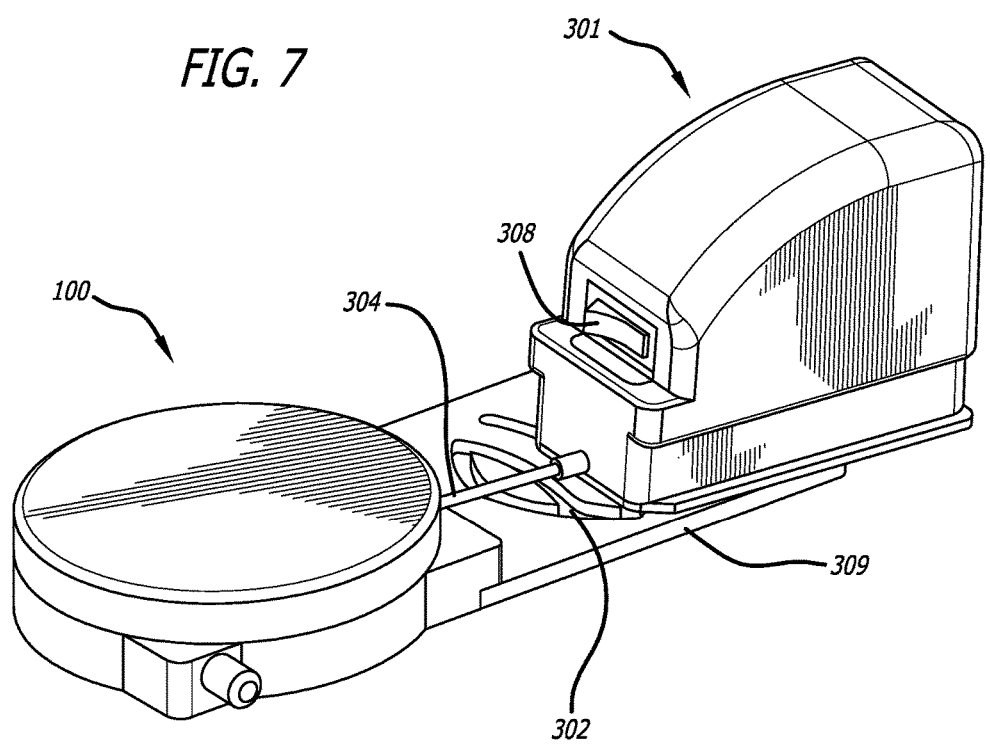

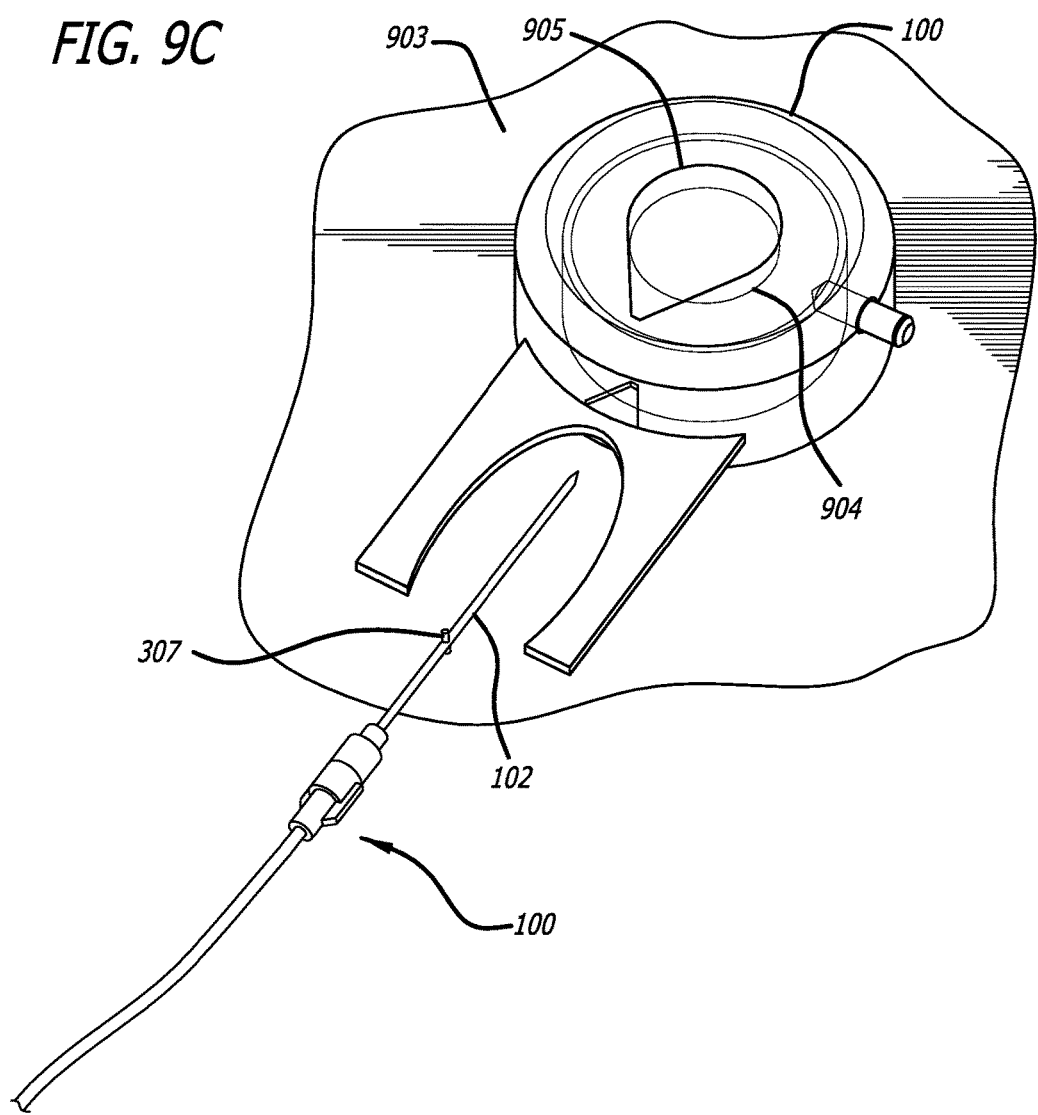

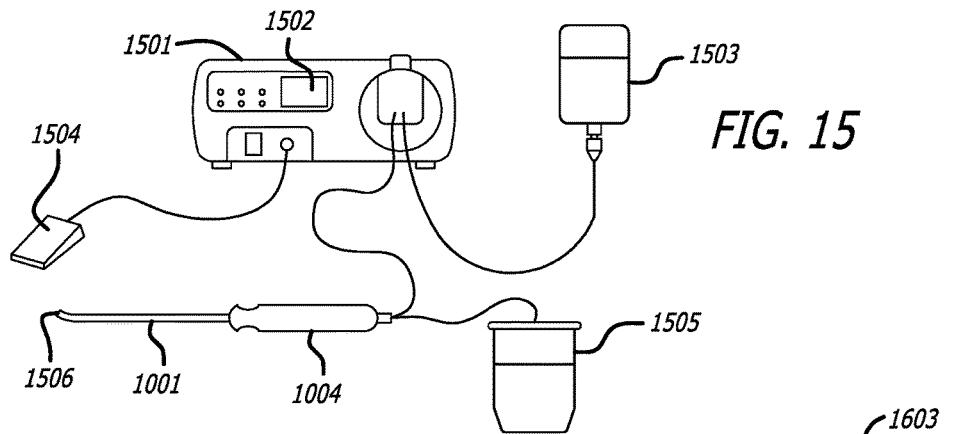
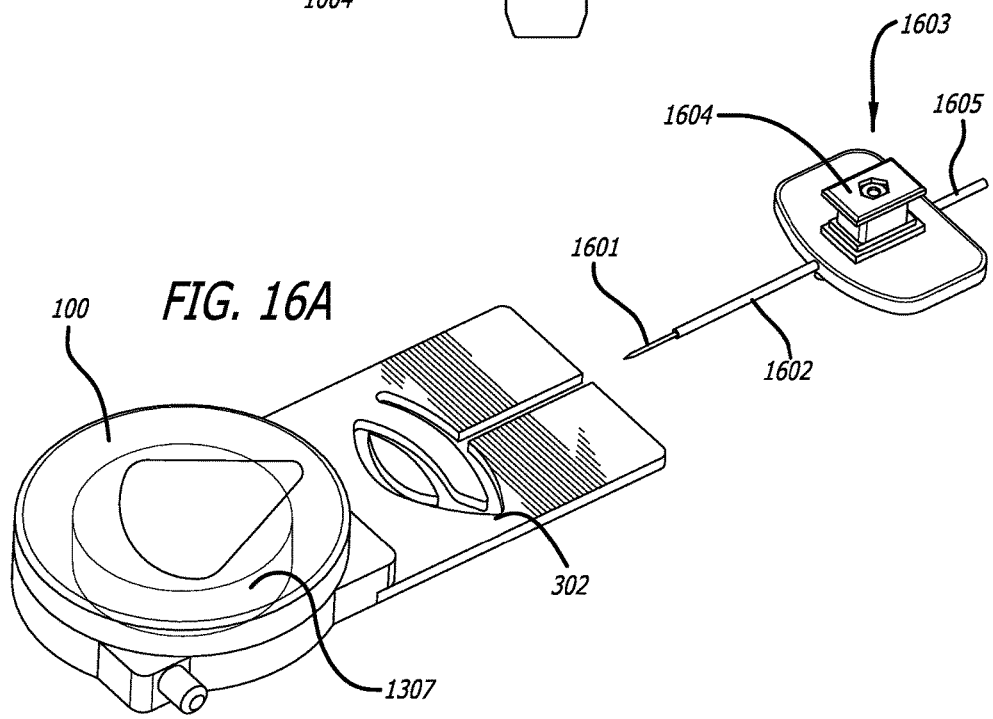
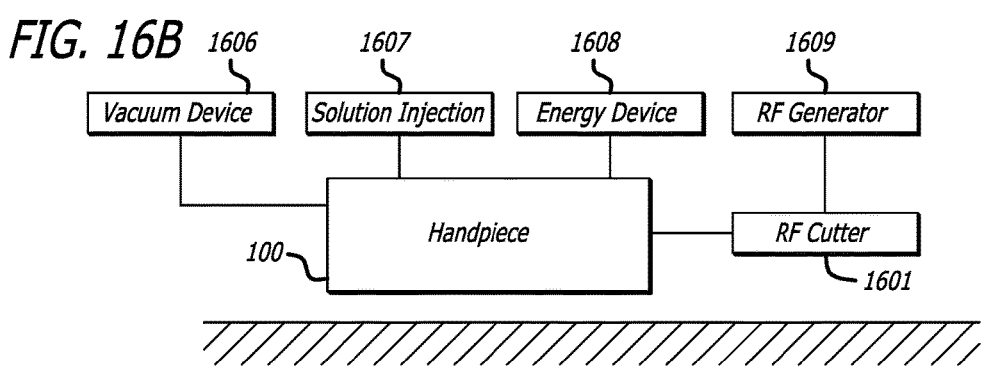

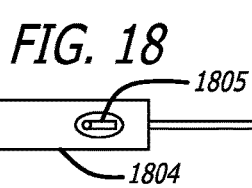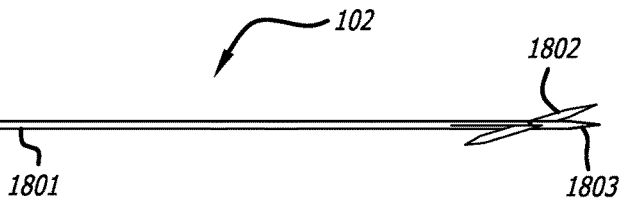
FIG. 18
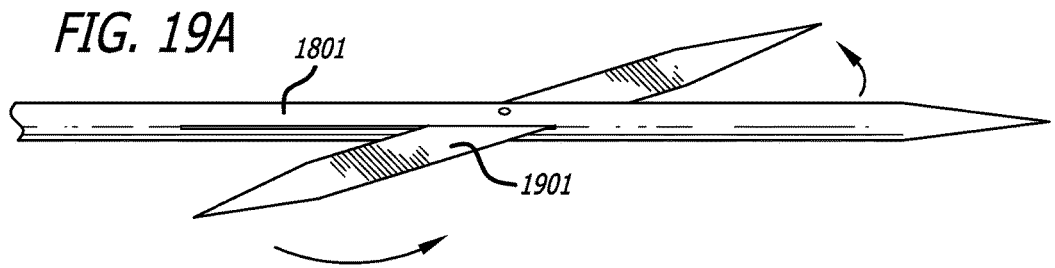
FIG. 19A
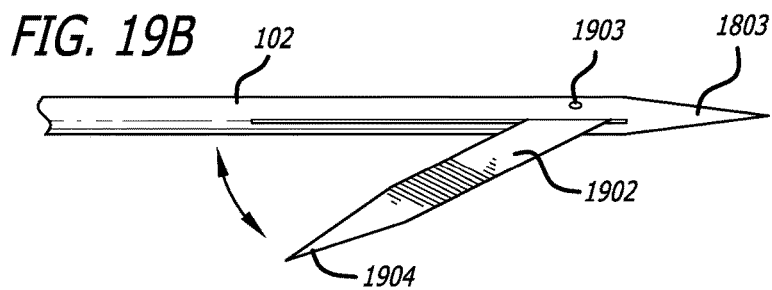
FIG. 19B
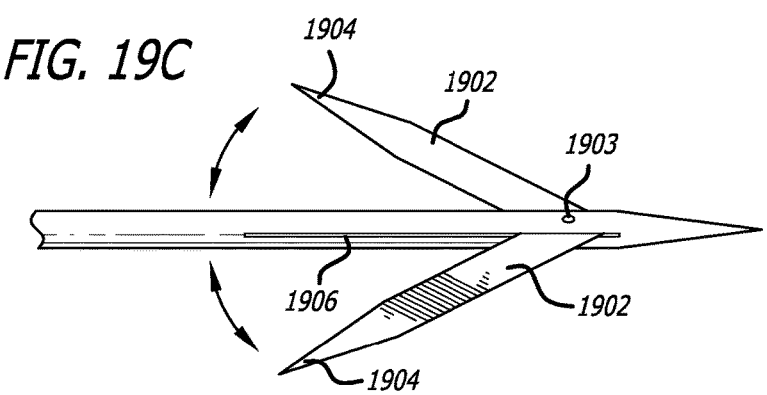
FIG. 19C

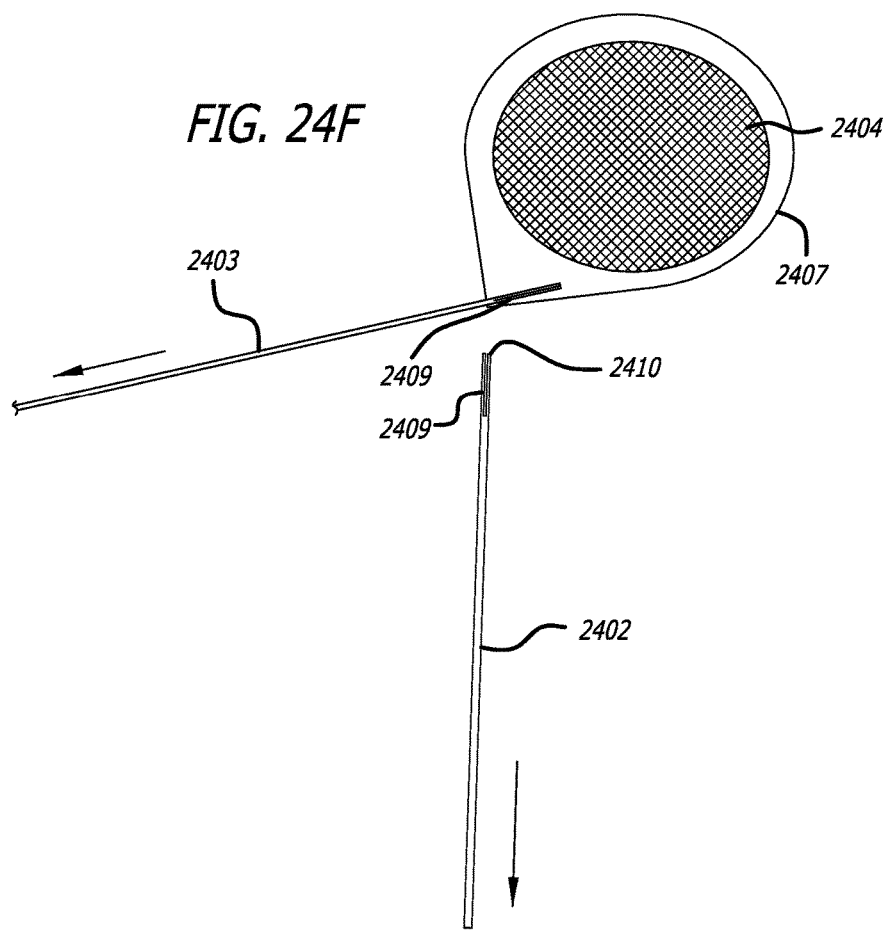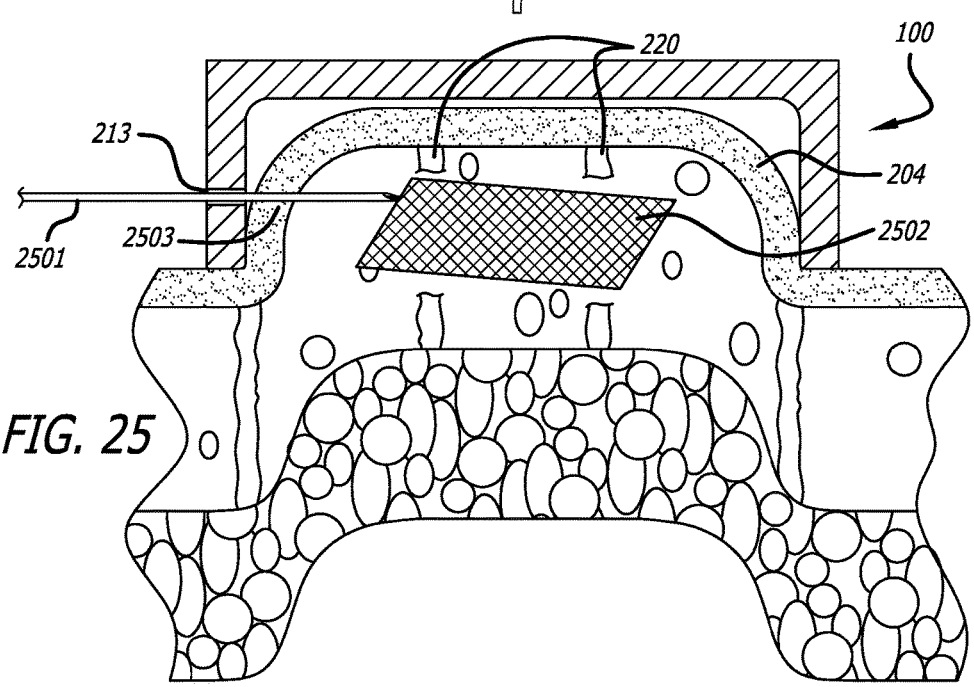

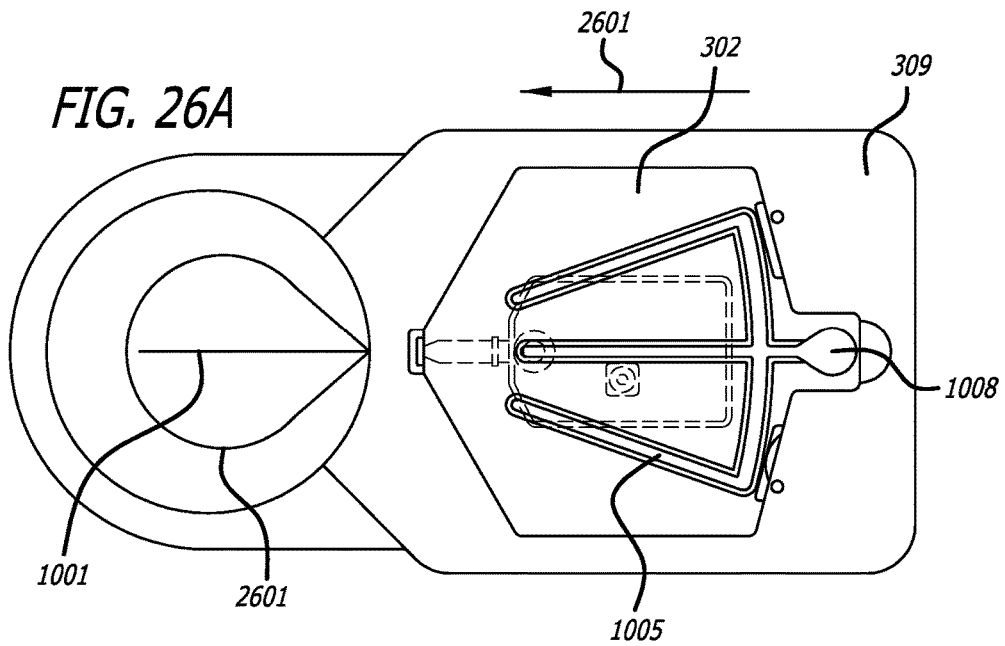
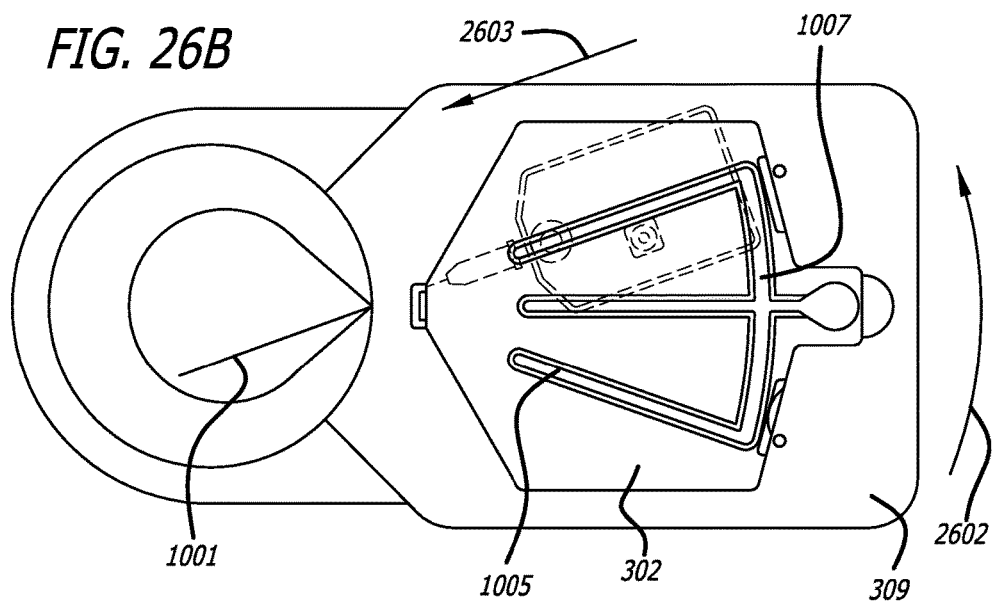

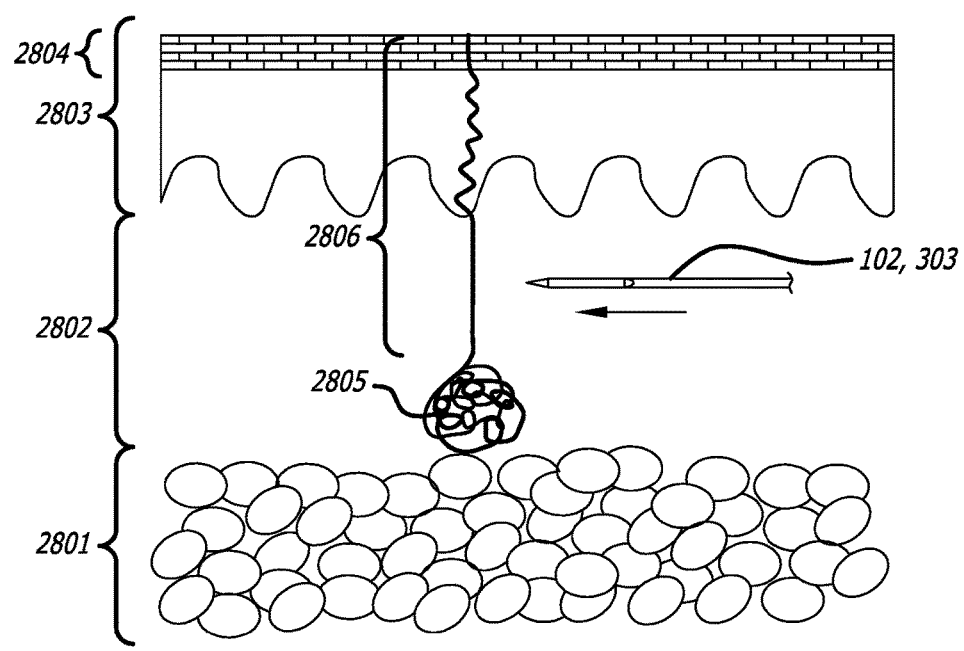

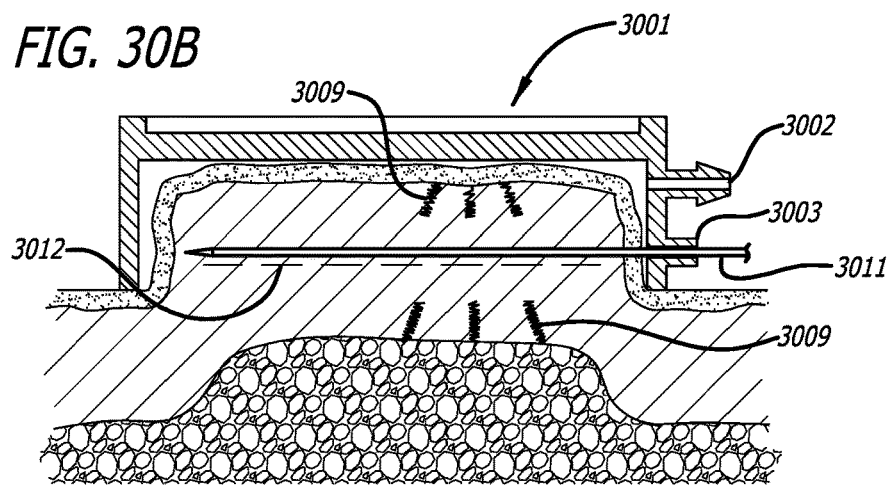
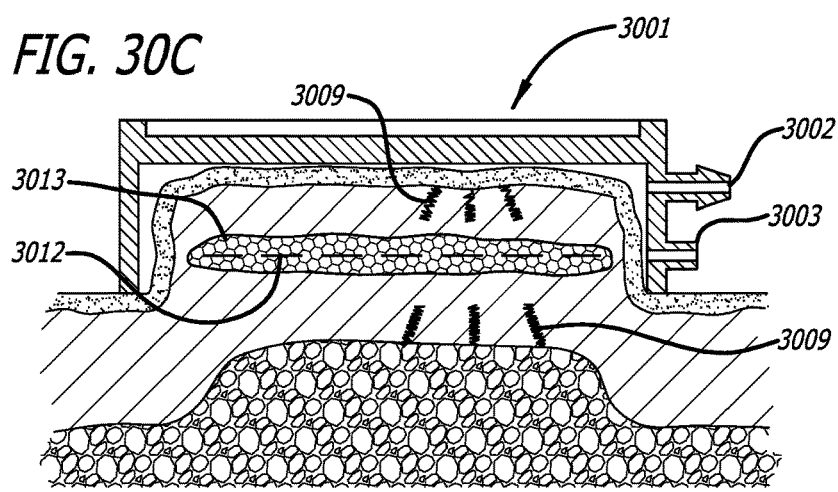
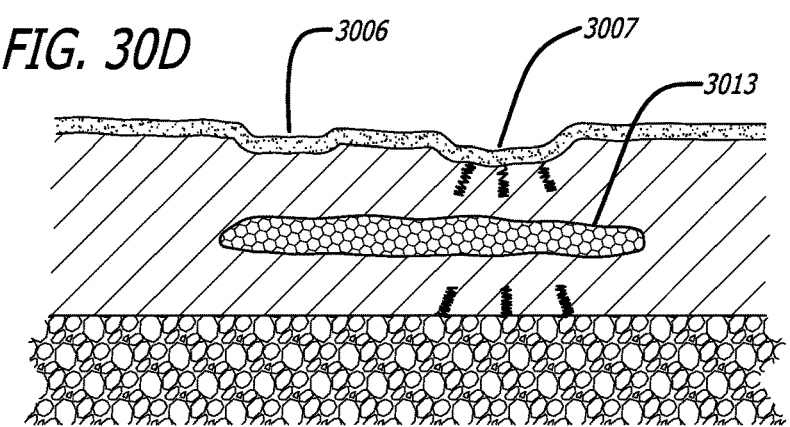

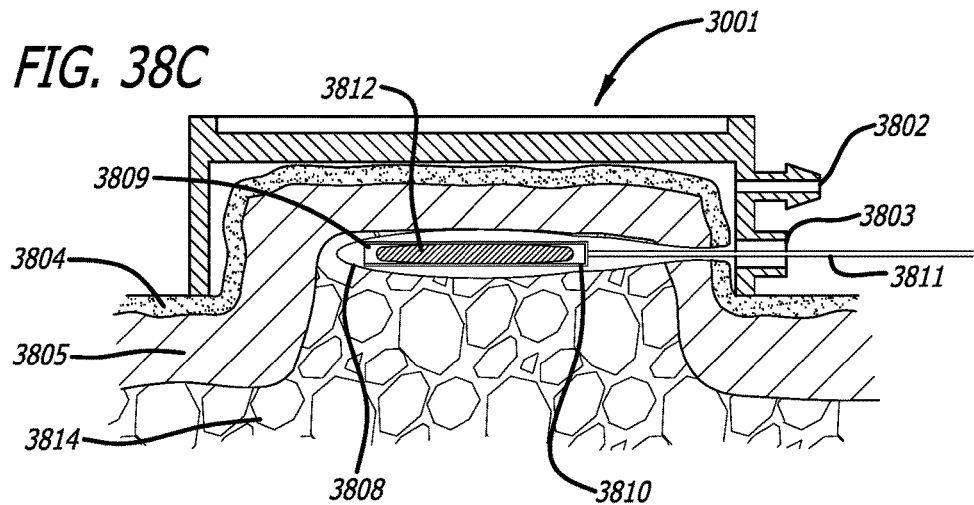
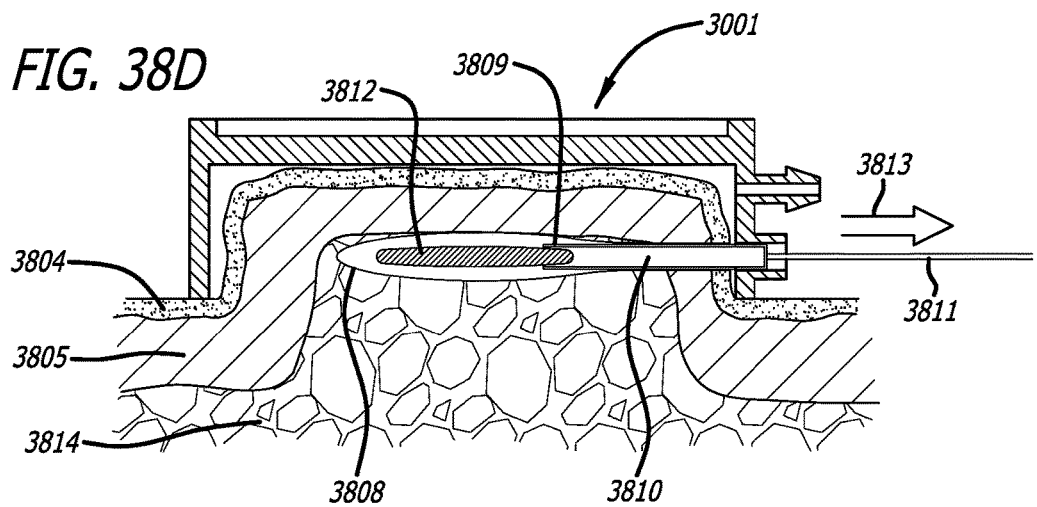
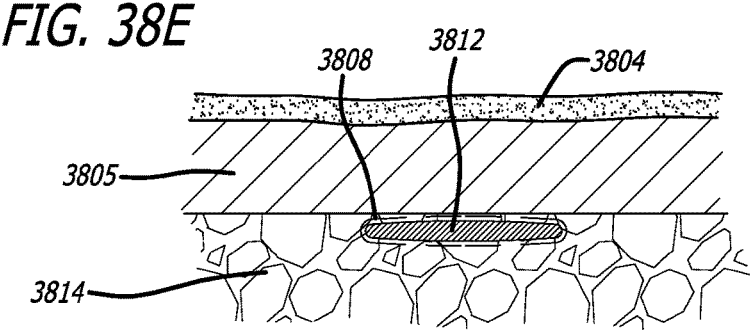

MODULAR SYSTEMS FOR TREATING TISSUE

CROSS-REFERENCES TO RELATED APPLICATIONS

This application is a continuation of co-pending U.S. patent application Ser. No. 14/296,353, filed Jun. 4, 2014, which is a continuation of U.S. patent application Ser. No. 14/060,437, filed on Oct. 22, 2013, now U.S. Pat. No. 9,358,064, which is a continuation-in-part of co-pending U.S. patent application Ser. No. 13/712,429, filed Dec. 12, 2012, now U.S. Pat. No. 9,011,473, which is a continuation of U.S. patent application Ser. No. 12/787,382, filed May 25, 2010, now U.S. Pat. No. 8,518,069, which claims priority from U.S. Provisional Application No. 61/232,385 filed Aug. 7, 2009 and U.S. Provisional Application No. 61/286,750 filed Dec. 15, 2009, all of which are incorporated by reference in their entirety.

FIELD OF THE INVENTION

The presesent invention relates to surgical tools and methods for performing corrective and cosmetic surgical procedures in the subcutaneous tissue space.

BACKGROUND

Atrophic Scars, Acne

Atrophic scars are the most ubiquitous type of scars, and are characterized by skin depressions caused by a loss of underlying supporting structure, such as collagen, fat or muscle. Various types of atrophic scars exist, secondary to conditions like trauma, inflammation or disease. The most frequently observed types of atrophic scars are those caused by common acne. Subcutaneous treatment of atrophic scars has the potential of elevating the sunken depressions, provided that an adequate subdermal pocket can be created, to be filled with either endogenous wound healing tissue or with injected or implanted material. Key to the creation of an adequate pocket is the dissection of fibrous strands or septae anchoring the skin in many atrophic scars to the underlying tissue. A surgical treatment sometimes used for the treatment of atrophic scars is Subcision®, in which a tri-beveled needle is repeatedly inserted into the subcutaneous space to cut subcutaneous tissue, specifically the fibrous septae, releasing the skin from its attachment to deeper structures. In a typical procedure the needle may be inserted many times, moving in fan-shape patterns radiating from its access site. This may be followed by a fan-like sweeping action, to ensure full detachment of the tissue layers. This procedure makes the method time consuming and prone to inadvertent deeper injury due to the large number of lancing movements with the needle. Additionally, in clinical practice, re-depression after an initially seemingly successful procedure is commonly observed. It is thought initially blood and extracellular fluid fill a pocket around the dissected needle tracks, that provides lift to the treated scar. When an inadequate pocket is created, resorption of the coagulated blood and fluids over time may cause the pocket to collapse, causing the late failure. Re-depression may also occur from reformation of scar tissue in response to the multiple planes of injury.

Wrinkles

Facial skin is unique because of its connections to the underlying Superficial Muscular Aponeurotic System (SMAS). The SMAS is a layer of musculature, responsible for facial expressions and is attached to facial skin through numerous fibrous septae. As a consequence, skin regions heavily involved in facial expressions are densely attached, and with progressing age such areas will start to show such expression lines known as wrinkles, crow's feet and laughing lines. Two approaches are commonly used in cosmetic surgery to improve the appearance of skin around and over these expression lines. One relies on subdermal tightening (Plication) of the SMAS, which tightens the overlying skin through the attachment septae, after which the excess skin is dissected. In this case the role of the septae is beneficial. The other approach employs fillers, like collagen or hyaluronic acid to bulk up the space below the skin. This approach by itself often results in unsatisfactory results, because of the fixed attachment of the skin to the underlying SMAS. In these cases, controlled severing of the fibrous septae may allow for a more effective use of the fillers to reduce the appearance of expression lines.

Subcutaneous Implants

Subcutaneous implants may be used for a variety of purposes. They include shape-enhancing implants used in cosmetic or reconstructive surgery and therapeutically used implants like subcutaneous venous access ports, battery packs for implanted electronic devices, implanted drug delivery devices and other implanted medical devices. Rapid and controllable creation of a subcutaneous pocket is a key component of the implantation procedure for such devices.

Wound Healing

Contractile scar formation can be a serious and sometimes debilitating side effect of wound healing. Tension within the plane of the skin at the site of the wound is generally considered a significant factor in the development of contractile scarring. In the presence of non-elastic fibrous septae connecting the dermis to the underlying subcutaneous tissue around a wound, tension from the suture used to close the wound may be highly localized at the site of the wound. The skin itself tends to be more elastic than the fibrous septae connecting it to the underlying tissue. Consequently, severing the fibrous septae may relieve the local stress, as the tension is distributed over a wider area of skin.

Liposuction

Cosmetic liposuction is one of the most commonly performed cosmetic surgical procedures. While the results are generally favorable, there is a certain percentage of patients where uneven subcutaneous fat distributions or skin irregularities are observed at the end of the healing period. Frequently, these are caused by the presence of fibrous septae connecting the skin to underlying subcutaneous tissue layers, and, occasionally, by the development of scar-like adhesions after liposuction surgery. Both of these phenomena may cause a lack of mobility which prevents the skin from assuming the desired smooth contour lines of the treated body parts. Additionally, secondary treatment procedures are sometimes performed, in which adipose tissue is moved or transplanted from areas with excess fat to areas with insufficient support for the overlying skin. The presence of scar-like adhesions or fibrous septae connecting the skin to underlying subcutaneous layers may interfere with a physician's ability to remove unwanted fat, or reposition such fat at desired locations. All these cases have in common the presence of unwanted connective tissue in a subcutaneous space. Traditional open cosmetic surgery would negate the advantages of the minimally invasive liposuction procedure, and a minimally invasive procedure to treat the unwanted connective tissue is needed to complement liposuction in these patients.

Hyperhidrosis

Hyperhidrosis is a condition characterized by an excessive production of sweat by echini sweat glands, specifically in the armpits, hands and feet. Eccrine sweat glands are mostly located in a relatively narrow tissue region underneath the dermis and are innervated by branches of the sympathetic nerve system. Current treatments range from the use of prescription strength aluminium chloride (antipersiprant) and botulin injection, to surgery, including sweat gland extraction and thoracic sympathectomy, in which a branch of the sympathetic nerve system is severed. Sweat gland extraction may be time consuming and labor-intensive, while significant side effects of thoracic sympathectomy have been reported.

In all these cases, there is a need for a device and a method that enable an efficient performance of subcutaneous corrective surgery, capable of creating a subcutaneous dissection plane, severing certain target anatomical structures and, where necessary, providing a tissue pocket for further corrective procedures.

SUMMARY OF THE INVENTION

A minimally invasive subcutaneous treatment device is disclosed. The device comprises a handpiece having a perimeter elevation and a top which cooperatively define a recessed area with an inner side of the perimeter elevation and the top defining an apposition surface facing into the recessed area; a conduit extending through a side of the perimeter elevation to the recessed area; a tool configured to at least partially extend through the conduit and into the recessed area; and a guidance track operably connected to the handpiece, wherein the guidance track is configured to constrain a portion of the tool in contact with the guidance track to move along a predetermined path to cooperatively move a distal end of the tool within the recessed area in a plane substantially parallel to the top of the handpiece and within a region of a predetermined shape defined by the predefined path.

In some aspects, the device further comprises an entry hole disposed on an inner side of the conduit and facing said recessed area, said entry hole defining a tool pivot point when a distal end of the tool is inserted through the conduit and into the recessed area, wherein the conduit widens outward toward an outer side of the perimeter elevation such that a distal end of the tool inserted through the entry hole moves in one direction when a proximal end of the tool outside the conduit moves in an opposite direction.

In some aspects, the device may also comprise a platform operatively connected to the handpiece, wherein the platform includes the guidance track; and a guide pin operably connected to the tool, said guide pin slidably engaging the guidance track such that the tool is constrained to move in accordance with the predetermined path. In some aspects, the platform can be fixed with respect to the handpiece and substantially orthogonal to a bottom edge of the handpiece. The guidance track may form a groove in a top of the platform, or, in some aspects, the guidance track is a contour formed from an edge of the platform. The guidance track may include an undercut portion and the guide pin can have an enlarged head such that the interference between the enlarge head and the undercut portion of the guidance track inhibits removal of the enlarged head from the guidance track while permitting the guide pin to be moved in accordance with the predetermined path.

In some aspects, the tool comprises a cutting blade and a reciprocating motor coupled to the cutting blade, said reciprocating motor reciprocating the cutting blade. The tool may further include a sleeve, wherein the cutting blade is at least partially slidably disposed within the sleeve. The tool may also include an injection device and a nozzle, wherein the nozzle is configured to discharge a fluid in a direction parallel to the top of the handpiece and configured to increase a kinetic energy of the fluid when the fluid is injected by the injection device through the nozzle.

In further aspects, the top of the handpiece is configured to be adjustable and configured to change the distance between an inner side of the top of the handpiece and a bottom edge of the perimeter elevation and changes a volume of the recessed area when the top is adjusted. In some aspects, the handpiece includes a reversible lid, and, the top of the handpiece being configured to be adjustable includes the reversible lid being configured to be disconnected from the handpiece, turned over, and reconnected. In certain aspects, the top of the handpiece includes a rigid upper lid and a rigid lower lid, the rigid upper lid being fixed with respect to the perimeter elevation, the device further including an inflatable bladder disposed between the rigid upper lid and rigid lower lid, wherein the rigid lower lid is configured to move up and down with respect to a wall of the perimeter elevation, the rigid inner lid being at its lowest point when the bladder is fully expanded, and being at its highest point when the bladder is deflated. In other aspects, the top of the handpiece is operably connected to a perimeter wall of the perimeter elevation by a threaded engagement, the top of the handpiece being rotatably mounted to the perimeter wall, and wherein rotation of the top relative to the perimeter wall adjusts the volume of the recessed area. The top of the handpiece may also include an upper rim disposed between an upper edge of an outer wall and an upper edge of inner wall, a recessed surface disposed at a bottom edge of the inner wall, a perimeter of the recessed surface being substantially defined by a bottom edge of the inner wall, and a first and second reference mark, the first reference mark being spaced a rotational distance from the second reference mark such that the rotational distance corresponds to predetermined vertical distance along the threaded engagement. An o-ring may be interposed between the top of the handpiece and the perimeter wall of the handpiece.

The device may also be configured to include an elastomeric septum, the elastomeric septum being configured to be pierced by the tool and to substantially self-seal when the tool is removed such as to substantially prevent a vacuum leakage from the recessed area when a vacuum is supplied to the recessed area. Other aspects may include the device comprising a support arm having a guide pin, the tool being mounted to the support arm, wherein the guidance track operably connected to the handpiece includes the guidance track being disposed on a surface of the top of the handpiece and slidably receiving the guide pin, the guidance track facilitating movement of the pin and support arm along the predetermined path.

In a yet further aspect, the tool is an elongate RF cutting probe. In this aspect, the device may further include an RF generator operably connected to and supplying a power to the RF cutting probe, and a circuit for measuring the impedance of a tissue disposed within the recessed area, wherein the RF generator includes a feedback control on the power supplied to the probe based on a measured impedance of the tissue such that the RF generator supplies a consistent power. In certain aspects, a temperature means on the RF cutting probe is also included. The temperature measuring means is used to communicate information indicative of a temperature of the tissue to the RF generator, wherein the feedback control stops supplying power to the RF cutting probe when a temperature of the tissue reaches a predefined threshold.

Some aspects of the device may include a vacuum fitting operably connected to one of the top and the perimeter elevation and in fluid communication with the recessed area. These aspects may also include a vacuum pump in fluid communication with the vacuum fitting, wherein the vacuum pump is configured to supply a suction force to the recessed area and configured to pull a tissue snugly and securely against the apposition surface when the recessed area is placed over the tissue.

It may also be desirable is some aspects to use the device to inject a fluid. In some aspects, the tool may be a needle, and the device may further include a pump and a source of injectable fluids in fluid communication with the pump, wherein the needle is in fluid communication with the pump, and the needle is configured to inject the injectable fluids into a tissue disposed in the recessed area. In certain aspects, the needle may include a lumen, a tip for piercing a dermis, and at least two injection ports in communication with the lumen, wherein the ports are linearly disposed along an outer surface of the needle. In some aspects, the ports may be flush with a side of the needle. The ports may be configured to discharge a fluid in a direction substantially orthogonal to an axis of the needle and substantially parallel to the top of the handpiece. Some aspects of the foregoing may further include a microprocessor having a graphical user interface, wherein the pump is configured to communicate information specifying a volume of a fluid injected into the tissue to the microprocessor. The microprocessor can be configured to use the graphical user interface to prompt a user to enter information specifying at least one of a concentration of a component of the fluid and a weight of the patient, and the microprocessor can include logic for determining a maximum dosage of the fluid injected based on the weight of the patient, the concentration of the component of the fluid, and the volume of the fluid injected. In some aspects, the microprocessor is configured to cause the graphical interface to display at least one warning message when the volume of the fluid injected exceeds a predefined threshold which is less than the maximum dosage, and may also be configured to instruct the pump to terminate an injection when the volume of the fluid injected reaches the maximum dosage. In further aspects, the graphical user interface may be configured to enable the user to over-ride the maximum dosage such that the pump continues to inject the fluid once the maximum dosage has been reached. In yet further aspects, the microprocessor may be configured to track an amount of elapsed time since the pump initiated pumping the fluid and to calculate a recommended treatment end time using information selected from a group consisting of the volume of fluid injected and the elapsed time. In certain aspects including a vacuum pump, the vacuum pump may be configured to communicate with the microprocessor and the graphical user interface to display an elapsed amount of time a vacuum was supplied to the handpiece by the vacuum pump. The vacuum pump may also be, in some aspects, configured to communicate with the microprocessor and the graphical user interface to display a vacuum pressure. It is not necessary that these aspects regarding injection of a fluid and microprocessor control be limited a device wherein the tool is a needle, but it may also be desirable to include these aspects and/or limitations in any of the aspects herein described.

Also disclosed is a method of performing subcutaneous surgery, the method comprising the steps of (1) providing a handpiece having a perimeter elevation and a top which cooperatively define a recessed area, an inner side of the perimeter elevation and top defining a tissue apposition surface facing into the recessed area, and a conduit extending through a side of the perimeter elevation into the recessed area; (2) positioning the handpiece over a first treatment area located on a dermis; (3) applying a force to the handpiece to move a portion of the dermis into the recessed area to substantially fill the recessed area, such that a portion of the dermis is in contact with a substantial area of the tissue apposition surface and a subcutaneous tissue is disposed in the recessed area; (4) inserting a distal end of a tool through the conduit and through the dermis and into the subcutaneous tissue; and, (4) guiding the tool along a predetermined path of a guidance track to move a distal end of the tool in a plane parallel to the top of the handpiece and within the recessed area, to create a surgical lesion of a predetermined shape defined by the predefined path.

In certain aspects, the method may also include moving the distal end of the tool in an x and y direction along the plane parallel to the top of the handpiece. Certain aspects may also include providing a vacuum assisted suction force to the recessed area to move the dermis into the recessed area.

The method may include adjusting a height of the top of the handpiece in relation to an entry point of the conduit within the recessed area to adjust the volume of the recessed area and a depth of the subcutaneous tissue accessible by the tool when inserted through the conduit. In some aspects, the top includes a reversible lid, and the height is adjusted by disconnecting the reversible lid from the handpiece, turning it over, and reconnecting it to the handpiece. Some aspects of adjusting a height of the top of the handpiece may include rotating the top of the handpiece with respect to the perimeter elevation along a threaded engagement between the top of the handpiece and the perimeter elevation of the handpiece. In other aspects, the top of the handpiece may include a rigid upper lid and a rigid lower lid, the rigid upper lid being fixed with respect to the perimeter elevation, wherein adjusting a height of the top of the handpiece includes inflating a bladder disposed between the rigid upper lid and rigid lower lid to move the rigid lower lid up and down with respect to a wall of the perimeter elevation, the rigid inner lid being at its lowest point when the bladder is fully expanded and being at its highest point when the bladder is deflated.

Some aspects of the method may include the further steps of (a) removing the distal end of the cutting device from the subcutaneous tissue; (b) positioning the handpiece over a second treatment area located on the dermis, wherein the second treatment area is proximal the first treatment area; (c) applying a force to the handpiece to move a portion of the second treatment area of the dermis into the recessed area to substantially fill the recessed area, such that a portion of the second treatment area of the dermis is in contact with a substantial area of the tissue apposition surface and a second layer of subcutaneous tissue is disposed in the recessed area; (d) inserting a distal end of a tool through the conduit and through the dermis and into the second layer of subcutaneous tissue; and (e) guiding the tool along the predetermined path of the guidance track to move the distal end of the tool in the plane parallel to the top of the handpiece and within the recessed area, to create a second surgical lesion of the predetermined shape defined by the guidance track. In some aspects, the second treatment area may also at least partially overlap the first treatment area, and/or adjusting a height of the top of the handpiece in relation to an entry point of the conduit within the recessed area to change the volume of the recessed area and a depth of the subcutaneous tissue accessible by the tool.

In some aspects of the method, the tool is an elongated RF, laser, ultrasound, or thermal probe, and creating a surgical legion includes applying one of a RF energy, laser energy, ultrasound energy and heat to ablate a portion of the subcutaneous tissue. In further aspects, the portion of the subcutaneous tissue may include adipose tissue, or, include fibrous septae and creating a surgical legion includes cutting the fibrous septae. In some aspects, the tool is a catheter having a high-pressure fluid jet, and wherein the method of creating a surgical legion includes injecting a fluid at a high pressure and parallel to the top of the handpiece to displace a portion of the subcutaneous tissue.

Embodiments of the invention may enable the use of a variety of cutting, coagulation and hemostasis means by a physician.

Electrocautery encompasses passing electrical current through a tool to raise its temperature and using the hot tool to seal blood vessels and induce coagulation. If the tool is equipped with a sharp edge or other cutting mechanism, cutting and coagulation may be performed simultaneously. Because of the high level of conductive hear transfer an extensive heat-affected tissue zone may be created.

In radiofrequency electrosurgery a current is run from a surgical tool to a counter-electrode outside the patient, and the current actually runs through the patient instead of through the tool. Due to the high resistance at the tool-tissue interface a local heat zone develops, but because of the low levels of conductive heat transfer the heat zone may be in the sub-millimeter range. By modulating the applied voltage from a "cutting" setting to a "coagulation" setting a physician may select from a range of operating modes defined by these two modalities.

These and other tools currently available in medical practice allow a physician to select from a wide variety of treatment options and tailor a treatment to specific patient needs. The functionality of embodiments of the invention may be independent of the type of surgical tool selected by the physician. Therefore, embodiments of the invention may enable a physician to select an optimal treatment for the patient and the specific disease condition from the available cutting and coagulation tools, without limitations due to the embodiment of the invention used to implement the procedure.

In some aspects, the handpiece has perimeter elevation and a top which cooperatively define a recessed area; and a vacuum conduit extending through a side of the perimeter elevation to the recessed area. In some aspects the vacuum conduit can be connected to a vacuum device.

Also disclosed are methods for performing subcutaneous surgery in a region underlying skin tissue having a deformity, comprising positioning a handpiece having a recessed area over a section of skin, reducing air pressure inside the recessed area to move a portion of the section of skin and a subcutaneous tissue into the recessed area, inserting a lesion creation tool through a conduit in the handpiece and through the section of skin into the subcutaneous tissue, and creating a lesion in the subcutaneous tissue, wherein the deformity is selected from a scar, a wrinkle, and a surface irregularity resulting from liposuction, and following creation of the lesion an appearance of the deformity is improved.

Also disclosed are methods for performing subcutaneous surgery wherein creating a lesion comprises dissecting tissue.

Also disclosed are methods for performing subcutaneous surgery wherein creating a lesion comprises ablating tissue.

Also disclosed are methods for performing subcutaneous surgery further comprising maintaining reduced air pressure in a recessed area of a handpiece after creating a lesion for a period of time determined by a physician.

Also disclosed are methods for performing subcutaneous surgery, wherein subcutaneous tissue comprises a fibrous septum, and wherein creating a lesion comprises severing the fibrous septum.

Also disclosed are methods for performing subcutaneous surgery in a region underlying skin tissue having a scar, wherein the scar is an atrophic scar.

Also disclosed are methods for performing subcutaneous surgery in a region underlying skin tissue having an atrophic scar, wherein the atrophic scar is an acne scar.

Also disclosed are methods for performing subcutaneous surgery, wherein creating a lesion is directed at improving a distribution of fat underlying a section of skin.

Also disclosed are methods for performing subcutaneous surgery in a region underlying skin tissue having a previously closed wound, comprising positioning a handpiece having a recessed area over a section of skin comprising the previously closed wound, reducing air pressure inside the recessed area to move a portion of the section of skin and a subcutaneous tissue into the recessed area, inserting a lesion creation tool through a conduit in the handpiece and through the section of skin into the subcutaneous tissue, and creating a lesion in the subcutaneous tissue, wherein following creating the lesion scar formation associated with healing of the wound is reduced.

Also disclosed are methods for performing subcutaneous surgery, wherein creating a lesion relieves local tension in tissue adjacent to a previously closed wound.

Also disclosed are methods for performing subcutaneous surgery in a region underlying skin tissue affected by hyperhidrosis, comprising positioning a handpiece having a recessed area over a section of skin affected by hyperhidrosis, reducing air pressure inside the recessed area to move a portion of the section of skin and a subcutaneous tissue into the recessed area, inserting a lesion creation tool through a conduit in the handpiece and through the section of skin into the subcutaneous tissue, and creating a lesion in the subcutaneous tissue wherein following creation of the lesion the hyperhidrosis is inhibited.

Also disclosed are methods for performing subcutaneous surgery, wherein a section of skin overlies at least one sweat gland.

Also disclosed are methods for performing subcutaneous surgery, wherein creating a lesion comprises dissecting the sweat gland.

Also disclosed are methods for performing subcutaneous surgery, wherein creating a lesion comprises thermally ablating the sweat gland.

Also disclosed are methods for performing subcutaneous surgery, wherein creating a lesion comprises chemically ablating the sweat gland.

Also disclosed are methods for performing subcutaneous surgery, wherein a section of skin overlies at least one efferent nerve to a sweat gland.

Also disclosed are methods for performing subcutaneous surgery, wherein creating a lesion comprises dissecting the nerve.

Also disclosed are methods for performing subcutaneous surgery, wherein creating a lesion comprises thermally ablating the nerve.

Also disclosed are methods for performing subcutaneous surgery, wherein creating a lesion comprises chemically ablating the nerve.

Also disclosed are methods for performing subcutaneous surgery to create a lesion for a subcutaneous tissue pocket for introducing a substance, comprising positioning a handpiece having a recessed area over a section of skin, reducing air pressure inside the recessed area to move a portion of the section of skin and a subcutaneous tissue into the recessed area, inserting a lesion creation tool through a conduit in the handpiece and through the section of skin into the subcutaneous tissue, and creating the lesion in the subcutaneous tissue.

Also disclosed are methods for performing subcutaneous surgery to create a lesion for a subcutaneous tissue pocket for introducing a substance, further comprising introducing the substance into the tissue pocket.

Also disclosed are methods for performing subcutaneous surgery, wherein the substance comprises at least one of a medical device, a drug, a biologic and a combination product.

Also disclosed are methods for performing subcutaneous surgery, wherein the substance comprises a non-regulated component.

Also disclosed are methods for treating a previously formed subcutaneous lesion created to sever a subcutaneous fibrous septum, the method comprising positioning a handpiece having a recessed area over a section of skin overlying the lesion, reducing the air pressure inside the recessed area to move a portion of the section of skin and a subcutaneous tissue into the recessed area, and maintaining reduced air pressure for a pre-determined period of time.

Also disclosed are methods for treating a previously formed subcutaneous lesion created for improving an appearance of a feature in a section of skin overlying the lesion, the method comprising positioning a handpiece having a recessed area over the section of skin overlying the lesion, reducing the air pressure inside the recessed area to move a portion of the section of skin and a subcutaneous tissue into the recessed area, and maintaining reduced air pressure for a pre-determined period of time; wherein the appearance of the feature is improved relative to the appearance of the feature prior to maintaining the reduced air pressure.

Also disclosed are methods for treating a previously formed subcutaneous lesion created for improving an appearance of a feature in a section of skin overlying the lesion, wherein the feature comprises an atrophic scar.

Also disclosed are methods for treating a previously formed subcutaneous lesion created for improving an appearance of a feature in a section of skin overlying the lesion, wherein an atrophic scar is an acne scar.

Also disclosed are methods for treating a previously formed subcutaneous lesion created for improving an appearance of a feature in a section of skin overlying the lesion, wherein the feature comprises a wrinkle.

Also disclosed are methods for treating a previously formed subcutaneous lesion created for improving an appearance of a feature in a section of skin overlying the lesion, wherein the feature comprises a skin surface irregularity caused by liposuction.

Also disclosed are methods for treating a previously formed subcutaneous lesion created for reducing scar formation associated with healing of a previously closed wound, the method comprising positioning a handpiece having a recessed area over a section of skin comprising the previously closed wound, reducing the air pressure inside the recessed area to move a portion of the section of skin and a subcutaneous tissue into the recessed area, and maintaining reduced air pressure for a pre-determined period of time; wherein the scar formation is reduced.

A method for treating a previously formed subcutaneous lesion created for dissecting sweat glands to treat hyperhidrosis, the method comprising positioning a handpiece having a recessed area over a section of skin overlying the lesion, reducing the air pressure inside the recessed area to move a portion of the section of skin and a subcutaneous tissue into the recessed area, and maintaining reduced air pressure for a pre-determined period of time; wherein healing of the sweat glands is inhibited.

A method for treating a previously formed subcutaneous lesion created for dissecting nerves innervating sweat glands to treat hyperhidrosis, the method comprising positioning a handpiece having a recessed area over a section of skin overlying the lesion, reducing the air pressure inside the recessed area to move a portion of the section of skin and a subcutaneous tissue into the recessed area, and maintaining reduced air pressure for a pre-determined period of time; wherein healing of the nerves is inhibited.

BRIEF DESCRIPTION OF THE DRAWINGS

FIGS. 6A and 6B depict the handpiece used in connection with a removable guidance track.

FIG. 7 depicts a perspective view of the handpiece and motor controlled cutting mechanism used in connection with the method.

FIGS. 9A through 9C depict configuration and placement of the handpiece on a dermis of a patient and an alternate embodiment of the guidance track.

FIG. 15 depicts a microprocessor and display for use with the embodiments.

FIG. 16A depicts an embodiment of the cutting device, including an RF cutter.

FIG. 16B depicts a block diagram of system, including the handpiece and RF cutting tool.

FIG. 18 depicts an embodiment of a cutting tool.

FIGS. 19A through 19C depict embodiments of the cutting tool with one or more retractable blade members.

FIGS. 24A through 24F depict a second embodiment of a mesh deployment applicator, including a deployment shaft and keeper rod.

FIG. 25 depicts a cut-away side view of the handpiece in use with the mesh deployment applicator.

FIGS. 26A and 26B depict the handpiece and guidance track for use with a fluid injection device.

FIG. 28A depicts one embodiment of a dissection device used in a method for severing an endocrine sweat gland and FIGS. 28B-28D depict flowcharts of methods to perform subcutaneous surgery.

FIGS. 30A-30D depict a method to treat acne scars.

FIGS. 38A-38E depict a method for creating a subcutaneous pocket and the placement of an implant.

DETAILED DESCRIPTION OF THE PREFERRED EMBODIMENTS

Figure 1A:
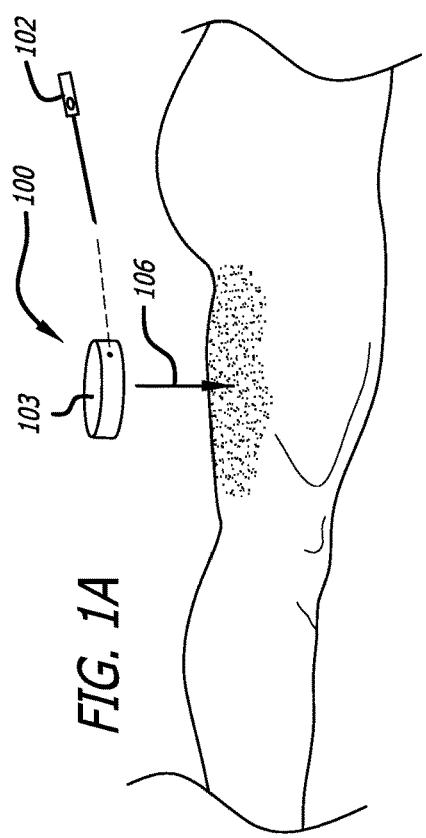
FIGS. 1A through 1C depict a dissection device, including a handpiece and a cutting tool.

In general, the device and methods described here are used to minimally invasively create a planar dissection at a defined depth below the dermis. In particular, the plane of dissection may be created generally parallel to and at a predefined depth below the dermis. Alternatively a plane of dissection may be created at an angle or in a curved shape relative to the surface of the dermis. Throughout this application reference to a depth below the dermis or the like should be understood to refer to a depth measured orthogonally from the exterior surface of the skin. In addition, the term "planar dissection" may mean that the surface of the dissection lies within a single plane, but alternatively may mean that the surface of dissection lies in multiple planes or has a curvature, e.g. a cylindrical or spherical shape, or other geometry extending across an area beneath the skin such that an upper layer closer to the skin surface is separated from a lower layer by the planar dissection. It should also be noted that the utility of the devices disclosed extends beyond treatment of the specific anatomical structures or physiological conditions described here.

The device and methods may additionally be used to enlarge the tissue pocket created by the dissection by applying a vacuum assisted suction force to the handpiece during the performance of the dissection and lifting the skin after the dissection is completed. Application of vacuum on the skin during the dissection process may put traction on the underlying tissues, may better align the fibrous septae for dissection with the cutting tool, and may allow for uniform and instantaneous separation of the dissected tissue layers. Additionally, devices and methods are disclosed for applying vacuum to a skin area overlying treated subcutaneous tissue after creation of the dissection.

According to some embodiments it may also be desirable to employ energy such as Radiofrequency (hereinafter "RF"), to provide the dissection means. The energy can be configured to provide coagulation or a controlled thermal injury, which in turn may provide fat cell damage/shrinkage or create a more fibrous layer directly or through wound healing processes. Thermal energy may particularly enhance the effect of the treatment where tissue destruction or ablation is desirable. Embodiments of the invention may allow a physician to select from a range of tools that are capable of creating dissections, achieving coagulation and hemostasis or a combination of these treatment modalities, thereby enabling the physician to tailor the treatment to the individual patient without limitations due to the embodiment of the invention used to implement the procedure.

If desired, a fluid may be injected into the pocket created by the dissection. The fluid may be actively injected, for instance by using a syringe, or may be drawn into the pocket from an external reservoir by the reduced pressure created by a vacuum applied to the handpiece. The fluid may perform a number of functions, including enlarging the subcutaneous tissue pocket, providing structural support, and affecting the biological response to the procedure by means of an active pharmaceutical ingredient (API).

It should be understood the term "may" as used throughout the specification refers to an optional feature or component.

Figure 1B:
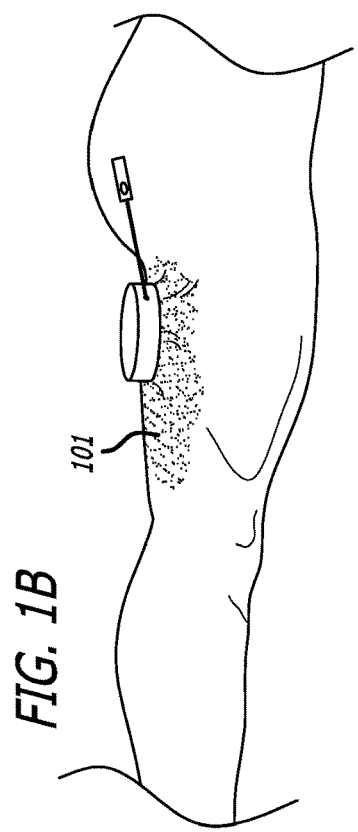
Figure 1C:
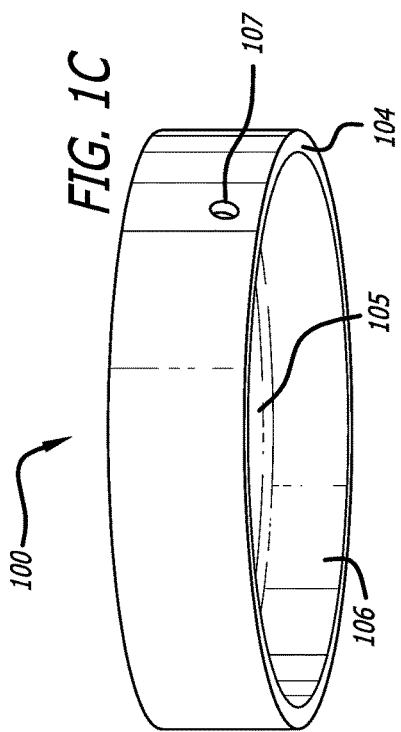

As illustrated by FIGS. 1A through 1C, the embodiments utilize a handpiece 100 to capture and control a location of the skin, or dermis 101, as well as precisely control use of a cutting tool 102. The handpiece preferably has a top 103 and a perimeter elevation 104 that cooperatively define a recessed area 105 which can be placed over the dermis of a patient. By applying a force 106 to the top of the handpiece or by a vacuum supplied to the handpiece, a portion of the dermis 101 can be moved into the recessed area to substantially fill the recessed area, thus capturing it within the handpiece and providing some control over the area of tissue captured. This allows a distal portion of cutting tool 102 or other suitable dissection device to be inserted through a conduit 107 extending through a side of the perimeter elevation of the handpiece, percutaneously through the tissue disposed in the recessed area, and into the subcutaneous tissues encompassed by the recessed area of the handpiece. Cutting tool 102 is maneuvered in such a way as to cut a surgical lesion of a predetermined shape inside the subcutaneous tissues within the recessed area and parallel to the top of the handpiece. The surgical lesion (dissection) is targeted to be in a range from as shallow as at 1 mm to 2 mm below the interface between the dermis and the shallow fat, to as deep as 20 mm below the skin/fat interface. Applicants hereby define percutaneous to mean a puncture or incision through the skin of between 0.4 mm and 4.0 mm. It should be understood that handpiece 100 may be used in conjunction with any of the dissection devices disclosed herein.

Figure 2A:
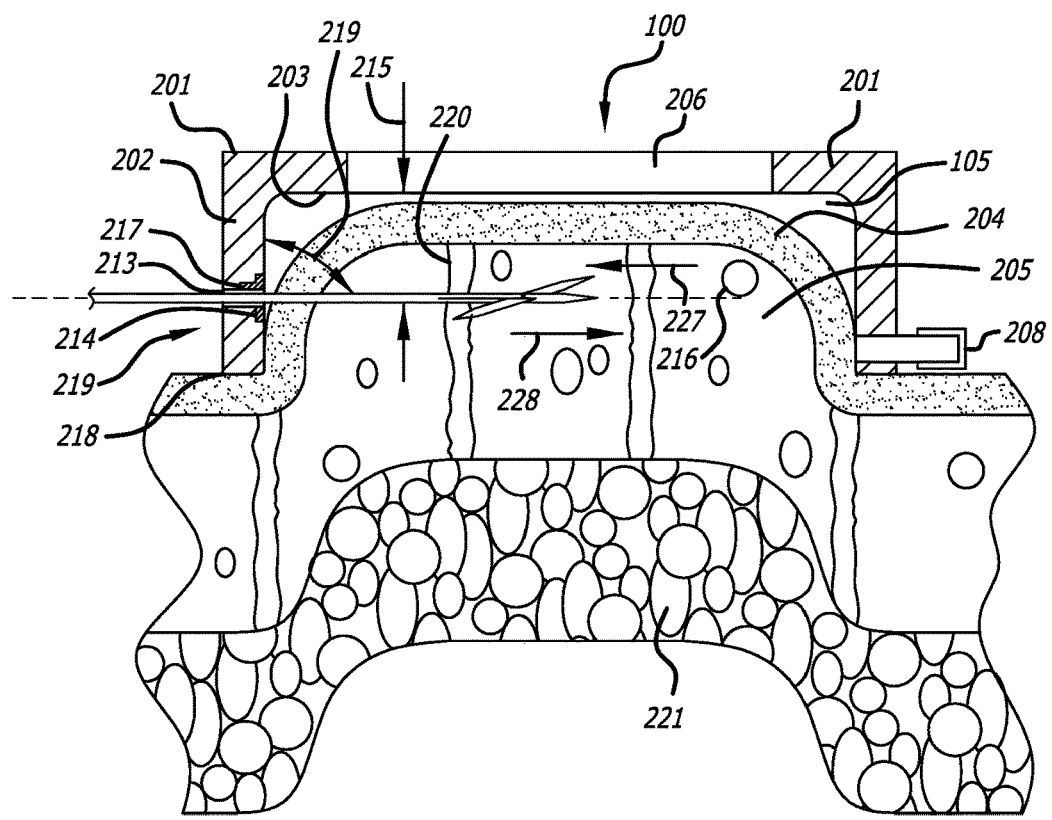
FIGS. 2A and 2B depict a cut-away side view and perspective view of the handpiece used in conjunction with a cutting tool.

Turning to FIG. 2A, a top wall 201 and perimeter wall 202 define a tissue apposition surface (tissue facing surface) 203 facing into recessed area 105. Tissue apposition surface 203 may be curved inward to the handpiece, or concave, or recessed, so that when handpiece 100 is disposed against an epidermis 204, further pressure against the handpiece 100 will cause the handpiece to encompass a subcutaneous level of tissue 205, particularly the subdermal tissue layer below the epidermis and dermis layers, wherein these layers will be positioned within recessed area 105. In some embodiments tissue apposition surface 203 includes perimeter wall 202 as a relatively small inner wall around the perimeter of recessed area 105. In some embodiments, handpiece 100 may include a transparent cover 206 so that a physician can clearly see and verify that the dermis is properly positioned within the dissection region. In the depicted embodiments, the perimeter walls (sidewalls) of the handpiece are shown generally circular. However, one of ordinary skill in the art will appreciate that the handpiece can be any shape.

The device further allows for three-dimensional control of treatment or anesthetic fluid delivery and dissection of subcutaneous tissues, not realized by present art. The device typically controls a depth 215 of between 4 mm and 20 mm below the surface of skin (measured orthogonally from the dermis); but a depth less than 4 mm or greater than 20 mm is also contemplated. Depth 215 is generally defined as being measured from tissue apposition surface 203. For the purpose of this disclosure, however, the measurement is taken when epidermis 204 is flush against apposition surface 203 and the thickness of epidermis is considered negligible. As such, depth 215 can also be considered to be a depth below the surface of the skin or a depth below epidermis 204. The range of motion in the lateral direction is controlled by the length and movement of the cutting blade and/or RF probe, however, typically encompasses a length of between 2 mm and 100 mm in either direction. As the needle/blade/probe is disposed further into the skin larger arcs are achieved.

Generally, device 100 is pressed against the tissue to move the subcutaneous layer 205 into recessed area 105 and against tissue apposition surface 203. In some embodiments, vacuum (suction) is used to enhance the capture of the tissue. A vacuum source 1606 (FIG. 16B) may be placed in fluid connection with handpiece 100 via an optional vacuum port 208 on handpiece 100. The vacuum source may include a vacuum pump in fluid communication with recessed area 105. Vacuum pump 1606 supplies suction to the recessed area to pull tissue snugly and securely therein. In some embodiments, the vacuum pump is configured to communicate with a microprocessor 1501 (e.g., FIG. 15) and the graphical user interface 1502 to display a vacuum pressure. The system may further include a display indicating the elapsed amount of time vacuum was supplied to the handpiece by the vacuum pump. The vacuum pump may also modulate the suction such that a higher suction force is applied initially to pull the tissue into the recess, and a somewhat lower suction force is used to maintain/hold the tissue in place thereafter.

Vacuum port 208 may be located in the top wall 201 and/or the perimeter wall 202 of handpiece 100. In some embodiments, tissue apposition surface 203 includes two or more vacuum ports 208 disposed on its surface and configured to apply suction from the vacuum source to the recessed area and to the tissue from different locations of the handpiece.

Figure 2B:
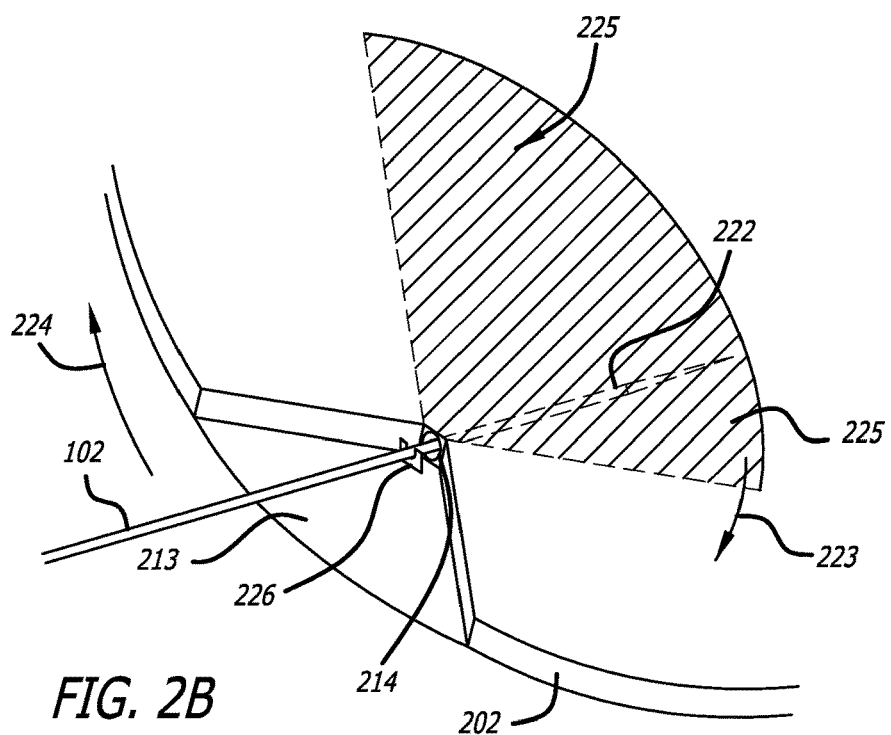

In the embodiment depicted by FIG. 2A, handpiece 100 is seen in use with a vacuum pressure (suction) applied to a portion of skin 101. Suction applied at vacuum port 208 causes skin 101 to be pulled up into contact with apposition surface 205 of handpiece 100. By applying a sufficient suction force, a portion of epidermis 204 is pulled into the chamber of vacuum handpiece 100 and conforms to inner recessed area 105. While the surface of the skin 204 is tightly positioned against top wall 201 and perimeter wall 202 of recessed area 105, fat layer 205 (subcutaneous tissue) is also drawn into the chamber. A cutting tool 102 (e.g., a cutting blade or RF probe, or needle), can be inserted through a conduit 213 in a side of handpiece 100 and through entry hole 214, through the skin, and into the subcutaneous tissue. Significantly, the handpiece enables the cutting tool to be consistently inserted at desired treatment depth 215. Handpiece 100 thus provides for precise control of the depth of the dissection plane and allows for cutting and/or movement of tool 102 substantially parallel to the surface of the tissue along a plane 225 (FIG. 2B).

A membrane 217 formed of a flexible and resilient material may also be applied to the perimeter wall (sidewall) across the proximal (away from the recessed area) or distal ends (closer to the recessed area) of the conduit 213 to minimize vacuum leakage there through. The membrane 217 preferably is sufficiently resilient to seal around the cutting tool as it pierces (self-sealing) therethrough and minimize vacuum leakage. Membrane 217 may be formed of silicone. However, one of ordinary skill in the art will appreciate that other materials may be use to create the self-sealing membrane.

Conduit 213 is disposed in sidewall 202 of handpiece 100, preferably, adjacent bottom or side portion of tissue apposition surface 203. In some embodiments conduit 213 is a through hole defined in perimeter wall 202 or in top wall 201. In other embodiments, conduit 213 is a tube-like member inserted into and/or mounted to a through hole in the perimeter or top wall. Conduit 213 is configured to allow passage of a hypodermic needle, subdermal catheter, cutting tool (as described above), insertion tool, or other appropriately configured tool through the conduit and into recessed area 105 of the device. The tool may pass through conduit 213 just enough to penetrate the tissue.

Conduit 213 is preferably located proximate a bottom edge 218 of perimeter wall (sidewall) 202 to allow a cutting tool or needle to be inserted into the tissue (captured in the recessed area) in a plane parallel to the dermis. In some embodiments conduit 213 supplies an angle of penetration 219 so that the tool inserted through the conduit will penetrate into tissue disposed within the recessed area, and substantially parallel to the surface of the tissue and parallel to the surface of top wall 201 at depth 215. Specifically, this configuration may provide stability of the tool to maintain an even level, e.g., when the cutting tool is cutting the fibrous structures 220 between the epidermis 204 (and dermis) and the subdermal fat 221. In some embodiments, conduit 213 provides an angle of entry to bias the plane of dissection toward or away from the dermis.

As depicted in FIG. 2B, entry hole 214 is preferably disposed on an inner side of the conduit and facing the recessed area. Conduit 213 preferably widens outward toward an outer side of the perimeter elevation such that a distal end 222 of the cutting tool inserted through the entry hole moves in one direction 223 when a proximal end of the cutting tool outside the conduit moves in an opposite direction 224. Entry hole 214 thereby defines a cutting tool pivot point when a distal end 222 of cutting tool 102 is inserted through conduit 213 and into recessed area 105, and the tool moves primarily in an x-y plane 225 parallel to the top surface of the handpiece. In some embodiments entry hole 214 may include an optional locking mechanism 226 that locks the tool in place upon insertion into the conduit. In some embodiments in which a vacuum is supplied to the recessed area, an optional gasket or seal 217 (not shown in FIG. 2B) may be placed within, in front of, behind, or around entry hole 214 to minimize vacuum leakage.

In some embodiments conduit 213 constrains side-to-side movement of a tool such that movement of the tool through the conduit is limited to a backward direction 227 and forward direction 228. In some embodiments conduit 213 constrains upward and downward movement of a tool such that movement of the tool to maintain the tool in a plane parallel to the surface of the skin 225. In other embodiments, conduit 213 is configured to allow the cutting tool to be moved in an arc 223 parallel to the recessed area of the tissue facing (apposition) surface so as to allow cutting within a subdermal area substantially the size of the recessed surface area.

In some embodiments, conduit 213 has a tool control mechanism (not shown) which allows cutting tool 102 or other tool appropriately configured device, to be controlled by a microprocessor. In such an embodiment handpiece 100 and/or the microprocessor (not shown) controls cutting device 102 to precisely cut an area of tissue disposed within recessed area 105. The area being cut is predetermined and programmed into the microprocessor by the operator of the handpiece.

Figure 3A:
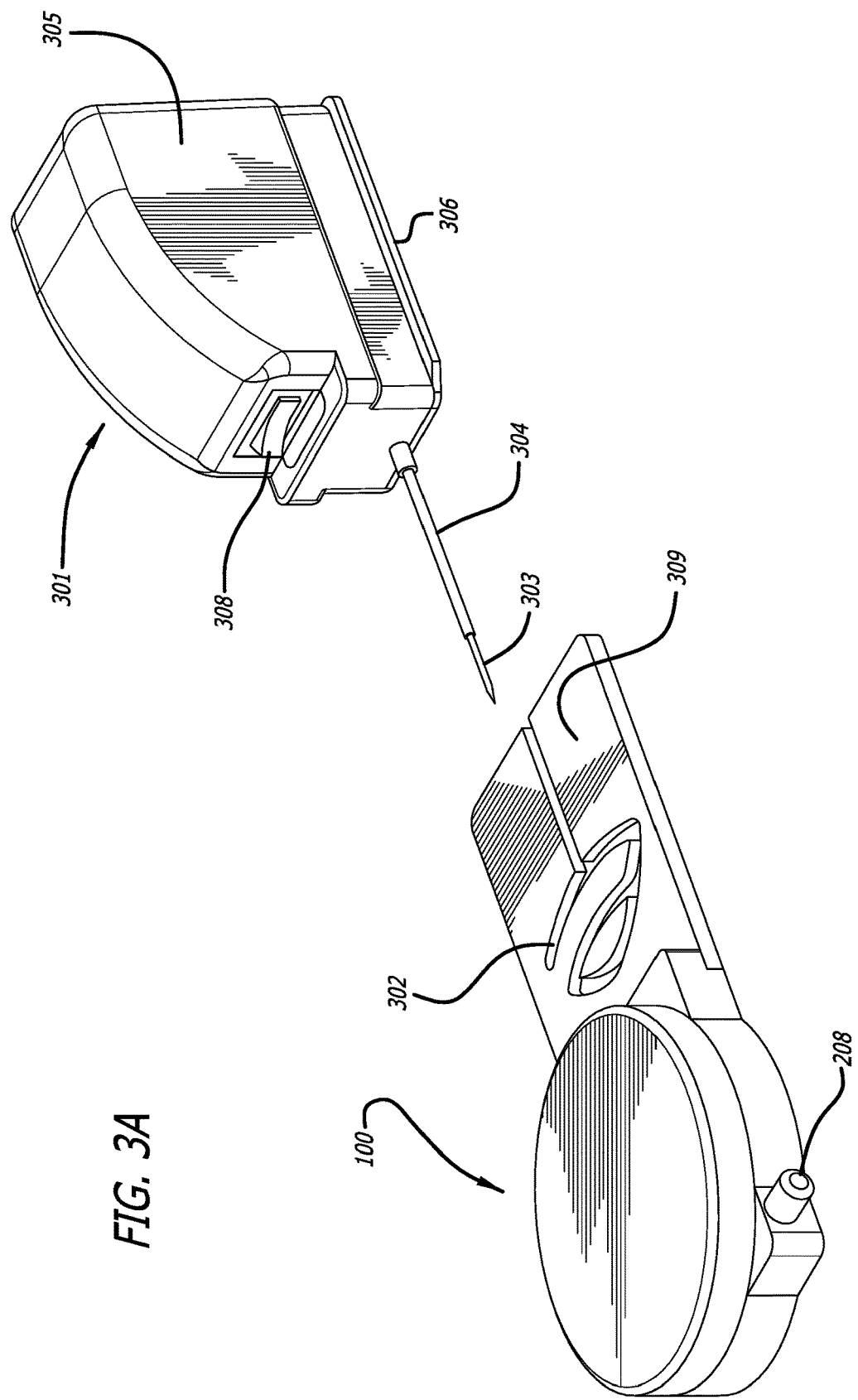
FIGS. 3A and 3B depicts a perspective view of the handpiece and motor controlled cutting mechanism.
Figure 3B:
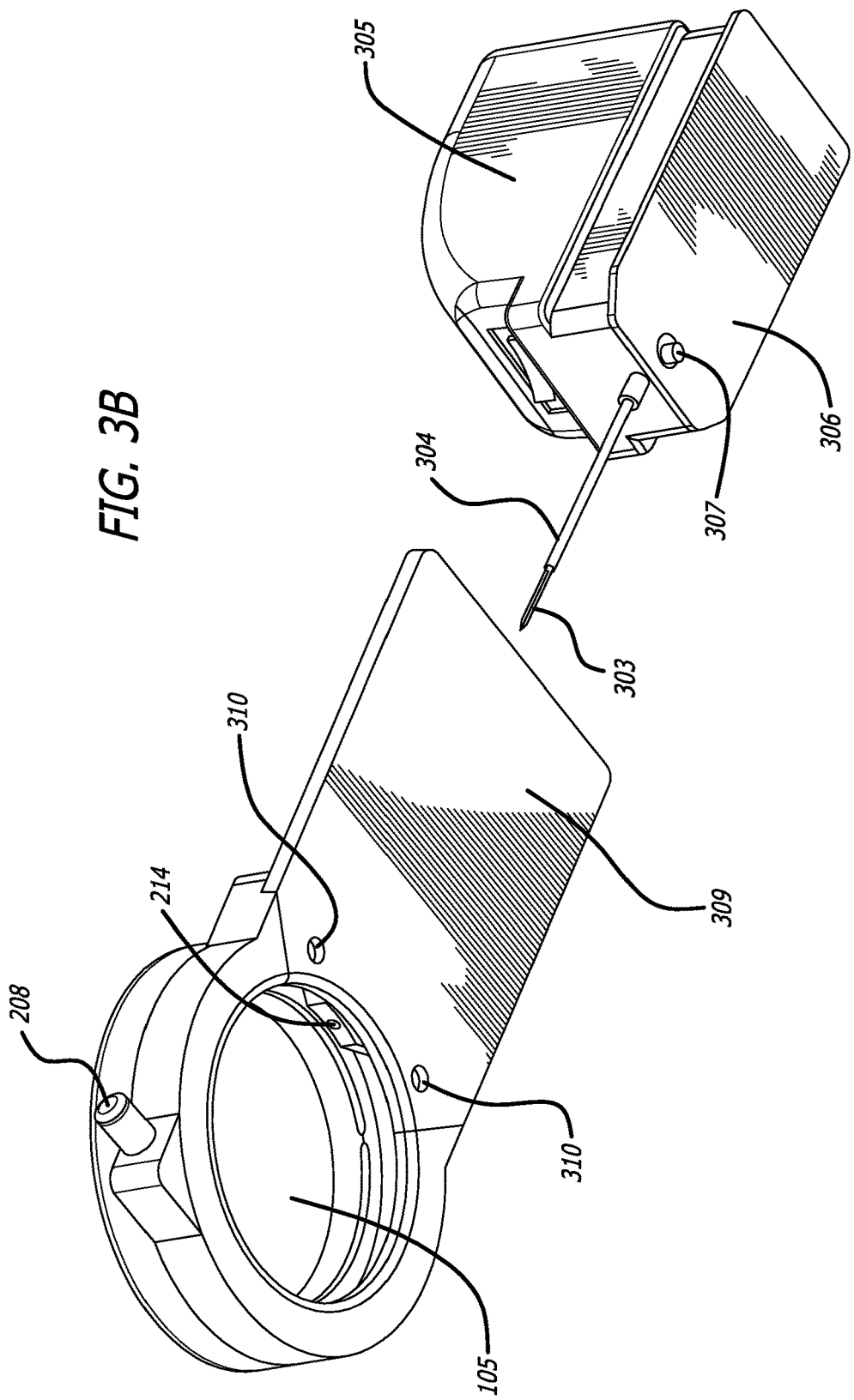

As depicted in FIGS. 3A and 3B, the dissection system may include a motor controlled cutting module 301 and a guidance 302 track operably connected to handpiece 100. In this embodiment, the cutter module includes an embodiment of cutting tool 102 (a reciprocating cutting blade 303 disposed in a sleeve 304) and a housing 305 and a base 306. Guidance track 302 is generally configured to constrain a portion of the cutting module guide pin 307 in contact with the guidance track to move along a predetermined path. Thus, a distal end of the cutting tool, passing through entry hole 214, cooperatively moves within recessed area 105 in a plane substantially parallel to the top of the handpiece and within a region of a predetermined shape defined by the predefined path. Motor operation of cutting module 301 is preferably controlled manually by an electric switch or button 308, but may also be activated by electrical or other contact means known in the art within the guidance track.

Figure 4:
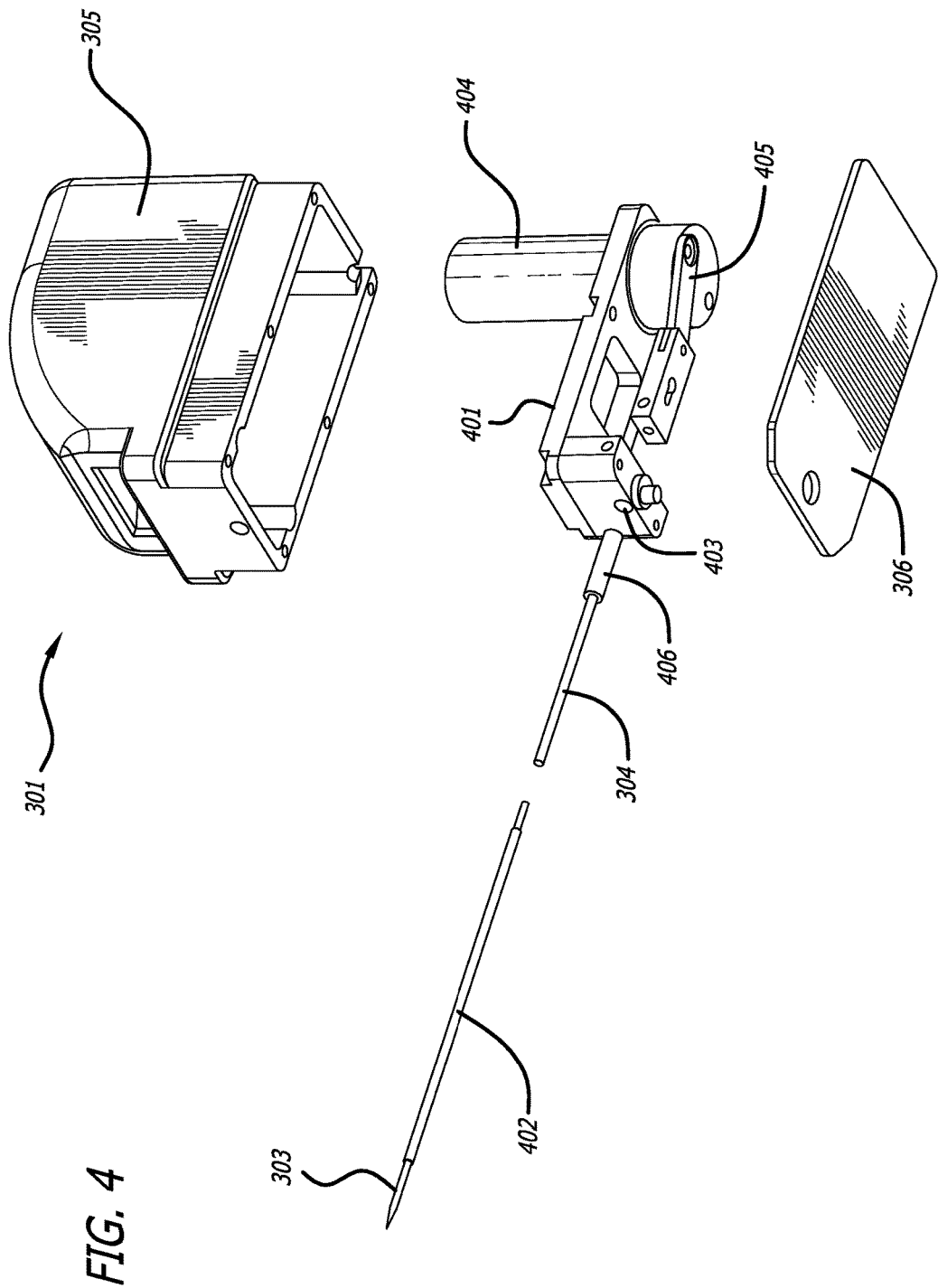
FIG. 4 is an exploded view of the motor-controlled cutting mechanism.

FIG. 4 depicts an exploded view of cutting module 301. Cutter module 301 includes housing enclosure 305 and base 306, motor assembly 401 mounted on the base and enclosed by the housing, and a reciprocating cutting blade 303 operably connected to motor assembly 401. Cutting blade 303 is slidably disposed within sleeve 304. Sleeve 304 minimizes the amount of tissue in direct contact with the shaft 402 of the cutting blade 303 to minimize drag and or tugging on the tissue. Sleeve 304 also enables the isolation and/or capture of any fluid that may travel along the shaft of blade 303.

A motor assembly 401 is enclosed in enclosure 305 and base 306. Sleeve 304 is affixed at a distal end 403 of motor assembly 401. In one embodiment, motor 404 is a DC motor which may incorporate a gear reduction. In the depicted embodiment, a crank slider 405 converts motor rotation to cutter reciprocation. However, it should be understood that other designs which convert rotary to reciprocating motion (e.g., Scotch yoke) may also be employed. Motor 404, within enclosure 305 moves reciprocating cutter blade 303 within sleeve 304. As the motor turns, crank slider 405 moves cutter 303 back and forth within sleeve 304. Cutter blade 303 may include a needle or a bayonet which may further include one or more sharp edges.

Figures 5A, 5B:
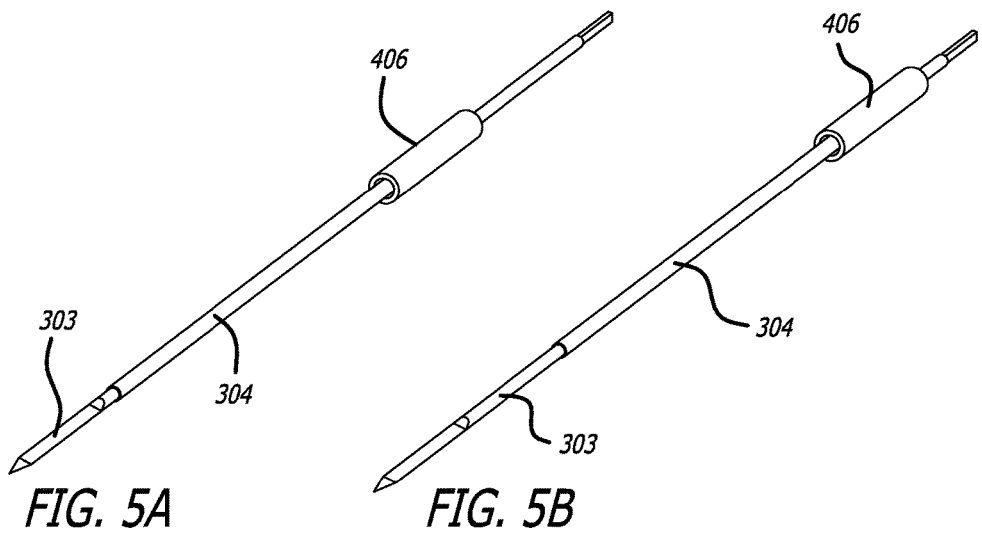
FIGS. 5A and 5B depict an enlarged view of an embodiment the cutting tool used in connection with the motor controlled cutting mechanism.

As depicted by FIGS. 5A and 5B, sleeve 304 does not reciprocate and is typically comprised of a thin-walled polymer tube and is sterile for single patient use. Sleeve 304 and cutter blade 303 are typically disposable. Sleeve 304 may be affixed to cutter module 301 (and/or crank slider 405) by means of connection point 406. Connection point 406 may be a disposable protective connector keeping cutter module 301 and gear motor assembly 401 in fluid isolation from sleeve 304 and cutting blade 303. For instance, connector 406 may also include a barrier (not shown) enclosing cutting module 301 during operation of the device. In this manner, cutting blade 303 and sleeve 304 could be disposed along with connection point 406 after each procedure. Correspondingly, cutting module 301 including motor assembly 401 and base 306 could be reused in subsequent procedures. In another embodiment, cutting blade 303, sleeve 304, and crank slider 405 may be incorporated into base 306 such that the combined assembly is separate from and operably coupled to the motor 404. In this manner the assembly could be disposed of after each procedure. Radiofrequency identification (RFID) or other interlock could prevent re-use of the blade assembly. In some embodiments cutting blade 303 is a bayonet. In other embodiments, a cutting means, such as an RF cutting device, harmonic scalpel, or similar cutting means may be substituted for or used in conjunction with the blade and/or bayonet. If an RF cutting device is used then the device is operably connected to an RF amplifier (see FIG. 16B).

Figure 12A:
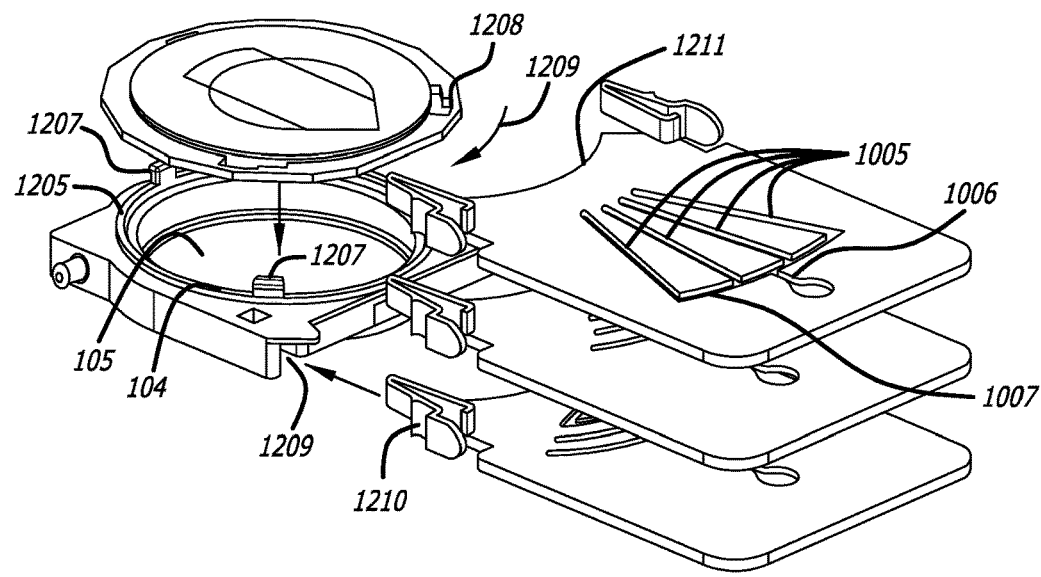
FIGS. 12A and 12B depict the handpiece with a reversible lid and an embodiment of a detachable guidance track.

With reference to FIGS. 3A and 3B, the handpiece also preferably includes a platform 309 integral with or affixed to a proximal side of handpiece 100. Platform 309 may be affixed to handpiece 100, for example, by screws 310 (e.g., Allen screws), a clip mechanism 1209, 1210 (FIG. 12), or any other similar fastening means. Platform 309 preferably includes guidance track 302, wherein guidance track 302 is used to position, guide, and support cutting module 301 by means of a guide pin 307. Guide pin 307 moves within and along the path of guidance track 301 to stabilize the cutter module at a proper position proximate to handpiece 100. FIG. 3B depicts the bottom portions of the handpiece 100 and cutter module 301. Guide pin 307 is located on a side of base 306 proximal to sleeve 304. In the depicted embodiments, guide pin 307 is an protruding feature that interfaces with, or is received by, guidance track 302; however, guide pin is defined herein to be any feature which engages guidance track 302 such as to provide a defined movement of the cutting tool along a predetermined path. For example, guide pin may be a recess or groove wherein guidance track is a raised edge or ridge along guidance track 302 so that the cutting module rides along the raised guidance track to move the cutting tool along the predetermined path.

In this embodiment, guide pin 307 protrudes through base 306 of cutter module 301, however, in other embodiments guide pin 307 may be part of base 306 or cutting module 301. The guide pin may serve dual purposes. Guide pin 307 serves to guide the disclosed cutting module embodiments to create a surgical lesion defined by the path of guidance track 302. Additionally, the guide pin may include a feature such as an enlarged head or the like which interacts with guidance track 302 and prevents cutting module 301 from being lifted off the platform 309 and/or supports cutting module 301 at a predefined planar orientation relative to platform 309. In the drawings, guidance track 302 holds cutting module 301 such that the cutter blade 303 creates a lesion parallel to tissue apposition surface 203, i.e., parallel to the dermis. However, the guidance track 302 could also hold the cutting module such that the cutting blade creates a lesion at a different predefined orientation relative to the dermis. In another embodiment, the guide pin could be motorized and assist or automate the movement of the cutting module through the guidance track.

Figure 6A:
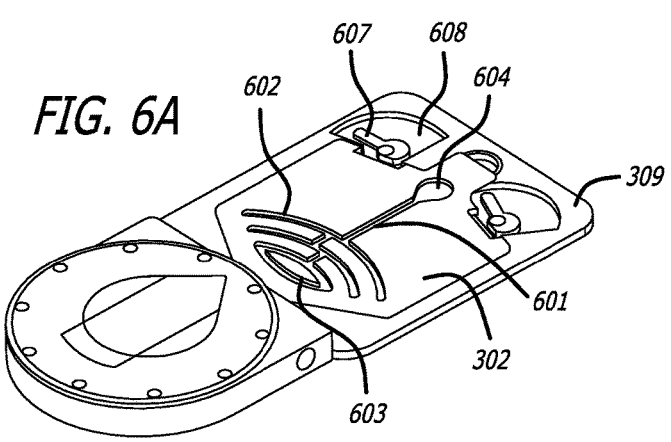

Turning now to FIGS. 6A and 6B, in one embodiment, the path of guidance track 302 is defined by a central channel 601 passing through multiple arcs 602, the arcs each having a radius measured from a center point located beyond the guidance track in a direction toward the portion of the cutting tool that will provide the cutting action. Moving toward the center point, each successive arc 602 decreases in length and grows smaller. In this embodiment, the penultimate arc is joined with a final inverted arc 603 of the same size to create a closed loop between the penultimate arc and final inverted arc. Central channel 601 does not intersect with inverted arc 603, but, rather, guide pin 307 moving along the path of central channel 601 will move into the final inverted arc by traveling along and beyond an end of the penultimate arc. In the depicted embodiment there are three primary arcs, the last joining the inverted arc. Central channel 601 also has an enlarged opening 604 at its starting position, furthest from the arcs, wherein the central channel is in the form of an elongated substantially straight track moving toward the arcs. This straightened portion allows the cutting module to be positioned within the track at its beginning and to move in a forward direction to insert the cutting tool through the conduit and entry point and into the recessed area. Central channel 601 is also staggered between the first and second arcs and between the second and third arcs to prevent a cutting module traveling along the guidance track from slipping further forward to the last arc before providing the operator of the cutting module the opportunity to move the cutting module in the entire range of the predefined path. In those embodiments in which guide pin 307 has an enlarged head, enlarged opening of the center channel is suitable for receiving the enlarged head, and guidance track 302 includes an enlarged underside for passage of the enlarged head along the path while preventing the cutting module from being lifted off platform 309 and/or supports cutting module 301 at a predefined planar orientation relative to platform 309. In an alternate embodiment, the arcs of guidance track 302 are connected at the outer edges to allow alternate movements of the cutting module between the tracks. This is particularly useful once the dissection is complete so that the motor can be easily moved from the last inverted act to central channel 601.

In alternate embodiments, with continued reference to FIGS. 6A and 6B, guidance track 302 may be removable and replaced with a different pattern which creates a different dissection profile. For instance, a variety of guidance track inserts may be provided so the physician can tailor the procedure to the patient's anatomy and/or the size of the lesion to be created. Guidance track 302 may be inserted into a predefined indentation or cutout 605 in platform 309 and constrained by a locking mechanism 606. The mechanism may include the platform having pivoting arms or levers 607 which rotate within an indentation 608 to overlap a portion of guidance track 302 to constrain it within the platform cutout. FIG. 6A depicts one embodiment of the platform having a removable guidance track 302 with a predetermined path for use with a cutting tool to cut a predetermined shape defined by the predefined path. FIG. 6B depicts an embodiment of the platform having a removable guidance track with a predetermined path for use with an injection device to coordinate movement of a complimentary device having a hypodermic needle or other injection device to inject a fluid within a tissue disposed within the recessed area in a treatment area defined by the predefined path.

Figure 12B:
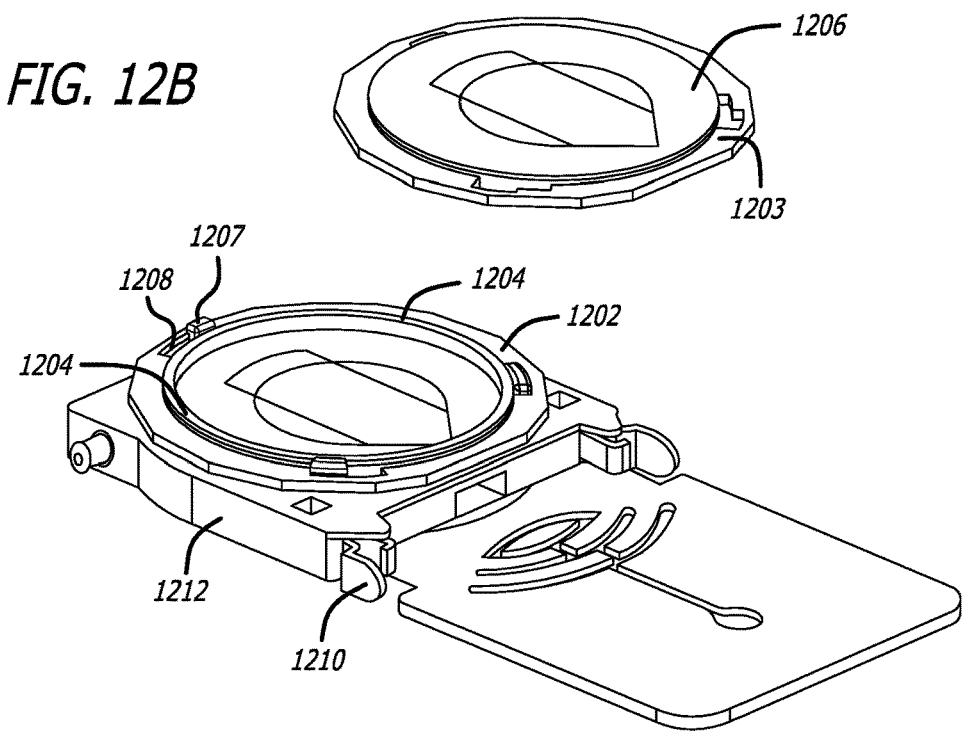

Turning briefly to FIG. 12, platform 309, including guidance track 302, may also be removably detachable from handpiece 100 by a clipping mechanism. In this embodiment, handpiece may include locking receiving spaces 1209 configured to receive complementary insertable clips 1210 affixed to platform 309. Clips 1210 may be made of a bendable material (e.g., plastic or flexible alloy) and face outward from platform 309 at its handpiece facing end 1211. Handpiece is formed such that receiving spaces 1209 are integrally formed from the body 1212 of handpiece 100, in a gap left open between the perimeter wall 104 and recessed area 104 and an outer surface of body 1212. A user wishing to attach or detach platform 309 from handpiece 100 need only cooperatively squeeze clips 1210 inward while inserting or removing them from receiving spaces 1209. Releasing clips 1210 while they are inserted in receiving spaces 1209 will lock platform 309 against handpiece 100.

FIG. 7 depicts the cutting module in use with the guidance track to cut within subcutaneous tissue.

layers 205 at depth 215. Sleeve 304 passes through entry hole 214 of handpiece 100, effectively creating a pivot at the point 801 of contact with the skin. With additional reference to FIGS. 8A through 8C, conduit 213 is wider at a point furthest from entry hole 214. This allows cutting implement 102 or cutting module 301 to pivot about entry hole 214 and move within the desired treatment area 802. Guide pin 307 on the underside of cutting module 301 is engaged into guidance track 302 of platform 309. Accordingly, the bottom of cutter module 301 remains in contact with platform 309 during operation, thus constraining the cutter to operate only in a plane at the desired depth. Engagement between pin and track, combined with pivot at shaft entry hole 214, constrains the cutter to only operate within the desired region. Guide track 302 may be constructed in any number of ways consistent with the practice of the invention. The shape of guide track 302 is not limited to those illustrated by the accompanying figures herein. In some embodiments guide track 302 may be undercut and guide pin 307 may include a flange such that the interface between the flange and the undercut prevents cutter module 301 from being lifted off from platform 309 and/or handpiece 100.

Figure 8A:
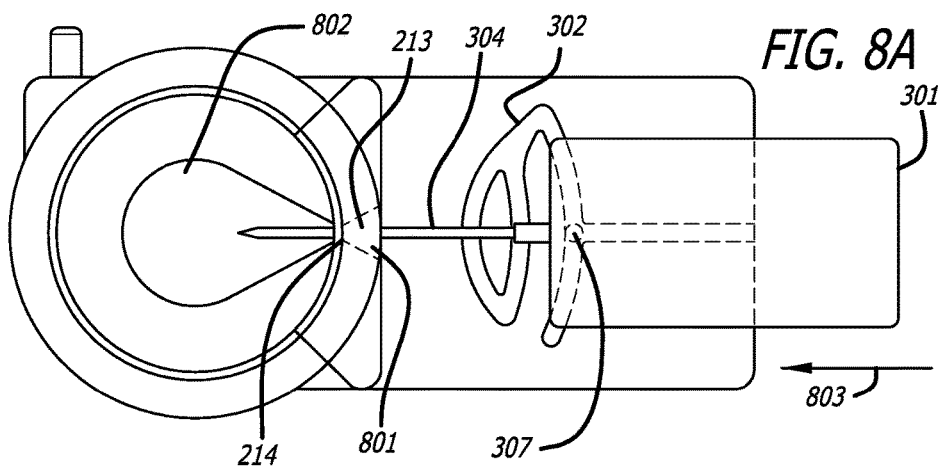
FIGS. 8A through 8C depict the operational range of the handpiece and motor controlled cutting mechanism used in connection with an embodiment of the guidance track.

Cutting region 802 is dependent upon conduit 213 such that, as cutting device 102 is constrained by entry hole 214, it is also constrained by guide pin 307 to move along guidance track 302. Accordingly, the cutting tool moves in a side to side fashion to allow a distal end of the device (including a cutting device, e.g., needle, blade, RF cutter, water jet, laser, ultrasonic or harmonic scalpel) to move along the maximum boundary (laterally and longitudinally) of cutting region 802. FIG. 8A shows the cutting blade entering into cutting region 802. Guide pin 307 is engaged in guidance track 302 as cutting module 301 is advanced in the Y direction 803 until guide pin 307 reaches the proximal arc of the track. At this point, the cutting blade is through the skin and the motor is energized to commence reciprocation of the blade. In further embodiments, the guidance track incorporates a contact (e.g., a sensor) to prevent premature powering of the motor module, or automated powering of the motor module when the motor module has reached the appropriate portion of the guidance track.

Figure 8B:
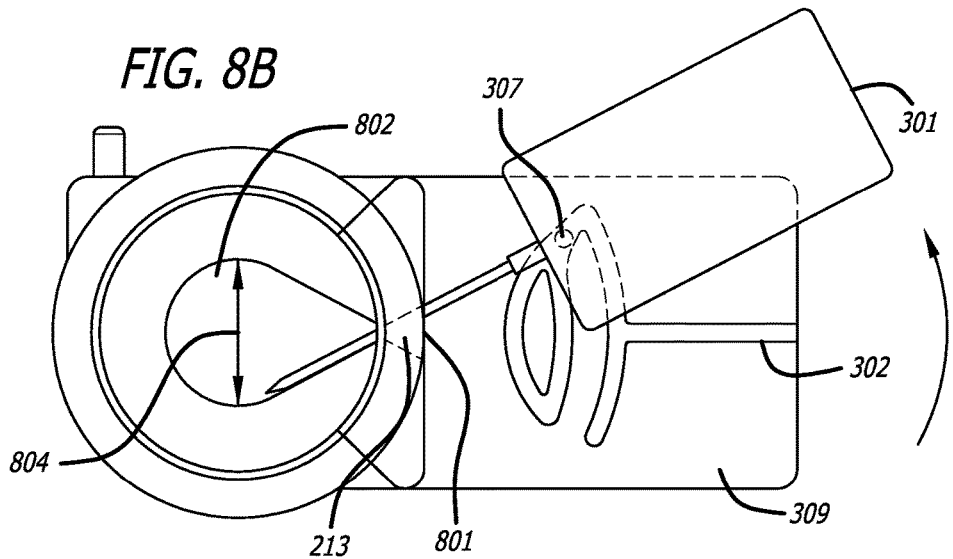

As cutter module 301 is advanced toward the handpiece pin 307 moves along and is restricted by guidance track 302, such that, as depicted by FIG. 8B, as guide pin 307 moves within guidance track 302, a distal end of the cutting tool will move from side to side inside cutting region 802 in a controlled fashion. The path of guidance track 302 defines the size and shape of region 802. Taking the z-axis as the centerline of the handpiece from top to bottom, the path preferably restricts movement of the cutting module, and, thus, the cutting tool moves in an x and y direction within a plane parallel to the top of the handpiece. The interaction between pin 307 and track 302 defines a maximum width 804, or x direction. A physician moves cutting module 301 along the track by beginning the cutting just inside the skin and, following the track to work inward, the fixed (non-cutting) portion of the shaft is always within a region where the tissue is separated; otherwise, the unseparated tissue will prevent the shaft from pivoting freely over the desired region.

Figure 8C:
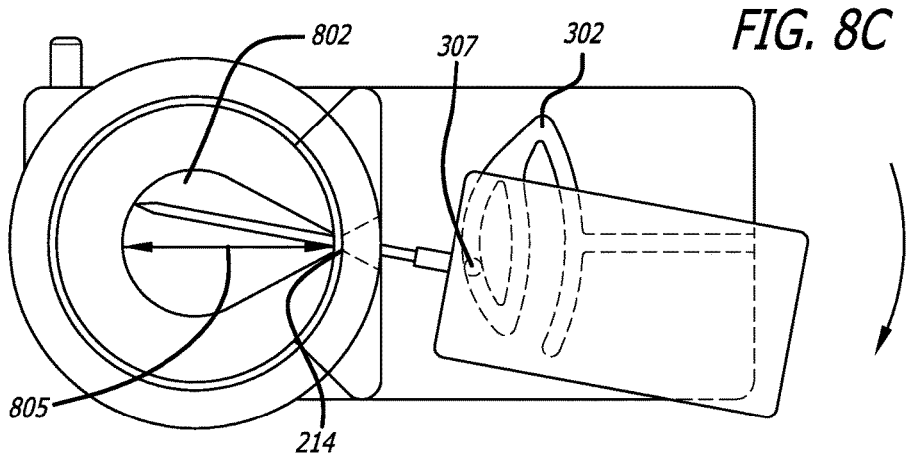

As shown in FIG. 8C, interaction between the pin 307 and the track 302 also defines a maximum length 805, or y direction, of the region 802. The path of guide track 302 preferably defines the region in which the cutting tool will move within the recessed area of the handpiece. The geometry of the track in conjunction with the length of the blade and reciprocation stroke defines the dissection area. After following the entire track the motor is turned off and the cutter is removed. After the power is turned off and prior to removal of the cutter, the dissection can be confirmed by retracing the path with the motor module off. The power may be turned back on to cut any areas not previously released. This same method would apply to any cutting instrument disclosed herein. In the depicted embodiment, the overall resulting region 802 is tear-dropped shaped. However, the path of guidance track 302 and/or conduit 213 and/or entry point 214 can be altered to modify the shape of region 802 to take the form of any shape.

An alternate range of motion may be enabled by selection of the guidance tracks illustrated in FIGS. 6A and 6B. A physician may also choose to restrict the motor module within the multiple arcs 602 and not complete the outer regions of any one of the arcs. The staggered central track 601 may still be used to advance the module toward the final inverted arc 603. In a further method, the physician may choose to not complete successive arc(s). Thus, by these methods, a reduced area of dissection can be created.

Figure 9A:
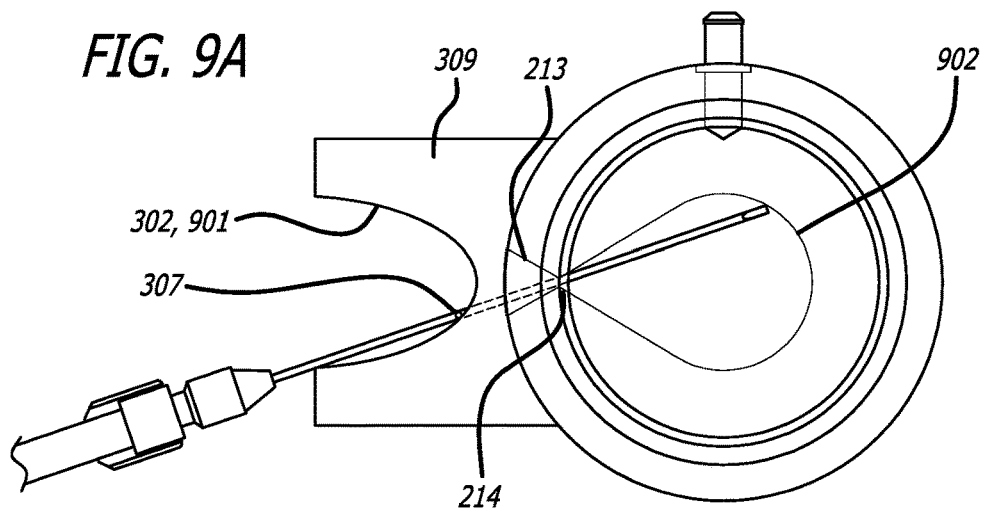
Figure 9B:
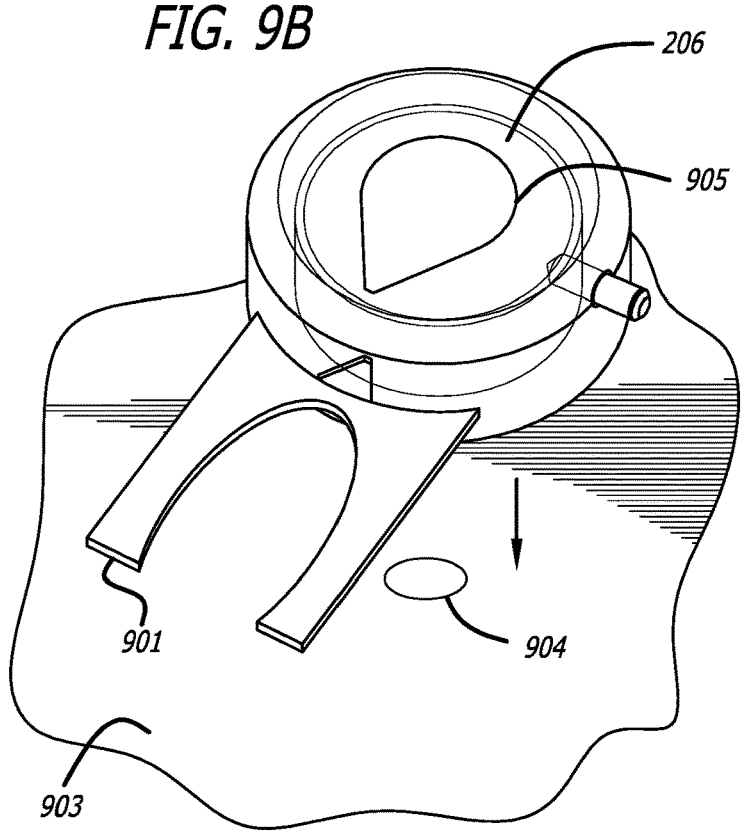

FIGS. 9A through 9C depict an embodiment of platform 309 and guidance track 302. In this embodiment guidance track 302 is a semi-ovoid shape formed along an outer edge 901 of platform 309. Guide pin 307 is positioned on a side of the cutting device (e.g., cutting implement 102 or sleeve 304) such that guide pin 307 moves along the curvature of guidance track 302 and such that the dissection can only occur within the defined boundary 902 (similar to FIGS. 8A to 8C). Although FIGS. 9A through 9C depict the guidance track used with an anesthesia needle, it should be recognized that the depicted guidance track (or any guidance track disclosed herein) can be used with either an anesthesia needle or any cutting instrument disclosed herein.

Figure 10A:
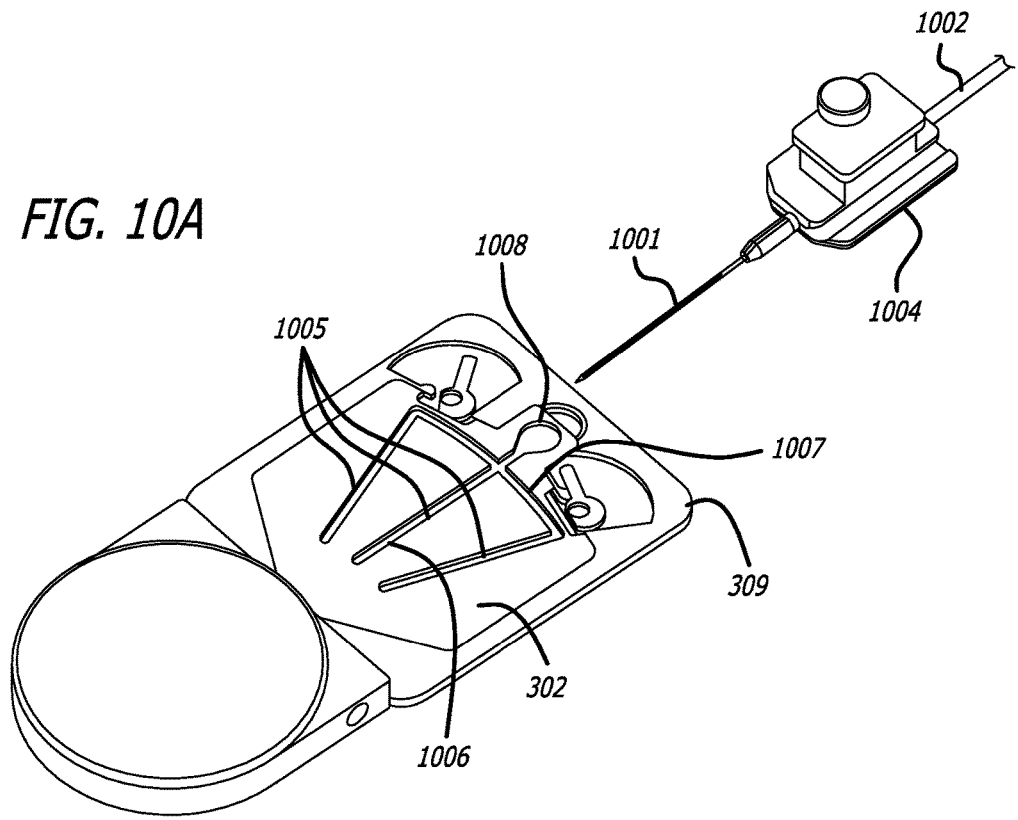
FIGS. 10A and 10B depict an embodiment of the guidance track, including a syringe pump connected to needle or cannula and a source of injectable fluids.
Figure 10B:
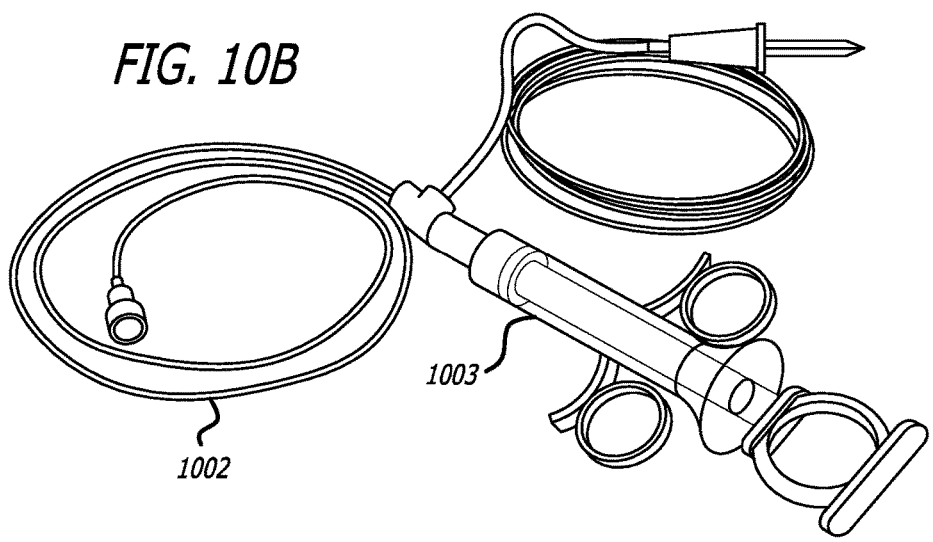
Figure 11A:
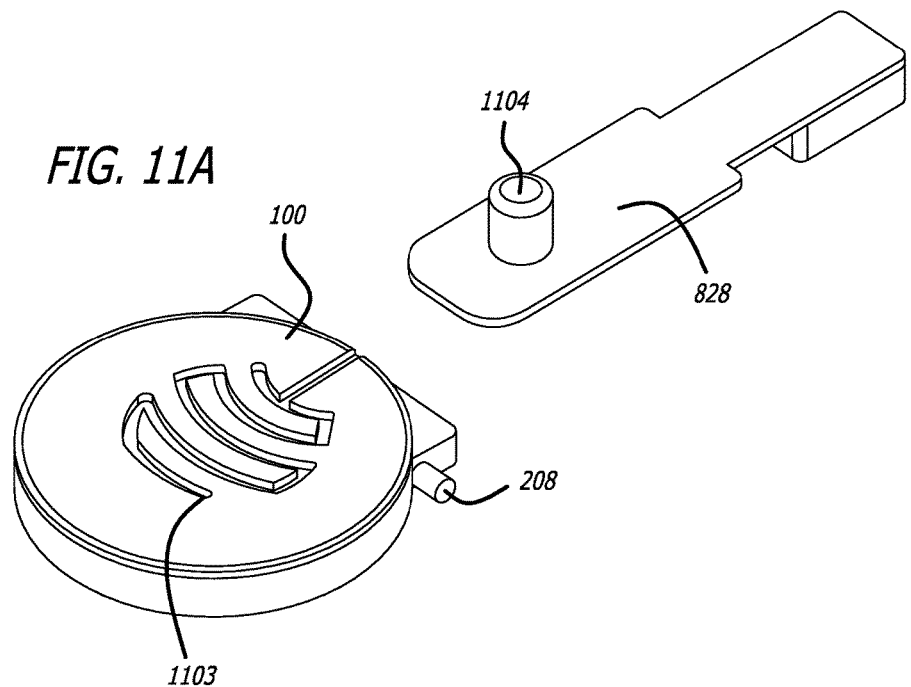
FIGS. 11A through 11D depict an embodiment of the dissection device and cutting tool, including a guidance track positioned on the top of the device.
Figure 11B:
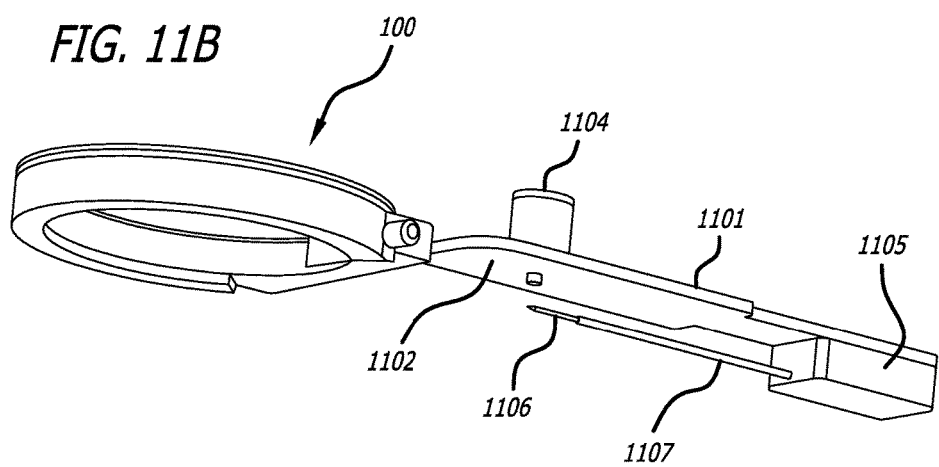
Figure 11C:
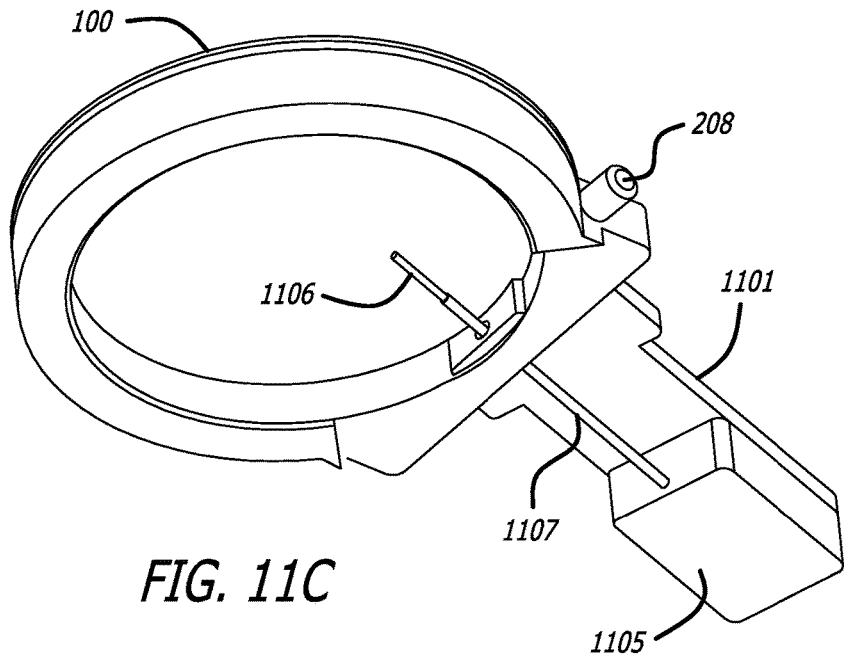
Figure 11D:
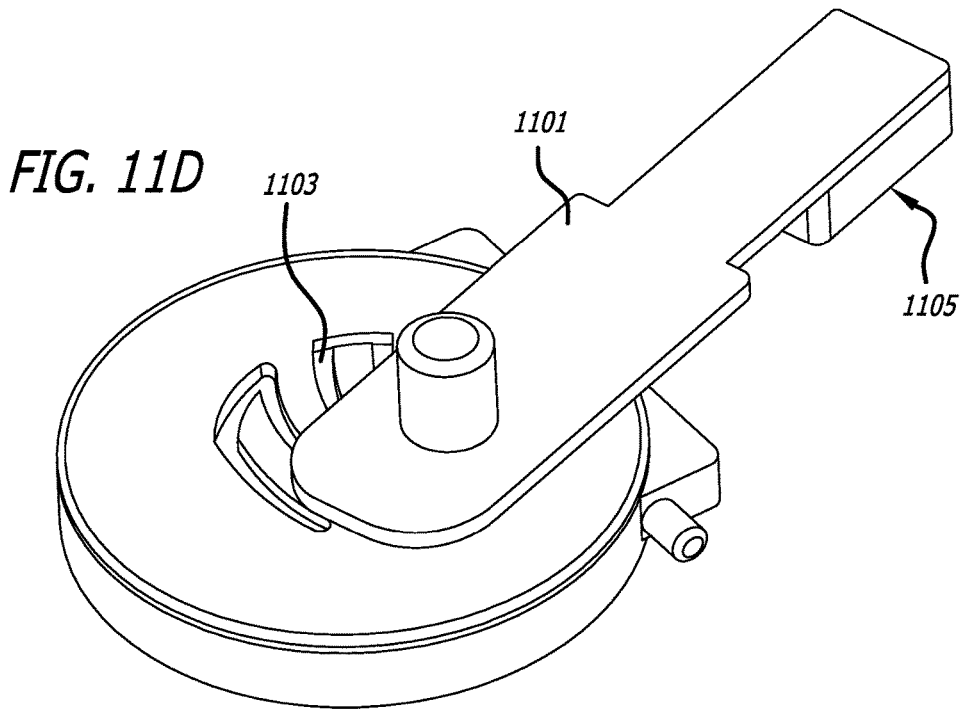

In a further embodiment of platform 309, depicted by FIGS. 10A and 10B, guidance track 302 is configured to provide a controlled delivery of treatment fluid through needle 1001. Needle 1001 may be a tube, an hypodermic needle and may have a multitude of holes for increased lateral fluid dispersion. A supply tube 1002 provides fluid connection of needle 1001 with a syringe 1003, syringe pump, roller pump or other injection mechanism known in the art. In certain embodiments, a needle control module 1004 is included to house needle 1001 and to provide support for movement along guidance track 302. Movement of needle 1001 along guidance track 302 provides delivery of the treatment fluid in precise locations of the dissection region and minimizes the amount of infusion fluid required for a single treatment and/or over multiple treatment sites. Needle control module 1004 preferably includes a guide pin to be engaged into guidance track 302 of platform 309. The guide pin guides the needle/cannula to insure that the injectable fluid is injected into the tissue at the desire depth and desired locations within a predefined treatment area defined by the path of guidance track 302.

An embodiment of guidance track 302 for use with needle control module 1004 includes three radial channels 1005 converging toward a center point located beyond the guidance track in a direction toward the portion of the needle delivering the fluid to the treatment area. A central channel provides a straightened portion 1006 that allows the guide pin of needle control module 1004 to be positioned within the track at its beginning and to move in a forward direction to insert needle 1001 through conduit 213 and entry point 214 and into the recessed area. Downward from the starting position of the central channel, the central channel intersects and passes through a cross channel 1007. In this embodiment, cross channel 1007 is in the shape of a wide arc having a center in a direction toward the center point. A radial channel begins at each end of the cross channel such that a guide pin moving along the path of the cross channel will move into a radial channel by traveling along and beyond an end of the cross channel. Each radial channel converges toward the central channel as the needle control module moves in a direction toward the center point. An enlarged opening 1008 of the central channel marks the starting point of the central channel. In those embodiments in which the guide pin has an enlarged head, the enlarged opening of the center channel is suitable for receiving enlarged head, and the guidance track has an enlarged underside for passage of the enlarged head along the path while preventing the cutting module from being lifted off platform 309 and/or supports the needle control 1004 module 1004 at a predefined planar orientation relative to platform 309.

In one embodiment, with continued reference to FIGS. 10A and 10B, when the guide pin on needle control module 1004 reaches cross path 1007 along the central channel 1006, the needle has pierced the skin captured in recess 105. When the guide pin is moved along cross channel 1007, the needle rotates within the pierced area, but does not move forward or exit the skin. Therefore, when the needle is moved by control module 1004 down a converging radial channel and back, cross channel 1007 provides a stop which maintains the needle within the skin. In this manner, fluid may be infused over the entire area through a single needle puncture. In a further embodiment, with reference to FIG. 12A, central channel 1006 stops at cross path 1007, and four converging radial channels 1005 can be used for fluid infusion. In this manner, all the converging channels 1005 start and stop, and cross path 1007 prevents the needle from being withdrawn from the skin by requiring the guide pin on control module 1004 to move directly across cross path 1007 from a radial channel to central channel 1006.

FIGS. 11A through 11D depict a yet further embodiment of the platform. In this embodiment, platform 309 of the previous embodiments is replaced by support arm 1101 movably coupled to handpiece 100. Support arm 1101 includes a guide pin 1102 which interacts with a guidance track 1103 defined in the top portion of the handpiece 100. A handle 1104 is used to advance support arm 1101 as guided by the interaction of the guide pin 1102 and guidance track 1103. Guide pin 1102 moves within and along guidance track 1103 to stabilize a cutter module 1105 at a proper position proximate to handpiece 100. Cutter module 1105 can be adapted to use any cutting mechanism disclosed herein. In one aspect cutter module 1105 may include cutting implement 102. In another aspect cutting module 1105 is manually controlled. In the depicted embodiment cutting module 1105 is motor controlled and includes a housing, a gear motor, cutting blade 1106, and sleeve 1107 similar to the embodiment depicted by FIGS. 3 and 4. Guide pin 1102 is located on a lower side of support arm 1101 proximal to sleeve 1107. Cutting module 1105 is fixed to support arm 1101 and thus the support arm is moved to advance cutting blade 1106. In certain aspects cutting module 1105 may include an RF cutter. The compact size of this third embodiment is particularly suited to facial applications.

In further embodiments of the platform, the handpiece may not have a perimeter wall and/or a defined recessed area. In such embodiments, handpiece 100 may include an apposition platform for covering a portion of the dermis to be treated. The apposition platform may include a guidance track 1103 and support arm 1101 to support the cutting tool from above. In some embodiments the perimeter wall does not encompass the entire perimeter of the device, but, rather, encompasses only what is necessary to support conduit 213 and/or entry hole 214. In some embodiments, the platform and guidance track are omitted completely, and, stability and control of cutting tool and cutting below the apposition platform is achieved by manual operation and skill of the medical practitioner operating the device.

Some embodiments of handpiece may include an adjustable top or lid to change the distance between an inner side of the top of the handpiece and the bottom edge of the perimeter elevation of the handpiece. Moreover, in such embodiments, the top of the handpiece 100 is adjustable in relation entry point 214 of conduit 213 to adjust the volume of recessed area 105 and the depth 215 at which cutting tool 102 cuts the subcutaneous tissue when inserted through conduit 213.

In some embodiments, depicted by FIG. 12, the handpiece includes a reversible lid 1201. In the depicted embodiment, lid 1201 has a recessed side 1202 and a raised side 1203. Both sides of lid 1201 are configured to fit snuggly over perimeter wall 104 such as to be easily removed yet maintain a airtight seal to prevent vacuum leakage when a vacuum is supplied to handpiece 100. Depending on which side of lid 1201 is positioned over perimeter wall 104, depth 215 of recessed area 105 will vary. Recessed side 1202 has a shallow rim 1204 which is sized to fit the profile of a top 1205 of perimeter wall 104. When lid 1201 is secured to handpiece 100 with recessed side 1202 faced downward and toward recessed area 105, depth 215 is increased and the volume of recessed area 105 is correspondingly enlarged. Conversely, raised side 1203 has a platform 1206 which is sized to snugly fit within the profile of top 1205 of perimeter wall 104. When lid 1201 is secured to handpiece 100 with raised side 1203 faced downward and toward recessed area 105, depth 215 is decreased and the volume of recessed area 105 is correspondingly reduced. As in the depicted embodiment, handpiece may further include latches 1207, spaced about the perimeter of top 1205 of perimeter wall 104 to securely fasten lid 1201 to handpiece 100 via corresponding locking apertures 1208. Each corresponding locking aperture 1208 is configured to receive a latch 1207 such that when latch 1207 is inserted into aperture 1208 and lid 1201 is subsequently rotated 1209, latch 1207 becomes locked within aperture 1208, and lid 1201 is secured with respect to the latch-aperture communication.

Accordingly, lid 1201 is reversible so that to change depth 215 the operator of the handpiece needs only remove the lid, flip it over, and re-attach it. In some embodiments, an o-ring (not shown) or rubber-like material may optionally be interposed on lid 1201 about rim 1204 and/or platform 1206, or about top 1205 of perimeter wall 104, to provide a secure fit and/or prevent vacuum leakage. In further embodiments, several lids may be provided with multiple and varying recess areas to allow depth to be changed, whether the lids are reversible or not.

Figure 13A:
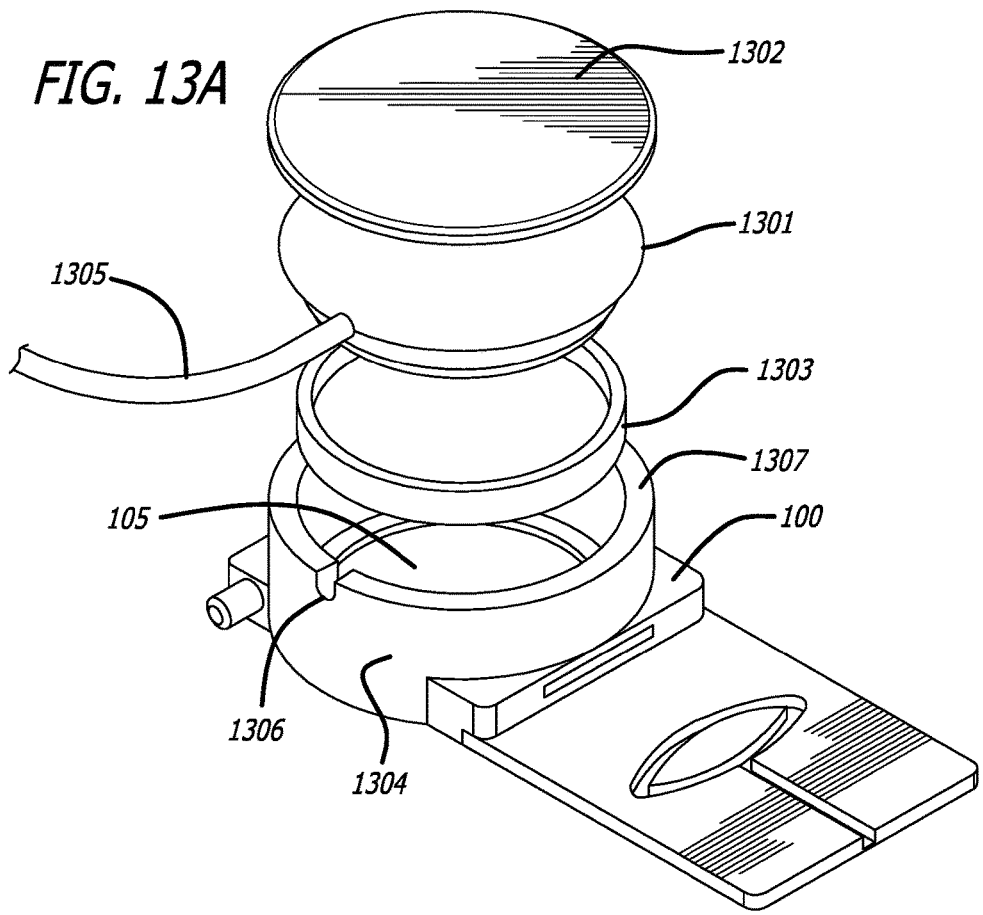
FIGS. 13A and 13B depict exploded and cut-away views of the dissection handpiece, including an inflatable bladder for controlling cutting depth.
Figure 13B:
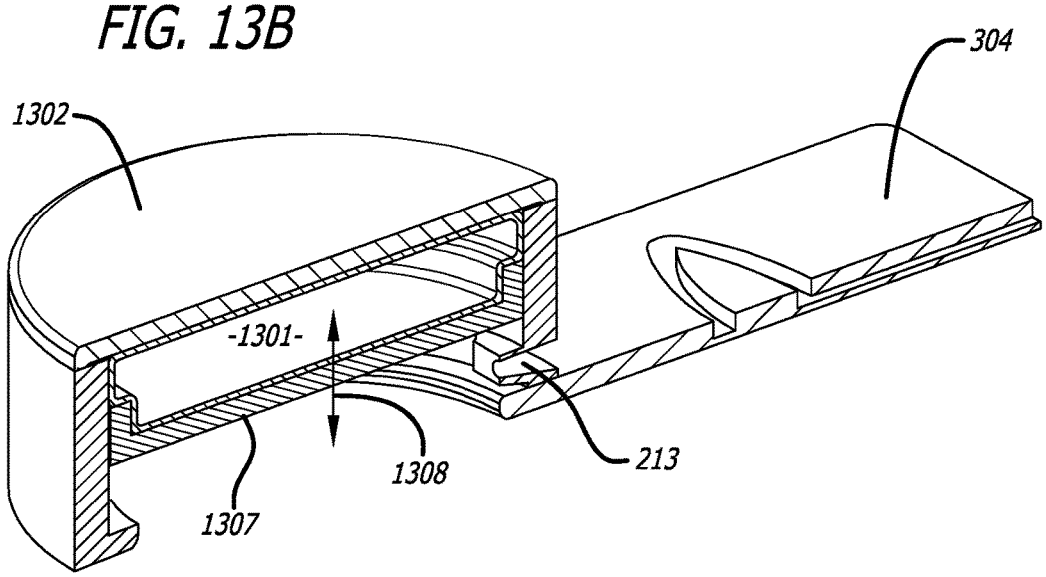

In a further embodiment, depicted by FIGS. 13A and 13B, an inflatable bladder 1301 conforms to the inner diameter of handpiece 100 and is disposed between a rigid outer lid 1302 and a rigid inner lid 1303. Inner lid 1303 is slidably disposed inside the circumference of handpiece 100 whereas rigid outer lid is rigidly mounted to the perimeter wall 1304. Tubing 1305 fluidically connects bladder 1301 to pressure source (not shown) for inflation of bladder 1301. Inflatable bladder 1301, rigid outer lid 1302, and rigid inner lid 1303 are then positioned to fit into the top of handpiece 100, with tubing 1305 protruding through a port or an upper indentation 1306 located along the upper rim portion 1307 of perimeter wall 1304. These components fit together such that rigid outer lid 1302 is coupled to perimeter wall 1304 of handpiece 100, and enclosing bladder 1301 and rigid inner lid 1303 are slidably disposed within handpiece 100. As can be seen by FIG. 13B, adjustment of pressure in bladder 1301 causes inner lid 1303 to raise or lower 1308, correspondingly, thereby changing the volume of recessed area 105 and allowing for selection of a desired dissection depth.

Figure 14A:
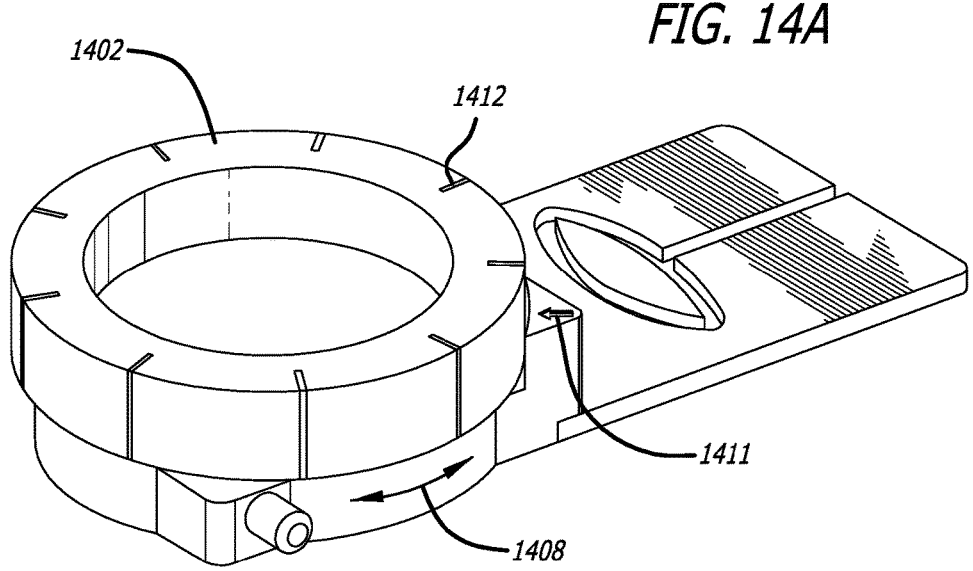
FIGS. 14A and 14B depict exploded and cut-away views of the dissection handpiece, including a threaded engagement for controlling cutting depth.
Figure 14B:
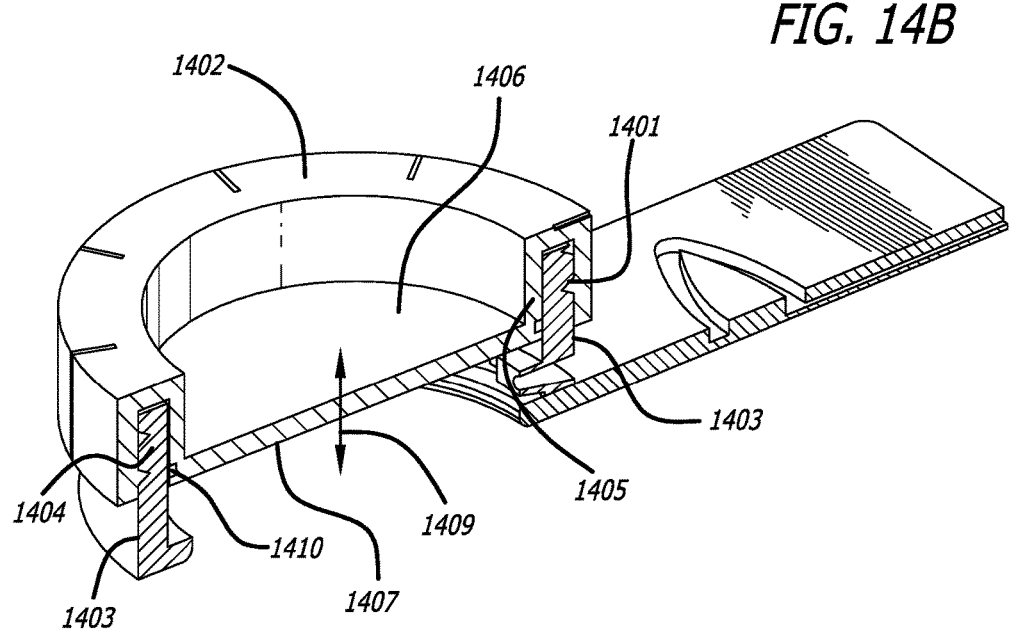

In a yet further embodiment, depicted in FIGS. 14A and 14B, the handpiece includes a threaded engagement 1401 between a threaded lid 1402 and open perimeter wall 1403 of the handpiece. Lid 1402 is threaded onto the upper rim 1404 of wall 1403 similar to a food jar. Lid 1402 includes an outer edge and an inner edge 1405 which grasps rim 1404. Lid 1402 may further include a recessed area 1406 defined by the circumference of inner edge 1405. An interior side 1407 of recessed area 1406, along with an associated portion of perimeter wall 1403 makes up previously described tissue apposition surface 203. Rim 1404 is threaded such that, as lid 1402 is rotated 1408, recessed area 1406 (including tissue apposition surface 203) moves in direction 1409 (orthogonal to the dermis) to a desired depth within handpiece 100. An optional o-ring 1410 may be positioned along the outer circumference of inner edge 1405, between inner edge 1405 and an inner side of rim 1404 to prevent leaking of vacuum applied to the device. Threaded lid 1402 may further include reference numerals (e.g., 9 mm, 10 mm, etc.) defining the depths of tissue apposition surface 203 as lid 1402 is rotated. A reference mark 1411 is placed on the body of handpiece 100 to mark and indicate the current depth setting. Lid 1402 may include further complimentary markings 1412 to be aligned with mark 1411 at various depths.

In a yet further embodiment, the depth is adjustable by way of a sliding platform that moves the entry of the tool device up or down relative to the inside of the lid. Based on the depicted embodiments, one of ordinary skill in the art will appreciate that there are other ways to construct a variable depth vacuum assisted handpiece and such designs fall within the scope of the device and method disclosed herein.

Turning back to FIGS. 10A and 10B, the device and system may further include a syringe or syringe pump 1003 connected to needle or cannula 1001 and a source of injectable fluids. The treatment fluid may be injected prior to or after deployment of the cutting tool. The fluid may be actively injected, for instance by using the syringe, or may be drawn into the pocket from an external reservoir by the reduced pressure created by a vacuum applied to the handpiece. The fluid may perform a number of functions, including enlarging the subcutaneous tissue pocket, providing structural support, and affecting the biological response to the procedure by means of an active pharmaceutical ingredient (API). Simple enlargement of the tissue pocket may be achieved by the injection of saline. Support for the pocket and surrounding tissue may be achieved by injection of a fluid containing a liquid polymer formulation to enhance viscosity, or by injection of a suspension of microparticles. Suitable polymers for injection may include commonly used materials for cosmetic and reconstructive surgery, such as collagen and hyaluronic acid. Suitable microparticulate systems may include formulations based on biodegradable polymers, like poly-lactic acid and poly-glycolic acid and their copolymers, or permanently implanted materials like silicones or poly-olefins of polyurethanes. APIs may include compounds like local anesthetics, anti-inflammatories, antibiotics, hemostatics, or healing response modifiers like collagen promoters. Multiple functions can be combined in an injected fluid, for instance the polymeric components may be used as controlled release carriers for the APIs.

The needle or cannula 1001 can be used to inject the injectable fluid into the tissue prior to, during, or after the creation of a surgical incision. Accordingly, the needle or cannula may be inserted through conduit 213 and through entry hole 214, through the skin, and into the subcutaneous tissue. The needle or cannula may optionally be disposed on a needle control module 1004 for use with an embodiment of guidance track 302.

In some embodiments, needle 1001 includes multiple injection ports along a side of the needle and flush with its outer surface. The ports are configured to discharge a fluid in a direction substantially orthogonal to an axis of the needle and in a distribution substantially parallel to the top of the handpiece. Multiple ports are used to allow a broader distribution of fluid delivered by needle control module throughout the area of treatment during an injection. The fluid will infuse into the subcutaneous tissues, including the subcutaneous fat and adipose tissue. The ports may, in one embodiment, be aligned on a side of needle 1001 so that when needle 1001 is positioned in the subcutaneous treatment area it can be further oriented such that the infusion occurs predominately in the plane of tissue, parallel to the surface of the skin, ensuring that the fluid is further distributed over the largest possible area. In other embodiments, the ports may be staggered. One particular advantage of a staggered configuration is an increased mechanical strength. Another advantage is the ability to infuse fluid throughout the treatment area without necessitating perfect alignment of needle 1001. In a further embodiment, the needle may include a partially crimped tip for piercing a dermis while maintaining the ability to discharge the treatment fluid from the crimped tip while allowing a simultaneous discharge from the injection ports on its side.

As depicted by FIG. 15, the system may further include a microprocessor unit 1501 having a graphical user interface 1502 to be operably connected to and used with injection device 1003, 1004, a source of injectable fluid 1503, a microprocessor controller 1504, and, an optional waste reservoir 1505. A microprocessor and software (not shown) may be included and used to control microprocessor unit 1501 to meter the infusion according to parameters set by the physician. The system can display drug dose or other infusion information and provide warnings or alarms. The needle injection module 1002 and/or a syringe pump 1003 communicates with the microprocessor unit 1501 information specifying the volume of injectable fluids injected into the tissue. The graphical user interface may prompt a user to enter information specifying a concentration of the injectable fluid and a weight of the patient. The microprocessor may include logic for determining a maximum safe dosage of the injectable fluid based on the weight of the patient and the concentration of the injectable fluid. In one aspect, the microprocessor may also cause graphical user interface 1502 to display at least one warning message when the volume of fluid injected by the syringe pump exceeds a predefined threshold which is less than the maximum safe dosage and may instruct the syringe pump to terminate injection when the volume of fluid injected by the syringe pump reaches the maximum safe dosage. In yet a further aspect, the graphical user interface may enable the user to over-ride the maximum safe dosage such that the syringe pump continues injecting the injectable fluids once the maximum safe dosage has been reached.

The graphical user interface also optionally displays an elapsed amount of time since the injection control module and/or syringe pump initiated pumping injectable fluids. In some aspects, the microprocessor tracks the amount of elapsed time since the system initiated pumping injectable fluids and may calculate a recommended treatment start time and a recommended treatment end time. For example, if the injectable fluid includes anesthesia and or a vasoconstrictor, the microprocessor indicates when the surgical incision can be created, i.e., when the anesthesia is effective. Microprocessor may also use information such as the volume of injectable fluids pumped by the syringe pump and elapsed time since the syringe pump initiated pumping injectable fluids to determine the treatment start time and a recommended treatment end time. Microprocessor 1501 and graphical display 1502 can be further configured in some embodiments to control and/or display other information regarding the use of the handpiece or cutting tool. For example, microprocessor 1501 may control the vacuum pump used to capture the tissue in the treatment area and graphical display 1502 may be used to display a vacuum pressure or an elapsed time a vacuum has been supplied to handpiece 100 by the vacuum pump.

In a further embodiment, the device and method may be configured to use a high-pressure stream of fluid such as saline to create the lesion or to sever fibrous septae or disrupt the subcutaneous tissue. A cutting device suitable for use with some aspects of the present invention is commercially marked by HYDROCISION™. HydroCision's proprietary FLUIDJET™ technology is the basis of a new surgical modality, HydroSurgery. HydroSurgery uses a controlled hair-thin supersonic stream of water in a precise manner to provide an effective cutting, ablation, and collection system for medical applications. HydroSurgery has the power density of laser and radiofrequency technologies without causing collateral damage to tissue. HydroSurgery also has the unique benefit of simultaneously cutting, ablating, and removing the targeted tissue and debris.

In some embodiments needle 1001 is configured to increase a kinetic energy of the fluid when it is injected by injection device 1004. Injection device 1004 is guided along guidance track 302 to inject a fluid at a high pressure orthogonal to the surface of the dermis, and at depth 215, to cut fibrous septae 220 located in a treatment area located in the subcutaneous tissue 205. It has been determined that a pressure of between 20 and 60 Bar a water-jet with sufficient cutting power to cut 8 mm into subcutaneous tissue in one single pass or rotation of the needle. Deeper cuts can be achieved by repeated application on the same cut. Water-jet dissection can also lead to a water uptake of the cut tissue. Morphologically all the vessels, lying in the cut are undamaged if the pressure doesn't exceed 40 Bar pressure range. Preferably, the pressure is thus set to be above 50 bar (in the 50 to 60 bar range) to ensure that fibrous septae 220 located in the treatment area are cut. In this embodiment, needle 1001 includes a nozzle 1506 at a distal end of the needle. Preferably, nozzle 1506 is configured to increase a kinetic energy of a fluid injected by the injection device through the needle. In some embodiments, the nozzle is a convergent nozzle. Thus, the throat of the nozzle converges toward the tip of the needle. In other embodiments the nozzle may be a divergent nozzle and/or be configured to slow the kinetic energy of the fluid injected.

In a yet further embodiment, the device and method may also use the device and high powered pressure burst described in, and incorporated by reference from, patent application Ser. No. 12/555,746, filed Sep. 8, 2009, which is a continuation-in-part and claims priority from U.S. application Ser. No. 11/515,634, filed Sep. 5, 2006, and from U.S. application Ser. No. 11/334,794, filed Jan. 17, 2006, now U.S. Pat. No. 7,588,547, both of which are incorporated by reference in their entirety.

FIG. 16A depicts an embodiment of the cutting mechanism. In this embodiment, an RF cutter 1601 is used. In other embodiments, another cutter such as a harmonic scalpel (e.g. Ultracision® harmonic scalpel) or the like may also be used. RF cutter 1601 may be positioned in an insulating sleeve 1602 that electrically insulates RF cutter 1601 from the body of RF cutting module 1603. In some embodiments, the shaft or non-cutting portion of RF cutter 1601 may also be coated with an electrically insulating coating. The body of cutter module 1603 may include a handle 1604 which is also electrically insulated from RF cutter 1601. Cutter module 1603 may include a guide pin 307 (as in FIG. 3B), and handle 1604 may be used to guide cutter module 1603 along guide track 302. This embodiment illustrates a specialized handle and RF cutting mechanism for use with the guidance track 302 and handpiece 100. Similar to FIGS. 10, and 11A through 11C, guidance pin 814 moves within guidance track 822 to properly position the RF cutter 1301 within the cutting region. The handle may have control buttons (not shown) which activate the coagulation or cutting modes of the RF energy. In some embodiments, the use of a reciprocating motor such as illustrated by FIG. 4 may be used to reciprocate, move, or vibrate RF cutter 1601. It should also be understood that, in some embodiments, the RF cutter may be provided with a reciprocation mechanism or motor control for reciprocating the RF cutter similar to cutter module 301 depicted in FIG. 4.

In some embodiments, RF cutter 1603 may include a bayonet and/or blade at least partially coated with an insulative coating. For example, if the blade/bayonet is two-sided, the insulative coating may cover only one side, leaving the other side exposed. An additional benefit of leaving the side facing the dermis exposed would be to direct additional energy upward for skin tightening. An electrical connection point 1605 connects RF cutter 1601 by means of an electric cable (not shown) to an RF generator 1609 (FIG. 16B).

FIG. 16B depicts a block diagram of a system for performing subcutaneous surgery on a patient. The system includes an RF cutting probe 1601, a vacuum assisted handpiece 100, and an RF generator 1606. The handpiece 100 supports the RF probe such that the probe creates a planar surgical lesion at a predefined depth below the dermis through a minimally invasive puncture between 0.4 mm and 4.0 mm in diameter. In other words, the surgical lesion is created without exposing the wound or creating a skin flap. Handpiece 100 has a tissue-engaging surface defining a recess configured to capture a predefined thickness of tissue. RF cutter 1601 is percutaneously inserted into the tissue captured within the recess such that the planar surgical lesion is created at a depth defined by the height of the recess. RF generator 1609 supplies power to the RF cutting probe and includes an impedance measuring circuit for measuring the impedance of the tissue. The RF generator includes feedback control logic which may include a hardwired electronic circuit and/or software or microcode on a RAM (random-access memory) or ROM (read-only memory) chip executed by a microprocessor or the like within the RF generator. The feedback control logic optimizes the power supplied to the probe based on the measured impedance such that the RF cutting probe cuts efficiently.

The aforementioned system may further include a thermistor or thermocouple (not shown) which may, for example, be provided on the RF cutting probe 1601. In certain embodiments, the thermistor or thermocouple is preferably operably coupled to RF generator 1609 and communicates information indicative of a temperature of the tissue. The feedback control stops the RF generator from supplying power to the tissue when a temperature of the tissue reaches a predefined threshold.

The aforementioned system may contain controlled infusion of a conductive fluid, like saline, to provide additional dispersion of the RF energy, maintain tissue impedance, and/or provide anesthetic benefit.

In some embodiments, a monopolar RF electrode may also be used with handpiece 100 as the return electrode. In this embodiment the system includes an active electrode 1601, an RF amplifier 1609, a vacuum assisted handpiece 100, and a vacuum pump 1606. In one embodiment, handpiece 100 may include an electrically conductive layer (not shown) attached to the interior surface 203 of the handpiece such that, in use, the conductive layer is placed in electrical contact with the skin 204. The conductive layer can be a mesh screen affixed to the handpiece or can be a layer which is sputtered or vacuum deposited on the interior surface of the handpiece. According to some embodiments the conductive layer may be translucent or transparent.

The conductive layer is electrically coupled to RF generator 1609 and thus a conductor electrically coupled to the conductive layer passes through an opening in the handpiece or under the handpiece. The conductive layer may span the entire interior surface of the handpiece or may include one or more windows used to visualize positioning of the handpiece. The conductive layer may be composed of any electrically conductive material, such as copper or aluminum, and/or incorporating an electrically conductive gel. Certain conductive materials may be sputtered or vacuum deposited on the handpiece, providing and additional advantage of being optically transparent (e.g., indium tin oxide (ITO)).

According to one embodiment, the system includes a handpiece fluidically coupled with a vacuum pump 1606 (FIG. 16B), and a needle-like RF electrode 1601 (FIG. 16A) which is inserted through conduit 213 in the handpiece for creating a lesions parallel to the surface of the skin and at a depth 215 defined by the handpiece (FIGS. 2A and 2B). RF electrode 1601 is coupled to RF generator 1609 which includes impedance feedback control logic which may be embodied in software and/or hardware or firmware. The impedance feedback control logic monitors the impedance of the tissue and modulates the power delivered to the electrode to prevent the tissue from desiccating, i.e., preventing a premature impedance spike.

In the disclosed embodiments herein, a subdermal pocket is created using the aforementioned vacuum handpiece in combination with various cutting modalities including cutting blade, laser, high pressure fluid injection (e.g., hydrocision), or RF electrode. After the subdermal pocket is created, the cutting tool is swapped for an RF electrode which is operated in a coagulation mode (as opposed to a cutting mode) to stop any bleeding. Use of the RF electrode in the coagulation mode may result in contraction of collagen in the tissue leading to skin tightening and may lyse some of the tissue. Thus, if the subdermal pocket is created within a shallow fat layer then operation of the RF electrode in the coagulation mode may lyse some adipose tissue. Use of the RF electrode in the coagulation mode may increase the healing response time and may lead to less bruising.

In the aforementioned embodiment, the same RF electrode 1601 may be used both to create the subdermal pocket and to induce haemostasis. Namely, RF electrode 1601 may be operated in a cutting mode to create the subdermal pocket and then may be operated in a coagulation mode to create or induce haemostasis.

Figure 17:
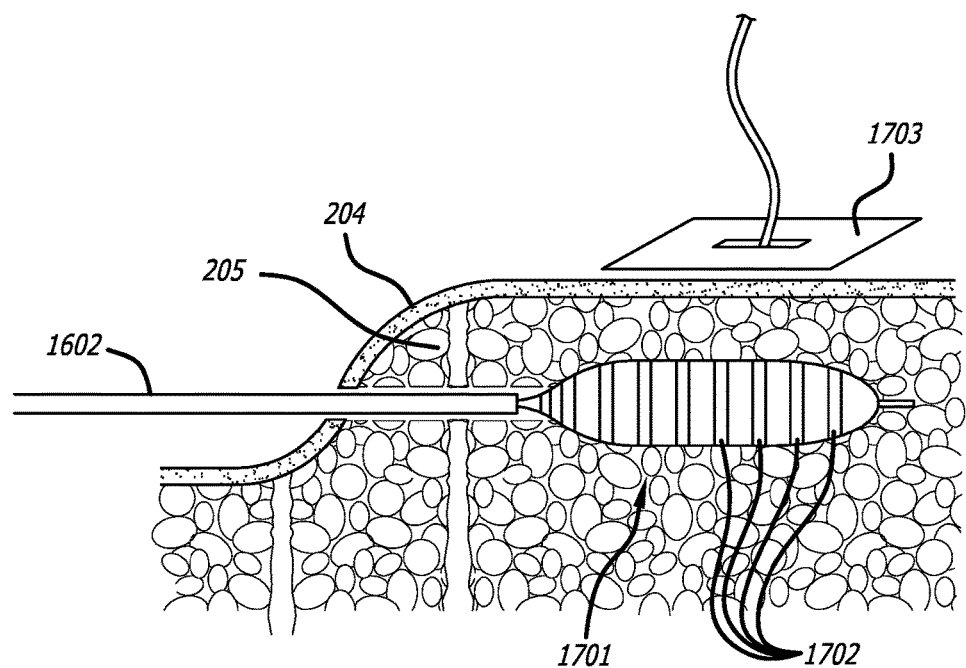
FIG. 17 depicts an embodiment of an RF device, including an inflatable member having an RF electrode provided on an exterior surface.

In one embodiment, depicted by FIG. 17, an inflatable member 1701 having an RF electrode 1702 provided on an exterior surface thereof is used to facilitate coagulation. More particularly, a subdermal pocket below dermis 204 is created using the handpiece 100 in combination with any of the aforementioned cutting modalities including cutting blade, laser, high pressure fluid injection (e.g., hydrocision), or RF electrode. Inflatable member 1701 is inflated within the subdermal pocket and electrode 1702 attached thereto is operated in a coagulation mode to stop any bleeding. It should be understood that the device may also utilize a return electrode 1703 placed in contact with the patient's tissue. In some embodiments, return electrode 1703 may be placed in a location remote from the treatment site. In the depicted embodiment, electrode 1702 includes multiple circular bands disposed about the circumference of inflatable member 1701. However, it should be recognized that the electrode may take the form of other configurations, for example, one or more linearly disposed bands along the length of inflatable member 1701. As described above, the vacuum handpiece may include a return electrode, or the return electrode can be a discrete item separate and remote from the handpiece.

In a further embodiment, the cutting member (i.e., any tool disclosed herein capable of cutting tissue or creating a lesion within tissue) may include an electrode or a heating element. In an embodiment where the cutter includes an electrode, the cutter itself may be the electrode or the cutter may be a discrete element provided on and electrically insulated from the rest of the cutter. In an embodiment where the cutter includes a heating element such as a resistive heating element, the heating element may be provided on a surface of the cutter or may be fully or partially embedded within the cutter. In all such embodiments, the cutter may include a thermocouple to measure the temperature of the cutter and/or tissue. The electrode/heating element may be used to coagulate the tissue, minimize bleeding/bruising, and/or to provide skin tightening.

Referring back to FIG. 2A, cutting tool 102 may be configured to cut the fibrous septae 220 at the interface between the dermis and the fat layer, within the shallow tissue layer 205 which applicant defines as the layer 0-10 mm below the dermis, or, in the deep tissue layer 221 defines as the layer 10-30 mm below the dermis, e.g., between the subdermal fat layers and the skin 204, at depth 215. Previously described embodiments included a mechanical or motor-controlled bayonet-like device, RF cutter, a high-pressure injection system, needle-type injection, and the like. Turning now to FIG. 18, the cutting tool 102 may also include an elongated thin hollow subdermal catheter-like instrument 1801 having a retractable cutting blade 1802.

The term "subdermal catheter" is used herein to describe any elongated object which can be used to penetrate the skin or be placed through a hole in the skin, including, but not limited to, a hypodermic needle, a cutting tool, a catheter, or other device that can puncture or be placed through the surface of the skin. The subdermal catheter is inserted through an incision (made by a sharpened distal end of the catheter or other cutting device) between 0.4 and 4 mm because to avoid or minimize residual scarring which are undesirable in a aesthetic procedure. Subdermal catheter 1801 can be rigid or flexible, and may be made of a stainless steel alloy, metal, plastic, or any other material known in the art.

The distal end 1803 of subdermal catheter 1801 is preferably configured to be percutaneously inserted into a treatment area and to move within the treatment area in a manner substantially parallel to the surface of the skin. In some embodiments, distal end 1803 of subdermal catheter 1801 may be honed, composed of a separate sharp tip such as a trocar tip, or may be equipped with unbeveled blunt-tip. It may be placed through the skin with an introducer.

Retractable cutting blade 1802 includes one or more blade members 1804 deployable from a collapsed position to an extended, lateral position. In some embodiments the one or more blade members 1804 are deployable from one or more sides of subdermal catheter 1801 at or near a distal end 1803. In this embodiment, cutting tool 102 preferably maintains a narrow profile, taking on the dimensions of a relatively large gauge needle, so that when blade members 1804 are fully collapsed it may be percutaneously inserted into the subcutaneous level of tissue, in the subdermal fat layer below the epidermis and dermis layers. Blade members 1802 are preferably configured to remain substantially parallel to the surface of the skin when in the extended position. Once deployed, the blade members 1802 can be used to shear fibrous septae 220 by manipulating the device in a forward and backward motion parallel to the epidermis to create a dissection plane beneath the skin. The device has been shown to especially useful in breaking up fibrous structures that are oriented in a parallel fashion (and perpendicular to the skin).

In one embodiment, depicted by FIG. 19A, a single blade member 1901 is pivotably associated with cutting tool 102 at or near a distal end of the cutting tool such that when blade member 1901 is collapsed or retracted it is parallel to the device, and when it is deployed the ends of the blade member extend laterally away from the device. In another embodiment, as shown by FIG. 19B, a single blade member 1902 is pivotably connected at a proximal pivot point 1903 of the blade member such that the blade member 1902 foldably pivots from a closed position wherein the unconnected (distal) end 1904 is proximate to, or inside, subdermal catheter 1801, to an open position wherein the unconnected end 1904 of the blade member extends outward from the pivot point 1903.

In a further embodiment, as shown by FIG. 19C, the device includes two blade members 1902 pivotably connected at an (proximal) end of each blade member such that the blades foldably pivot from a closed position wherein the unconnected (distal) ends 1904 are proximate to each other, to an open position wherein the unconnected ends 1904 extend outward from pivot point 1903. In one aspect of this embodiment, the two blade members 1902 are connected together at common pivot point 1903. In another aspect, the blade members 1902 may be connected at independent pivot points (each blade having its own pivot point 1903) attached to, or associated with, a common rigid member. As shown by the illustrative embodiments the one or more blade members may be collapsed to and from subdermal catheter 1801 by way of an elongated opening 1906 on each respective side of the device.

Figure 20:
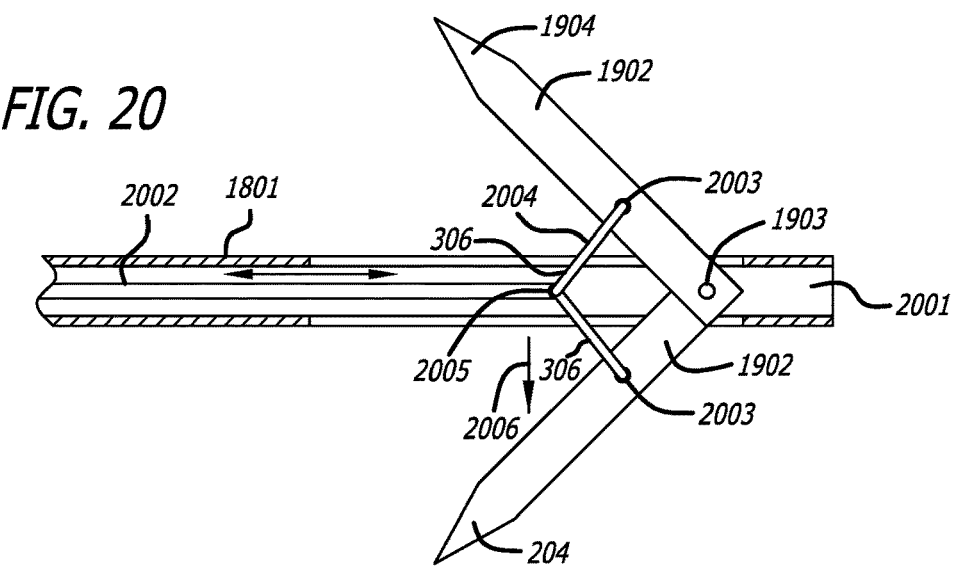
FIG. 20 depicts a blade support mechanism.

In some embodiments, as depicted by FIG. 20, the blade members 1902 are associated with a supporting structure 2001. Supporting structure 2001 may include a hollow tube or may be a flat support surface on which the blade members are pivotably affixed. In some embodiments subdermal catheter 1801 may comprise at least a portion of supporting structure 2001. A deployment member 2002 may move inside subdermal catheter 1801 and/or be associated with supporting structure 2001. In some embodiments, the pivot location of one or more blade members (comprising a common pivot point or a common rigid member having multiple pivot points) is connected to, or associated with, supporting structure 2001 and elongated deployment member 2002 for deploying the blades. Deployment member 2002 moves to release the blade from a constrained position, and may move to retract the blade members from a deployed position. Deployment member 2002 is preferably rigid and can be made of stainless steel, metal alloy, plastic, or any other similar material. The material of deployment member 2002 may also be non-rigid or semi-rigid depending on the embodiment and the application of the device.

Because of the device's narrow profile and protracted cutting blades it is preferable to provide a maximum supporting force for each blade member against the internal lever force imposed on the blade members when coming into contact with and/or cutting through the fibrous septae. Thus, two embodiments of mechanisms that provide efficient deployment and support are explained for illustrative purposes.

With continued reference to FIG. 20, pivot location 1903 is fixed at a point near or at the end of the device. A distal end 2003 of a collapsible support member 2004 is connected to a respective blade member at a location between its pivot point 1903 and distal end 1904 of respective blade members 1902. A proximal end 2005 of support member 2004 is located proximal to device 102 and tracks parallel to the device such that moving proximal end 2005 of the support member 2004 toward fixed pivot location 1903 applies an outward force 2006 on blade member 1902 to move the blade member outwardly from the device.

In some aspects, deployment member 2002 may be associated with proximal end 2005 of support member 2004 from a location distal from pivot location 1903 to a location proximal to pivot location 1903. The support member may have a self-locking mechanism which selectively locks/unlocks the support member in place once it has extended the blade member to the desired location. The self-locking mechanism can be any means known in the art. For example, the self-locking mechanism may lock and unlock by sudden force on the common joint of the support member as a result of an equal force placed on the deployment member.

As the support beam is collapsed, typically by moving deployment member 2002 in a backwards direction, it acts on the blade member to move the blade member from a deployed position to a collapsed position. In embodiments where there are two blade members, support member 2004 may be comprised of two rigid members 2004 pivotably joined together at, and collapsible from, a common center by a common joint 2005, and connected to the respective blade members 1902 at the opposite ends 2003 of rigid members 2004. The proximal end of each rigid member 2004 is located proximal to the device and tracks parallel to the device such that moving center joint 2005 deploys or retracts each blade member simultaneously in a manner similar to that described with one blade member. The two rigid members may lock into a straight rigid position when fully deployed.

In another embodiment, each respective blade member may be deployed using a channel and pin mechanism. A pin may be associated with the blade member near the pivot point. As the deployment member is moved from a proximal to distal position the pin associated with the respective blade moves within a respective channel disposed on a supporting structure. The channel may widen at the distal end to open the blade member into a fully deployed position. In some aspects, the pivot location may also move proximally as the blade member opens and distally as the blade member closes. In some aspects, one or more of the channels may have a lock to secure the blade member via the pin when a respective blade member is in the deployed position. In other aspects, the subdermal catheter or other supporting structure may have a lock channel at a distal end into which the blade member will snap into as it completes deployment. The lock channel may be on a bottom or a top of the supporting structure and the blade member and/or the pivot location may be driven into the lock channel by a spring or by the linear curvature and/or resilient flexibility of the deployment member or any other method known in the art. In some aspects, the deployment member may have a locking mechanism to secure the deployment member in position, and consequently secure the blades in either a retracted or deployed position. The locking mechanism may be actuated from a control located at or near a proximal end of the cutting tool. In these embodiments, support members 301, 306 may be optional.

The descriptions of the above support mechanisms are not intended to be exhaustive or to limit the invention to these precise forms of support disclosed. Other similar support mechanisms found to be technically useful in micro-devices may also be constructed. For example, the blades may use a switchblade-like mechanism for quick deployment with a counter-lever for collapsing the blades, or an electric motor to move the blades between a collapsed and extended position.

In some embodiments, for example, referring back to FIGS. 19A to 19C, the one or more blade members may be collapsed to and from the subdermal catheter device by way of an elongated opening 1906 on each respective side of the device. Elongated opening 1906 may be narrow enough that the opening and closing mechanism (e.g., as illustrated in FIG. 20) and internal area of the subdermal catheter 1801 are substantially protected from the outside. Enclosing the blade members within subdermal catheter 1801 during deployment enables the subdermal catheter to be inserted or withdrawn from a patient minimally invasively. A thin membrane (not illustrated) may be disposed on either or both sides of the opening such as to protect body fluids from entering into the subdermal catheter. In some embodiments the aforementioned membranes may overlap each other to provide better closure. The membrane can be made of any biocompatible material known in the art, e.g., any of the non-absorbable polymeric materials described above.

In some embodiments, the deployment member 2002 and the cutting blades 1902 are deployable from inside the body the subdermal catheter 1801. In these embodiments the blades 1902 may be deployed from a collapsed position from at or near the distal end 1803 of the subdermal catheter. In these embodiments, blades 1902 lie proximal each other inside hollow shaft 2001 and move to an outward position outside shaft 2001. The mechanics of blade members 1902 may be fully or partially exposed, thus not requiring the elongated openings 1906 along the side of the device. In yet further embodiments the elongated openings 1906 are not required, or the device may have partial elongated openings along the side of the cutting device.

In some embodiments the blade members will collapse in a way that they will substantially or completely overlap each other from end to end in the collapsed position. In other embodiments, where the blade members 1902 do not have the same pivot location, the blade members may collapse in a way that, when in the collapsed position, the blades are parallel and adjacent each other from end to end, e.g., as depicted in FIG. 21. The angle of deployment for each blade member may range between 0 degrees in a fully collapsed position to 90 degrees in a fully deployed position. Depending on the stability of the support beam or other locking mechanism it may be more preferable to allow a range between 45-75 degrees so that the device can maintain a narrow profile during deployment, and to maintain maximum stability of the blades during forward and reverse cutting action. Other angles, including an angle greater than 90 degrees are possible depending on various factors, including the skin-type or fat-density of the patient to be treated.

In the illustrated embodiment, device 102 has a handle 1804 located at or near a proximal end of the device for control and positioning the device 102. The handle 1804 preferably includes at least one control wire or rod for actuating the deployment and retraction of the retractable cutting blade 1802. The control wire extends through a lumen in the catheter from the handle 1804 to cutting blade 1802.

The device preferably has a deployment button or similar control 1805 located at the proximal end of the device which actuates the control wire and/or deployment member 2002 to move the blade members from a deployed and collapsed position. The deployment control may, for example, include a control rod or wire which extends through a lumen in a catheter. The lumen supports the lateral sides of the control wire thereby enabling the wire to exert a pushing force without buckling. Pushing the deployment control 1805 may collapse the blades while pulling the control may deploy the blades. In some embodiments pushing the control may deploy the blades while pulling the control may collapse the blades. In other embodiments pushing or pulling the control may do both. In some embodiments the cutting device may have a handle or a handpiece at a proximal end of the deployment member.

In some embodiments the device, including the subdermal catheter, will have a round cross-section, while in other embodiments the device will maintain a flat or oval profile. Generally, the cutting device preferably maintains a narrow profile such that it can be percutaneously inserted with minimal invasion to the treatment area. The nominal outer diameter of the cutting device typically ranges from 0.5 mm to 3.5 mm (25 gauge to 10 gauge), but can be smaller or larger depending on the tolerance of the patient. Each of the embodiments disclosed herein include a cutting blade.

Generally, the cutting blades have a nominal width from about 0.5 mm to 3.3 mm and a nominal thickness from about 0.1 mm to 0.8 mm, however, the blade can have a smaller or larger width and/or thickness depending on several factors, including the area to be treated or skin type. For the purposes of illustration, the blade members are substantially flat. Other embodiments may include blade members that are curved, bowed, or angled, or any other design which could be useful in improving the cutting action.

In each of the embodiments described herein the cutting blade includes a shaft portion and a cutting portion where the shaft is defined as that portion which does not contribute to the tissue cutting and the cutting portion is the active and/or sharpened portion of the cutting blade. The length of the cutting blade may vary depending on the specific application and the material properties of the blade. Generally, the longer the cutting blade the more difficult it is to prevent bending or deflection (which is undesirable).

In each of the embodiments described herein the blades may have a sharp or a blunt edge to separate the fibrous septae. In some embodiments the blades are double sided thereby having an edge on each of the longer sides. In other embodiments the blades are single sided. In some embodiments the distal and/or proximate ends may have a sharp edge and/or may come to a point. For instance, the end proximal to the pivot location may be pointed such that the pointed end near the pivot location can be used as a spear to puncture the skin when inserting the device into a treatment area.

One or more of the blade members 1902 may be an RF electrode (monopolar or bipolar). If the blade members are RF electrodes they may be electrically insulated from one another by providing an electrically nonconductive coating on portions of the blade members 1902.

The term cutting blade as used herein should be understood to include an RF electrode, harmonic scalpel or the like useful in cutting tissue in a minimally invasive manner. Thus the cutting blade may or may not include sharpened edges and/or a sharp tip. The term cutting blade may be a single blade having one or more cutting surfaces and also encompasses two or more blades. An RF electrode-cutting blade may be monopolar or bipolar such as such terms are commonly understood in the medical device arts.

Figure 21A:
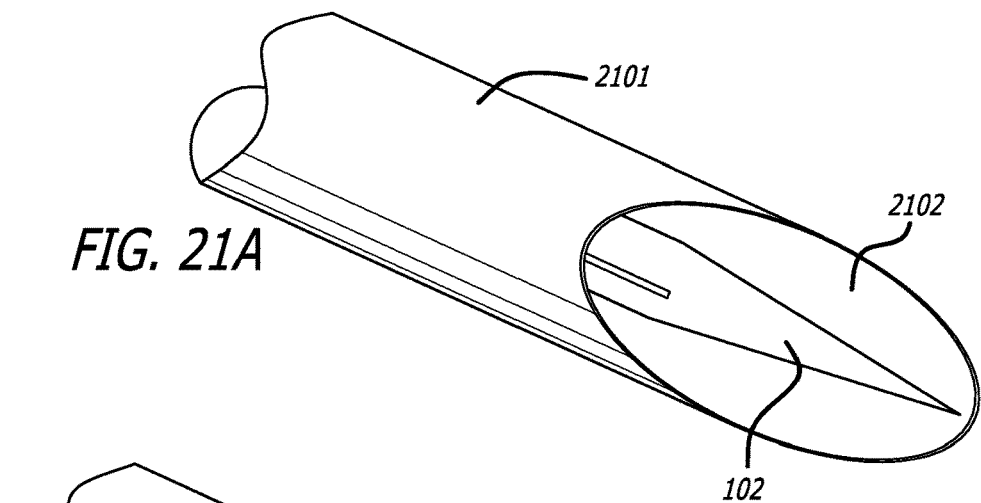
FIGS. 21A and 21B depict embodiments of the cutting tool.
Figure 21B:
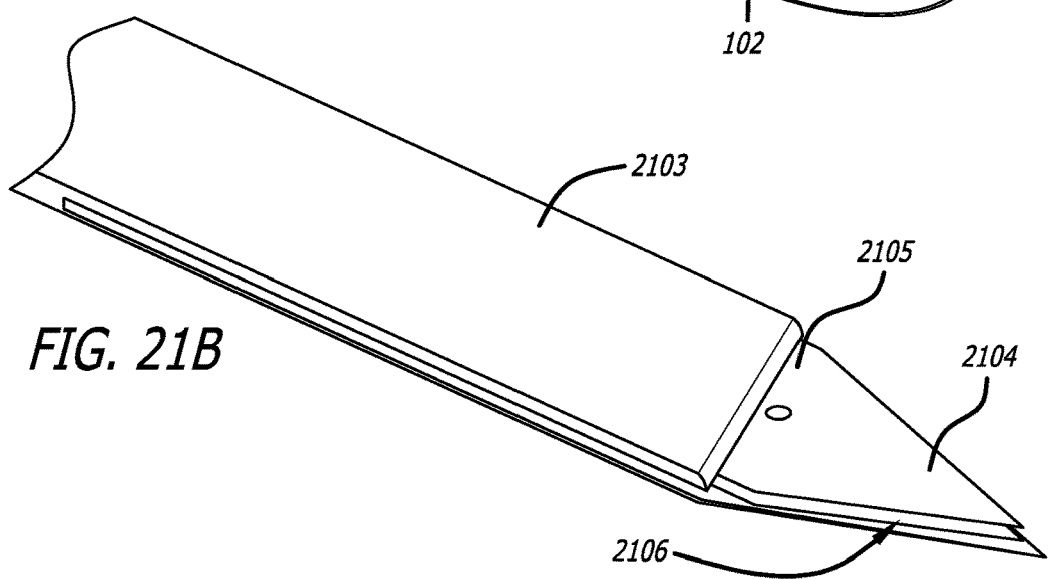

As depicted by FIGS. 21A and 21B, in some embodiments, subdermal catheter 1801 may include an outer housing 2101 that is part of, or associated with, the cutting tool and/or other blade mechanisms herein described. In some aspects subdermal catheter 1801 may also include an outer housing 2101 that is part of, or associated with, a mesh deployment applicator (described below). Subdermal catheter 1801 may be used in conjunction with a handpiece 100. Moreover, the vacuum assisted handpiece supports the cutting tool thereby facilitating a planar dissection parallel to the dermis. In one embodiment, the cross sectional profile of the subdermal catheter is substantially flat so as to maintain a low profile when inserted between the skin and fat layers. In other embodiments the cross sectional profile of the subdermal catheter may be round, square, triangular, hexagonal or any other shape configured for the embodiments described herein.

In one embodiment, cutting device 102, is enclosed in a hollow shaft 2101 which includes a hypodermic needle or skin penetrating means 2102 located at the distal end of the shaft. Needle 2102 is sufficiently rigid to allow skin perforation. In the illustrated embodiment the shaft 2101 of hypodermic needle has a nominal inner diameter sufficient to enclose cutting tool 102, including the blades and their respective deployment mechanism. In some embodiments, hollow shaft 2101 includes at least a portion of subdermal catheter 102. In one embodiment, as depicted by FIG. 21B, the penetration means may include a sheath or slotted needle 2103 such that the end of the blades 2104 protrude from a distal end 2105 of the device and form at least a portion of the penetrating means. Each blade may have a pointed proximal end such that when the blade is collapsed the combination of blade members forms a cutting edge 2106. In a further embodiments the retractable cutting blade members may ride atop supporting structure 2103 near its distal end.

Figures 22A, 22B, 22C, 22D:
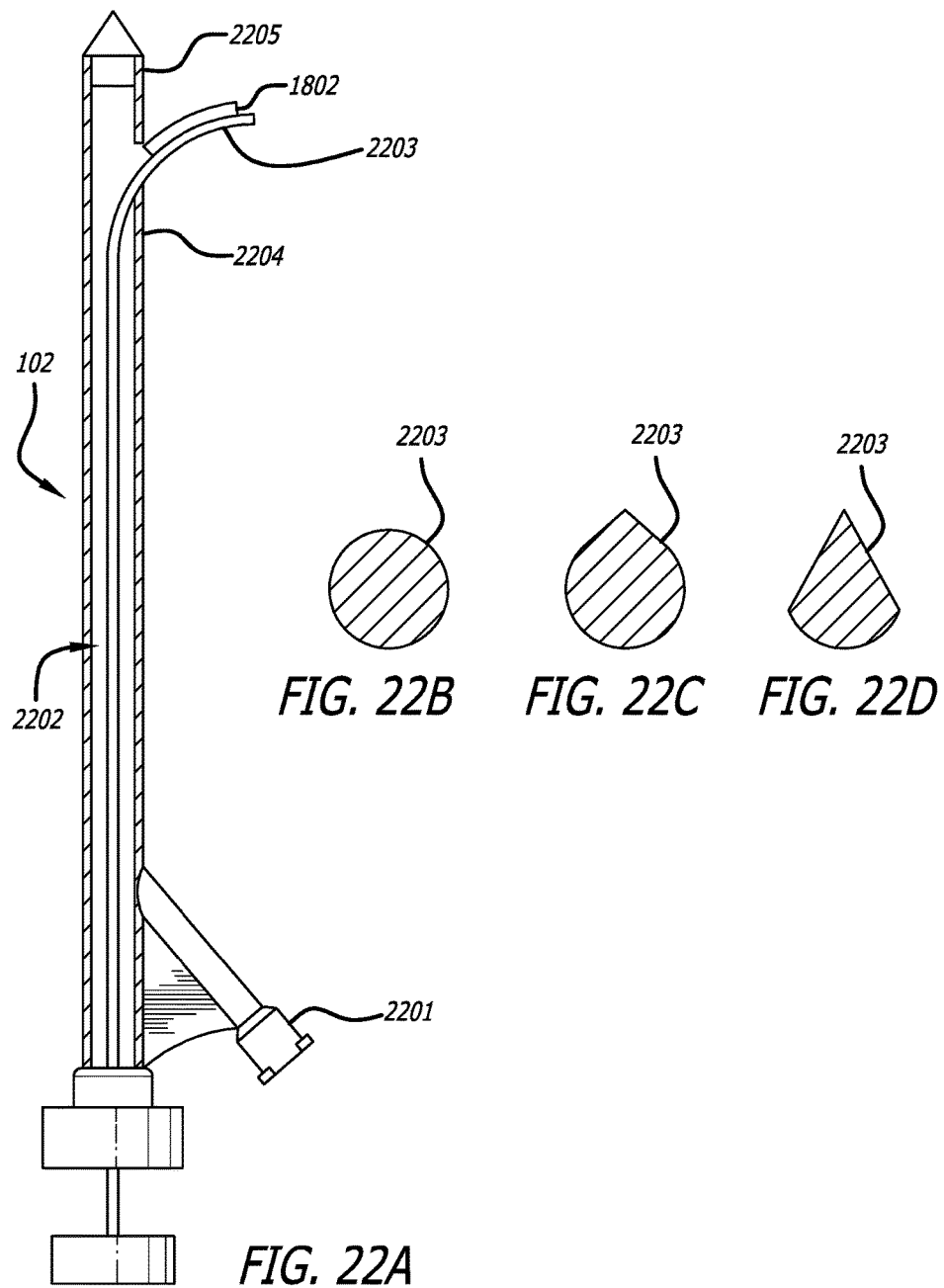
FIGS. 22A through 22D depict another embodiment of the cutting tool.

FIGS. 22A through 22E illustrate a further embodiment of cutting tool 102 for creating a plane of dissection which cuts or resects the fibrous septae. FIG. 22A depicts an embodiment of the cutting device including a fluid injection port 2201 in fluid connection with a lumen 2202 in the subdermal catheter. Fluid injection port 2201 may be used for injecting a treatment fluid such as an anesthetic and/or a vasoconstrictor into the cutting area before, during, or after the tool is being used in the treatment area. A thin tube may be disposed inside the subdermal catheter (or a lumen may be defined in a wall of the catheter) along with the other mechanics of the cutting device. The thin tube (or lumen) can then be attached to a fitting at the proximal end of the subdermal catheter for fluid connection with a syringe, syringe pump or other injection mechanism known in the art. In certain embodiments the treatment fluid can be injected using the subdermal catheter. The treatment fluid may include a local anesthetic or pain relieving fluid, an antibiotic, or a combination of treatment fluids useful in similar medical procedures. In some embodiments it may further be desirable to substitute port 2201 with an aspiration port operably connected to a vacuum source to aspirate fluid and minimize the accumulation of fluid.

FIGS. 22B through 22D illustrate how the wire may be sharpened or formed to a blade. It is possible for blade 1802 to be made of a sharpened wire 2203, where the wire diameter is from 0.5 mm to 3.3 mm and, as best seen in FIG. 22D becomes a non-circular cross-section after sharpening. FIGS. 22B-22D show how the cross section of the wire changes from circular (FIG. 22B) to non-circular (FIGS. 22C and 22D) as the wire is sharpened. In some embodiments, the pre-sharpened wire may also have rectangular cross-section, and one or more of the edges of the rectangle may be sharpened (not illustrated). FIG. 22A shows the wire implementation, where the wire is deployed to one side 2204 and exits proximal of the distal end 2205 of cutting tool 102. Preferably, the location of wire 2203 exit may range from distal end 2205 to about 3 cm proximal the distal end of the catheter. In one embodiment, the sharpened aspect of the wire faces distal end 2205 of cutting device 102, and the cutting function occurs when the device is pushed in the distal direction. In a further embodiment, the sharpened aspect of the wire faces toward the proximal end, opposite distal end 2205, and the cutting function occurs when the device is pulled back from the distal position. Optionally, both edges of the wire may be sharpened for cutting in either direction. Cutting wire 2203 may also be optionally gradually deployed in a series of cutting sweeps, where with each sweep the wire is deployed further to achieve a wide dissection plane. FIG. 22B represents a non-sharpened portion of the wire, FIG. 22C represents a semi-sharpened portion, and FIG. 22D depicts a fully sharpened end for cutting when deployed from device 102. Port 2201 may dispense for dispersing a fluid into the treatment area or remove tissue from the treatment area as the device is used to cut fibrous structures and/or destroy adipose tissue.

Sharpened cutting wire 2203 may also form an RF cutter include an RF (radiofrequency) electrode connected to an RF amplifier (see FIG. 16B). As previously described embodiments, insulating coating may be applied to the length of the electrode, leaving only a relatively small exposed (active) portion at or near the distal end of the wire. Wire 2203 may be used with or without activating the RF energy. Thus the RF may assist in the cutting. RF energy may be supplied to wire 2203 in either a cutting or coagulation mode as desired. It may be desirable to activate the RF energy only after wire 2203 is positioned subdermally at the desired depth to prevent or minimize injury to the skin. Moreover, the wire electrode 2203 may be used to confirm resection by sweeping the unpowered wire electrode through the cutting plane. RF amplifier 1609 supplies RF energy to the probe 2203 or any of the other RF probes disclosed herein.

One method of using the present embodiments is directed to providing a handpiece and cutting tools (described above) configured to minimally invasively create a plane of dissection. The handpiece and cutting tools may be suitable for cutting fibrous structures which may lie in the interface between the dermis and the subcutaneous tissue. The handpiece of the present invention supports the cutting tool and enables the user to create a plane of dissection at a precisely defined depth and, if desired, inject or insert an implant into the treatment area. If desired, the area of treatment may be injected with fluids comprising beneficial agents. It should be understood that any of the cutting devices disclosed in this disclosure may be used with any of the injection and insertion methods and devices disclosed herein. The depth of the plane of dissection may be defined by the orthogonal distance from the tissue apposition (tissue facing) surface of the top wall to the tool insertion conduit.

Throughout this disclosure the term mesh will be used to refer generally to any generally planar foreign body sheet of material which is implanted into subcutaneous tissue. The mesh may be composed of sutures, filaments, fibers, fibrous structures, scaffolding, quills or the like. The mesh used in any of the embodiment described herein may be bioabsorbable such that the mesh dissolves or is otherwise absorbed by the body over time. Each of the embodiments disclosed herein may be used to treat targeted areas, such as the upper leg below the buttocks where cellulite is most visible.

The mesh may be implanted under the skin in order to promote increased connections between the skin and the fat and increase the durability of the reduced dimpling cellulitic appearance. In one embodiment the mesh may be made of any of a range of materials including but not limited to polypropylene, nylon, collagen, polymers of polyester, glycolide, or other suture materials. The mesh may either be absorbing or non-absorbing. The thickness of the mesh can vary from 0.01 mm to 0.05 mm and the area of the mesh may range from 1 mm to 100 mm. The mesh may be formed in squares, circles, rectangles, or irregular shapes that are custom cut to the patient needs.

In the embodiments disclosed herein it is preferred that the mesh include a plurality of pores to promote the ingrowth of tissue. More particularly, the pores preferably have a pore size ranging from 50 µm to 5 mm such that it can become ingrown with tissue at that site to serve a useful therapeutic purpose. The pore size is patient dependent, and different pore sizes will be indicated for different patients. The goal pore size is as small as possible to create a smooth appearance and a maximum amount of fibrous attachment through the mesh; however, large enough to promote rapid attachment of cells and maintain a highly flexible and natural looking appearance.

In one embodiment, the implantable mesh is reticulated, such that it is comprised of an interconnected network of pores, either by being formed having a reticulated structure and/or undergoing a reticulation process. This provides fluid permeability through the implantable mesh and permits cellular in-growth and proliferation into the interior of the implantable mesh. In further embodiments the mesh may include quills, sutures or other structures which bind into the surrounding tissue.

The mesh may be textured or treated on one side to promote binding to either the skin or the fat side. The mesh may be textured or treated on both sides to promote binding to both the skin side and the fat side. The treatment on the mesh may be a growth-promoting chemical to encourage rapid in-growth into the mesh from the body, and/or biologically acceptable glue may be used to bind one or both sides of the mesh.

The mesh may be composed of stiff materials or flexible materials. Preferably, the mesh is highly flexible and easily contours to any curvature. The mesh may be made of component material that is elastic or non-elastic. In addition to being flexible, it may be desirable for the mesh to be composed of elastic materials. Moreover, according to one embodiment the mesh may be attached to tissue on both upper and lower planar sides (parallel to the dermis) thereof. Attachment of the mesh may be by way of adhesive glue or the like, sutures, staples, barbs, hooks or the like, In the case of non-elastic material, the mesh will likely need to be bound on one side and free to move on the other side. Upon implantation, the mesh reduces dimpling by creating a substantially high density of attachments (new fibrous) between the skin and the fat, thus reducing the appearance of dimples and heterogeneity on the skin surface. Over long term, e.g., 3-6 months after implantation, the mesh promotes more fibrous tissue which further reduces the appearance of cellulite.

The implantable device may also include a biocompatible, reticulated (i.e. resembling or forming a net), resiliently compressible elastomeric material that is generally flat, flexible, and can recover its shape and most of its size after compression. In some of these embodiments the elastomeric material may be comprised of a bioabsorbable polymeric material.

In some embodiments, the implantable device (frame and/or mesh) has a resilient compressibility that allows the implantable device to be compressed under ambient conditions, e.g. at 25° C., from a relaxed configuration to a first, compact configuration for in vivo delivery via a delivery-device and to expand to a second, working configuration, in situ. The implantable device can be suitable for long-term implantation and having sufficient porosity to encourage cellular in-growth and proliferation, in vivo. Preferably, the implantable device is constructed such that it may be encapsulated and ingrown within the treatment area, and does not interfere with the function of the regrown cells and/or tissue, and has no tendency to migrate.

In some embodiments, the period of implantation will be at least sufficient for cellular in-growth and proliferation to commence, for example, in at least about 4-8 weeks. In these embodiments, the device may be sufficiently well characterized to be suitable for long-term implantation by having been shown to have such chemical, physical and/or biological properties as to provide a reasonable expectation of biodurability, meaning that the device will continue to exhibit biodurability when implanted for extended periods of time, e.g. the device may include a biocompatible elastomer that may be considered biodurable for the life of a patient.

Furthermore, in certain implantation applications, it is anticipated that implantable device will become in the course of time, for example, in 2 weeks to 1 year, completely absorbed, encapsulated by tissue, scar tissue or the like, or incorporated and totally integrated into, e.g., the fibrous repaired. In some embodiments the implantable device is completely biocompatible such that the probabilities of biochemical degradation or release of undesired, possibly nocuous, products into the host organism may be attenuated if not eliminated.

As shown by FIGS. 23A through 23E, the system may include a mesh deployment applicator 2301 to deploy a fibrous mesh 2302 through a single needle hole in a dermis to create a highly fibrous layer directly or through wound healing processes. The implantable mesh may be self-expandable, and is generally flat, flexible, and can recover its shape and most of its size after compression. In other embodiments mesh 2302 may be detachably coupled to a resiliently compressible self-expandable frame (not illustrated). In a first embodiment, implantable mesh 2302 is preferably disposed at or near a distal end 2303 of deployment applicator 2301. The applicator is inserted percutaneously through the skin using a subdermal catheter such as that described above, or by itself through a hole in the skin, to deploy the implantable mesh located at or near its distal end to a treatment area in the subdermal fat or in the layer between the subdermal fat and the skin. It should be noted that the mesh applicator may be combined in a kit or a system with any of the dissection devices and/or the vacuum-assisted hand piece described herein. Specifically, the mesh applicator may be included with handpiece 100 to be deployed through conduit 213. The dissection devices disclosed herein may be used to create a subdermal pocket sized to receive the mesh.

Figure 23A:
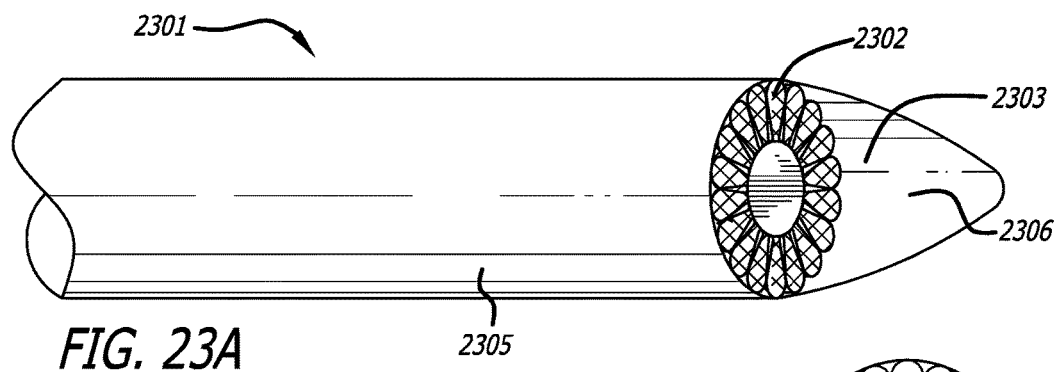
FIGS. 23A through 23E depict a first embodiment of a mesh deployment applicator.
Figure 23B:
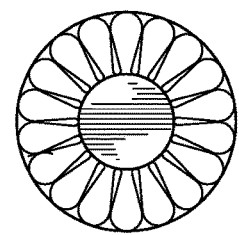
Figure 23C:
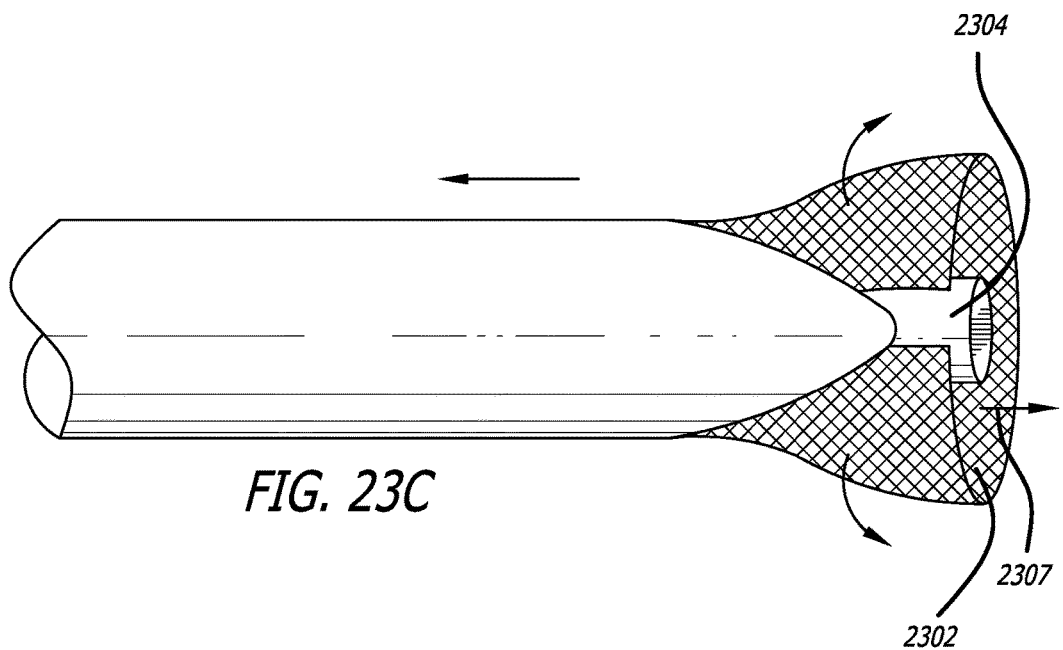
Figure 23D:
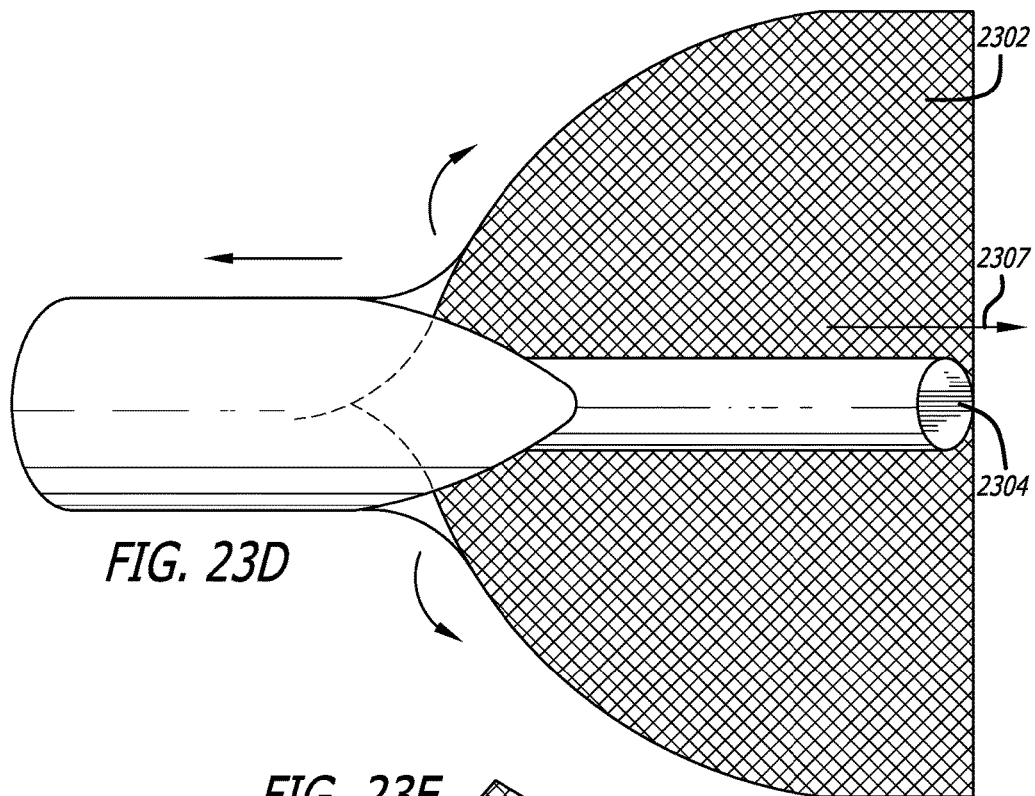

As depicted in FIGS. 23A through 23C, implantable mesh 2302 can be folded and/or stretched on a guide-wire (not illustrated) or on an internal sheath 2304 (that may also harbor a guide wire) in order to attain a cross section narrow enough to be preloaded into a second sheath 2305, this external second sheath includes a hollow portion 2306 of deployment applicator 2301, or similar delivery catheter associated with deployment applicator 2301.

In one embodiment, depicted by FIGS. 23A through 23B, the implantable device may be folded onto internal sheath 2304 and disposed within external sheath 2305, and is deployed when the device becomes unrestrained by external sheath 505.

In other embodiments, depicted by FIG. 23C, implantable device 2302 may be rolled onto itself and disposed within external sheath 2305. Implantable device 2302 may be deployed by removal of the external sheath 2305. For example, the apparatus may be deployed by pushing internal sheath 2304 or guide wire in a distal direction 2307 out from device 2301.

In some embodiments, deployment applicator 2301 may include a restraining member that is actuated by heat, electricity, or other means known in the art to release the mesh apparatus from its collapsed and restrained position to its relaxed and expanded position.

In one embodiment external sheath 2305 may include the subdermal catheter 1801 previously described or may be positioned within subdermal catheter 1801 along with cutting blade members 1902. In this embodiment cutting tool 102 includes a hollow end depicted in FIG. 21A.

Preferably, the collapsed applicator has a sufficiently narrow profile to be threaded through deployment applicator 2301 or subdermal catheter, previously described. The applicator is preferably inserted percutaneously through the incision made by cutting tool 102, or other hole or incision in the skin created by the various dissection devices described herein. While applicator 2301 may be used with handpiece 100, applicator 2301 can be deployed through any needle hole in a dermis. In one embodiment, the thickness of the implantable device when in a collapsed form, i.e., when folded, rolled, and/or stretched to be accommodated by the applicator, has an outer diameter of from about 0.65 mm to about 2.2 mm. Suitable delivery sheaths 2305 can have an outer diameter from about 1 mm to about 3.3 mm. In other embodiments, the outer diameter of the deployed device or delivery sheaths can be greater or smaller depending on the configuration of the dissection needle.

Figure 23E:
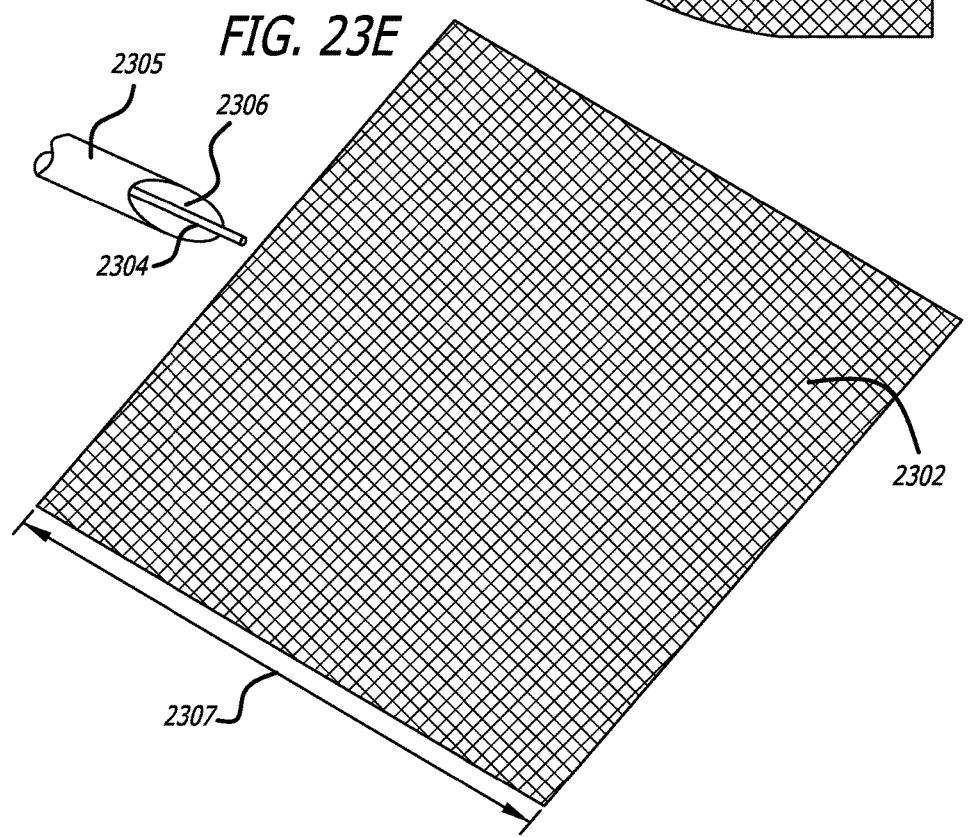

As illustrated by FIG. 23E, mesh 2302 (with or without a corresponding frame (not shown)), when in a relaxed and expanded form, has a length and/or width 2307 typically in a range from about 1 cm to about 5 cm. In other embodiments, the range may be up to 10 cm or higher depending on the size and configuration of the deployment applicator and dissection needle. Mesh 2302 is depicted as substantially square, but can be any shape suited to be placed in the subdermal fat or in the layer between the subdermal fat and the skin. For instance, and without limitations, the fully expanded mesh can be circular, rectangular, triangular, hexagonal, or even irregularly shaped.

Figure 24A:
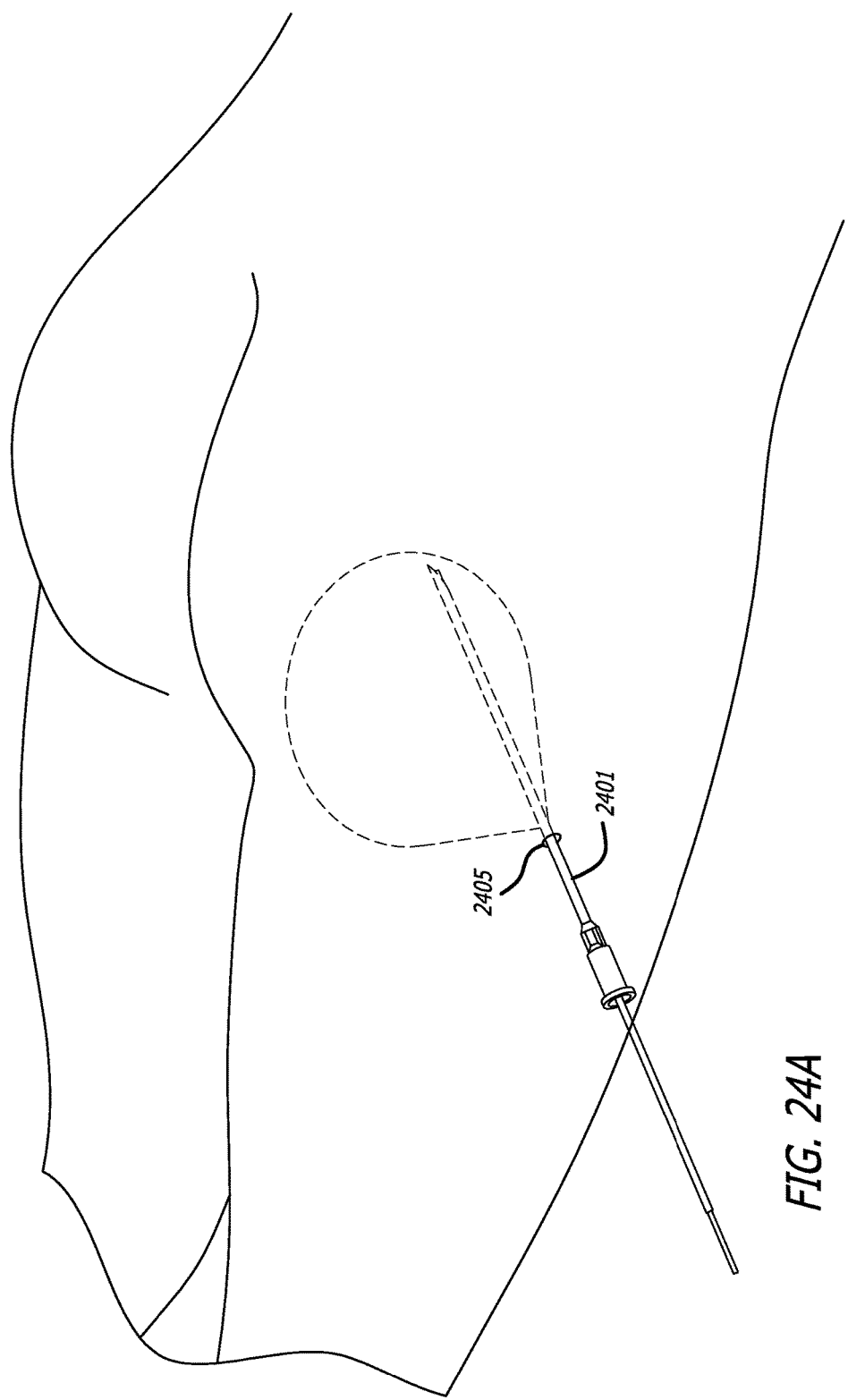
Figure 24B:
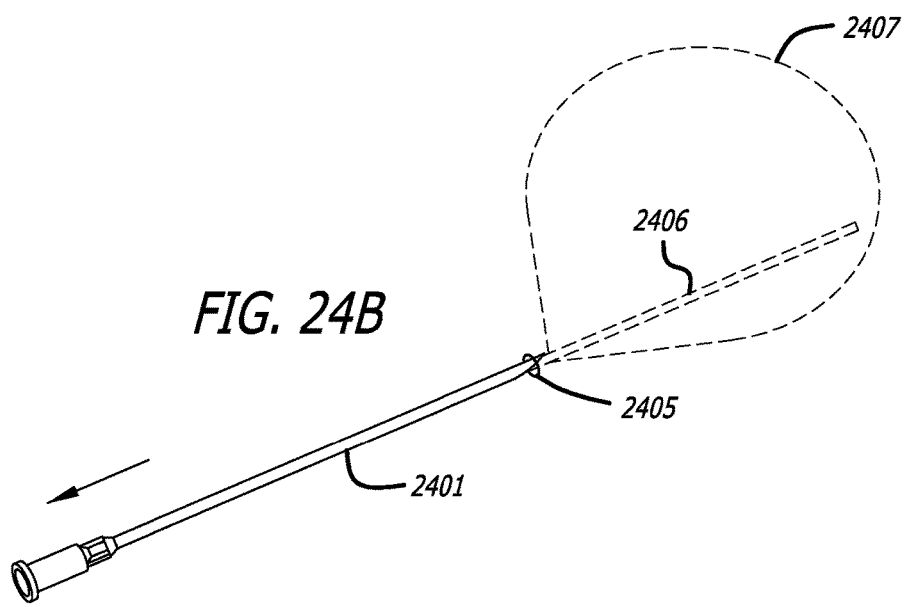
Figure 24C:
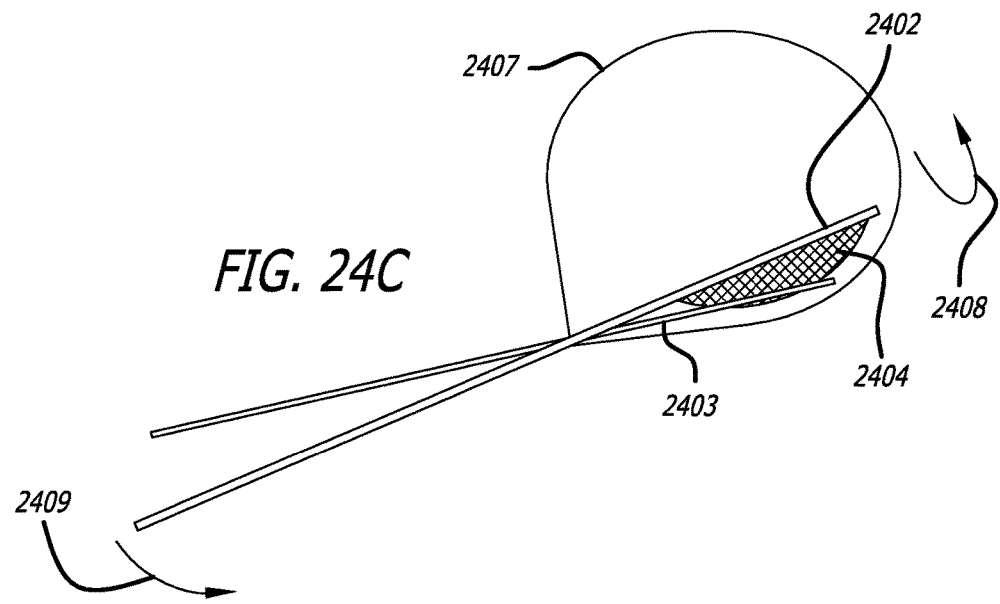
Figure 24D:
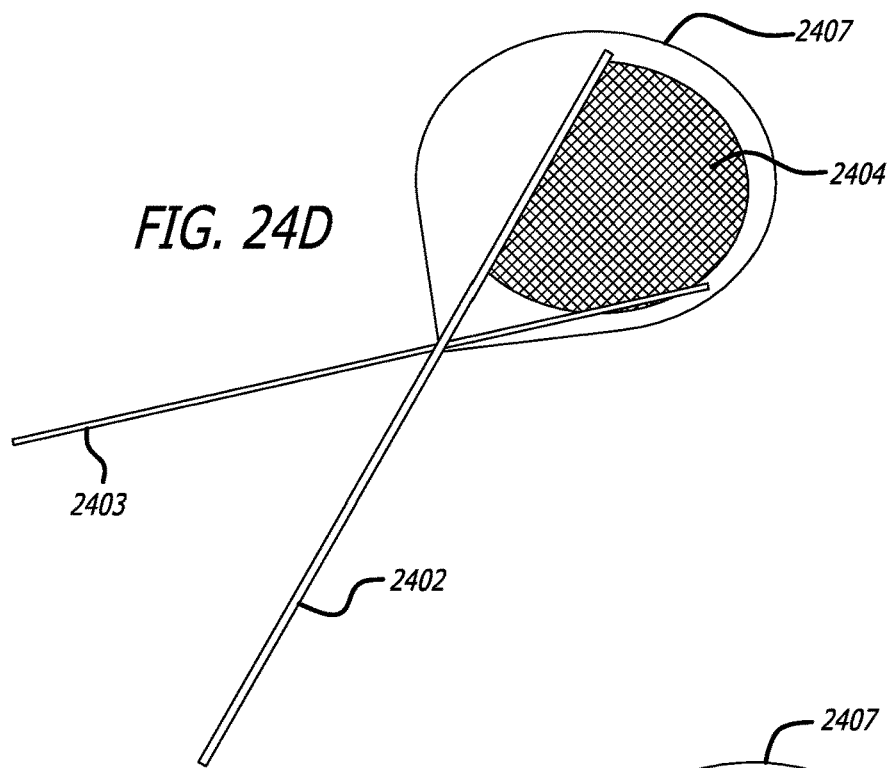
Figure 24E:
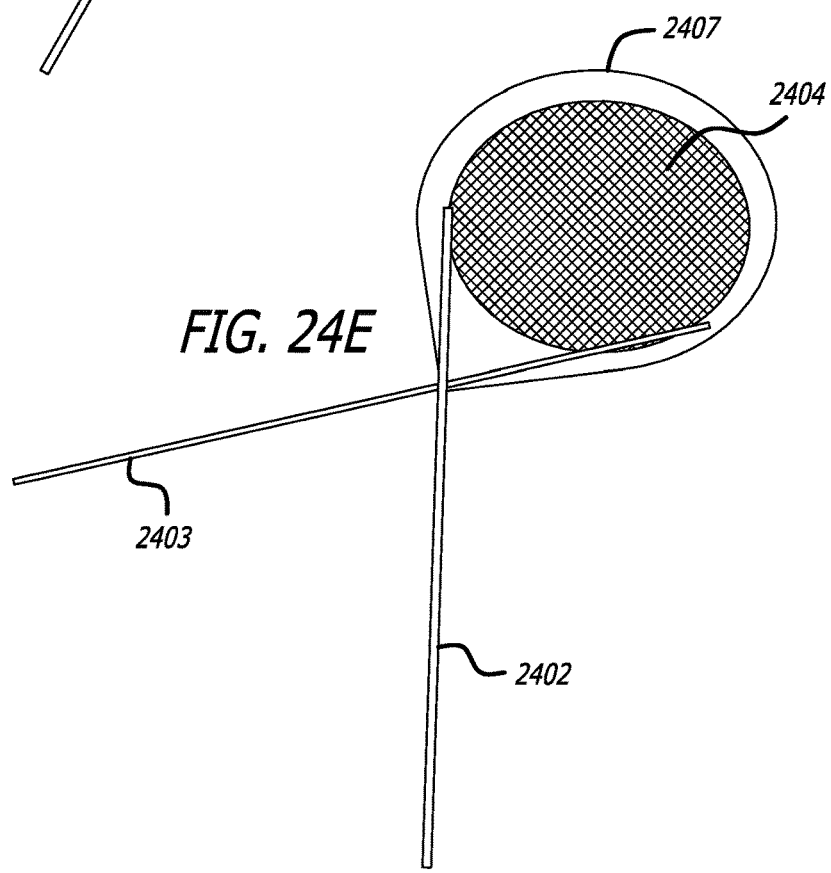

FIGS. 24A through 24F depict a second embodiment of a mesh deployment applicator. In this embodiment, a sheath 2305 may include or be interchangeable with an introducer needle 2401, and a guide wire may be omitted. A deployment shaft 2402 and keeper rod 2403 are disposed inside introducer needle 2401. Mesh 2404 is configured to be furled (i.e., rolled up) around shaft 2402 and keeper rod 2403. Introducer needle 2401 (with mesh inside) may then be inserted through an entry wound 2405 created by tool 102. After insertion, needle 2401 slides off over a proximal end 2406 of shaft 2402 and keeper rod 2403, leaving the furled mesh 2404 positioned with subcision region 2407. Shaft 2402 is simultaneously rotated about its longitudinal axis 2408 to un-furl mesh 2404, and pivoted about the skin-entry point 2405 to pull mesh 2404 across subcision region 2407. Keeper rod 2403 is maintained in a fixed position as mesh 2404 is un-furled, so as to anchor the edge of mesh 2404 at the desired location within subcision region 2407. As shown by FIG. 24C, shaft 2402 pivots 2408 about skin-entry point 2405, aided by the dissection handpiece 100 (discussed above). As mesh 2404 continues to be un-furled, a greater portion of mesh 2404 is deployed across treatment area 2407. FIG. 24E depicts mesh 2404 in a fully deployed position. As depicted in FIG. 24F, after deployment, keeper rod 2403 and shaft 2402 can then be withdrawn through entry point 2405, leaving mesh 2404 in the desired position within subcision region 2407. In one embodiment, a longitudinal slit 2409 is present on a distal end 2410 of shaft 2402 and keeper rod 2403. Mesh 2404 is secured when mesh 2404 is wrapped around shaft 2402 or keeper rod 2403, however, slits 2409 are open on distal end 2410, so when shaft 2402 and rod 2403 are withdrawn as illustrated, mesh 2404 slips off the end of shaft 2402 and rod 2403.

With reference to FIG. 16B, in some embodiments the system includes an energy device 1608. In accordance with these embodiments the insertable tool and/or handpiece may be configured to apply energy such as RF, ultrasound, or microwave energy to the tissue before or after the mesh has been inserted into the treatment area. Although not specifically illustrated, it should be understood that an appropriate energy source 1609 (ultrasound amplifier, RF amplifier, microwave) will need to be operably connected to handpiece 100. In some embodiments energy source 1608 may be used to create damage sites along the mesh that will heal as fibrous structures, and/or to shrink the mesh and create a tightening of the subcutaneous tissues. Energy device 1608 may include a microwave, conductive heat, ultrasound, or RF. In some embodiments the energy may also be applied to shrink the self-expanding implantable device after it has been deployed under the skin.

With reference to FIGS. 9B and 9C, a physician first applies a reference mark 904 to the dermis to identify an area for treatment, and handpiece 100 is positioned on an outer portion of the skin 903 to be treated. Handpiece 100, including transparent cover 206, is subsequently placed over mark 904 on dermis 903 and a vacuum is applied. Mark 904 is then suctioned against the upper tissue apposition surface 203 such that mark 904 on dermis 902 is visible through the clear top portion 206 of handpiece 100. A reference feature 905 on handpiece 100 indicates the region that dissection will occur, and the physician verifies that mark 904 falls within the dissection region 902. FIG. 9C depicts handpiece 100 used in conjunction with a NOKOR™-like subcision device capable of cutting septae and infusing a tumescent fluid, however, any cutting feature or device disclosed above may be used with this embodiment.

An embodiment of using the device includes percutaneously inserting a cutting tool through the epidermis of the skin and into the subcutaneous tissue layer or in the layer between the subcutaneous tissue and the skin.

(1) A first step, depicted by FIGS. 1A and 1B, includes capturing the tissue to be treated into the recessed portion of the handpiece. In some embodiments this entails applying a manual pressure or force on the handpiece. In other embodiments this entails using a vacuum enabled handpiece to bring the tissue into contact with the recessed portion of the tissue apposition surface. Suction from a remote vacuum source 1606 (FIG. 16B) is supplied to one or more ports 208 (FIG. 2) in the handpiece to pull the tissue into a recess bounded on top and side surfaces. Precise depth control, where depth is measured orthogonally downward (into the tissue) from the dermis is believed to be an important factor in achieving consistent and uniform results. In other words, it is important to create a planar lesion at a fixed depth below the dermis. FIG. 2 depicts a portion of subcutaneous tissue 205 disposed within the recessed area of the handpiece.

(2) A deployable tool (102, 303, 1001, 2401) is then placed into and through the conduit in a side of the handpiece, such that the tool is placed in a precise tissue depth in the subcutaneous tissue or in the layer between the subcutaneous tissue and the skin. The tool may have a collapsible blade or may pierce the skin like a bayonet. In one embodiment the tool may be any cutting tool as described in previous paragraphs. In another embodiment the tool may be a hypodermic needle for anesthetic fluid administration. In another embodiment the tool may be a specialized larger diameter hypodermic needle, or subdermal catheter, configured to allow deployment of a cutting tool and/or other deployment devices through its center.

(3) Once in place, the cutting tool is actuated. In some embodiments, actuation of the cutting tool entails deployment of the cutting blades. In some embodiments, the cutting blade is simply inserted percutaneously through the dermis at a desired depth. In some embodiments, the cutting toll is an RF needle. The RF needle may be provided with a sharp tip for penetrating the dermis. In some embodiments, the tip may be blunt or beveled. Actuation of the RF needle entails supplying RF frequency current from an RF amplifier to the needle in either a cutting mode or in coagulation mode. To avoid damaging the dermis, it is desirable to supply the minimum amount of energy during cutting to avoid or minimize heating of the dermis.

Optionally, one or more cutting blades of the cutting tools are then deployed from the cutting tool. In one embodiment, deploying the cutting blades include actuating a control at a proximal end of the tool. The control may be actuated by a simple switch, lever, or control rod which is either pulled, turned or pushed to control actuation of the cutting blades. In some of the embodiments the cutting tool is not collapsed thus the un-collapsed cutting blade is percutaneously inserted and there is no need to deploy the cutting tool.

(4) The tool is then manipulated to create a dissection plane and sever, where necessary, fibrous structures 220 (FIG. 2) between the skin and the subcutaneous tissue at a precisely defined depth maintained by the handpiece and tissue apposition surface. In one embodiment the tool cuts on the reverse stroke as it is pulled back (retracted) 227 to sever fibrous structures 220. In another embodiment, the tool cuts on the forward stroke as the tool is deployed and pushed forward 228 to sever the fibrous structures. In a further embodiment the cutting tool is optionally moved in a forward and reverse direction, i.e. reciprocated. In a further embodiment conduit 213 is configured to provide some side-to-side movement parallel to the surface of the skin (FIG. 2B). In other words, the conduit is somewhat larger gauge than the cutting tool, thereby enabling the cutting tool to be pivoted in an arc from side-to-side. In a yet further embodiment advancement and sweeping of the tool during cutting is microprocessor controlled.

(5) After completion of the dissection and cutting of the fibrous septae, the tool is collapsed and/or removed from the tissue and the handpiece. Optionally, the cutting blades are then retracted by any of the means described for deploying the blades. Or as described above, in some embodiments there is no step of deploying or underdeploying the blade. In one embodiment the blades are retracted by moving the actuator in the opposite direction as it was moved to deploy the blades. In another embodiment the blades are retracted by moving the actuator in the same direction. As noted previously, some of the cutting tools may not utilize collapsing cutting blades in which case the cutting tool is simply withdrawn. Optionally, the users may sweep the cutting tool to verify a clean dissection of the fibrous structures. If resistance is encountered when sweeping the cutting tool then steps 4 and 5 may be repeated.

In some embodiments, a treatment fluid may be injected into the cutting area at or between any step of cutting inside the tissue. The fluid may be actively injected, for instance by using a syringe, or may be drawn into the pocket from an external reservoir by the reduced pressure created by a vacuum applied to the handpiece. The fluid may perform a number of functions, as described above in paragraph 00110.

The treatment fluid may also be injected prior or after deployment of the blades and/or cutting steps. If the cutting tool includes the application of energy the treatment fluid may be selected to enhance the delivery of energy. For example, if the cutting tool is an RF electrode, the treatment fluid may include saline or like conductive fluid to prevent charring of the tissue. It may be desirable to control such energy based on the measurement of an applicable parameter such as tissue impedance or temperature. As someone with ordinary skill in the art would realize, such feedback control would be comprised of a microprocessor based algorithm. As used throughout this disclosure, any reference to applying energy should be understood to define the application of one of radiofrequency (RF), ultrasound, microwave, or thermal energy.

As in previous embodiments, and as depicted by FIGS. 26A and 26B, and with further reference to FIG. 10A, a treatment fluid may be inserted prior to or after the dissection process. Injection device 1004 is inserted into the guide track 302 preferably at entry point 1008. The tissue to be treated is disposed in recessed area 105 as previously described. Needle 1001 may then be easily guided through conduit 213 and entry hole 214 and into the tissue by moving injection device 1004 along any of radial tracks 1005 toward handpiece 100. For example, injection device 1004 is first moved down the central channel in a forward direction 2601 to directly insert needle 1001 into the tissue. The treatment fluid is then injected using needle 1001 manually using syringe 1003 or, in some embodiments, by a microprocessor driven injection pump (e.g., FIG. 15). After the fluid is injected needle 1001 is removed by reversing direction along track 1005. Injection device may then be rotatively moved in an arc 2602 along cross-track 1007 to be positioned in an alternate radial track 1005. Injection device 1004 is then moved a second time down radial track 1005 in a forward direction 2603 to insert needle 1001 into a further location within the treatment area. Needle 1001 passes through the same entry point 214 while the widened shape of conduit 213 allows repositioning of needle 1001 with respect to rotational angle 2602 and radial tracks 1005. The process may then be again repeated for the third track 1005, or as many times as is determined to be necessary by the treating physician. In some embodiments, needle 1001 is a 22 gauge multi-holed, single-use needle. Needle 1001 includes multiple holes along its sides so as to, once it is fully inserted, saturate the tissue along its injection path. Injecting the fluid along the paths set by the disclosed injection guidance track, thus allows a fluid, such as an anesthetic and/or a vasoconstrictor, to fully saturate the treatment area while providing precise needle guidance and specific depth. It has been found that the method reduces the number of needle sticks necessary to infuse the area to be treated, increases anesthesia effectiveness, and substantially minimizes pain. Because the handpiece remains in the same position between fluid injection and dissection (subcision) locality of anesthesia relative to dissection is assured, and the swappable guidance track provides rapid switching between medicament delivery and dissection and vice versa so as to increase fluid retention throughout the process. Furthermore, the modularity of the platform and guidance track ensures that the process is repeatable and scalable.

The device allows for three-dimensional control of treatment fluid delivery and dissection of subcutaneous tissues, not realized by present art. The device typically controls a depth of between 4 mm and 20 mm below the surface of skin; however, a depth lower than 4 mm or greater than 20 mm is contemplated. The range of motion in the lateral direction is controlled by the effective length of the needle or blade or other cutting device, however, typically encompasses an area of between 2 mm and 50 mm in either direction. As the cutting device is disposed further into the subcutaneous space larger areas are achievable.

Figure 27A:
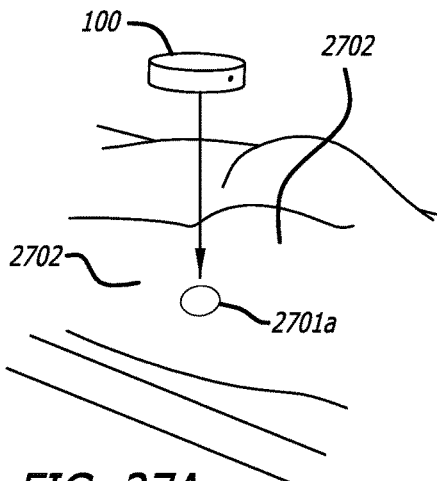
FIGS. 27A through 27D depict a method of using the handpiece and cutting tool on a dermis, including partially overlapping adjacent treatment areas.

It is generally recognized that a large treatment site heals more slowly than a series of smaller treatment sites. Moreover, the larger the treatment site the greater the risk of seromas, uneven healing, fibrosis, and even skin necrosis. Turning to FIGS. 27A through 27D, this problem is addressed, in one embodiment, by utilizing a adjustable depth feature (e.g., FIGS. 12, 13, 14). Each treatment site 2701 is an island surrounded by tissue 2702 which has not been treated (the fibrous septae have not been severed at the same plane). As depicted by FIG. 27A, handpiece 100 is used to treat a first treatment area 2701. In some embodiments, after the tissue within the first treatment site is treated, the handpiece can be repositioned on a different treatment area 2701 at the same, or at a different or alternating depth as, for example, in a checkerboard fashion.

Figure 27B:
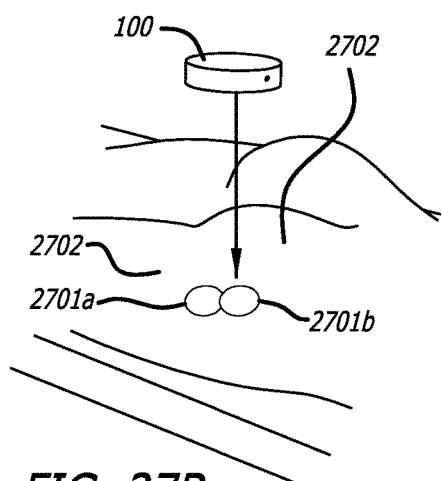
Figure 27C:
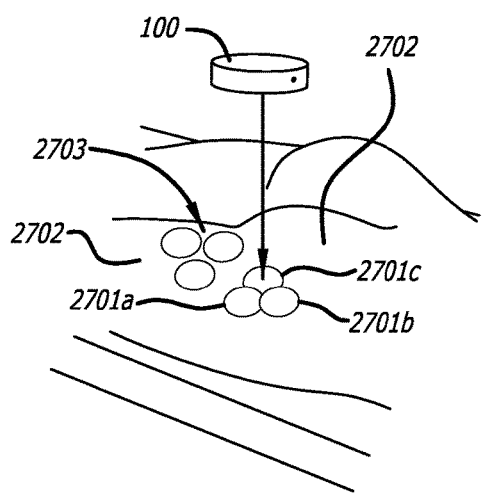
Figure 27D:
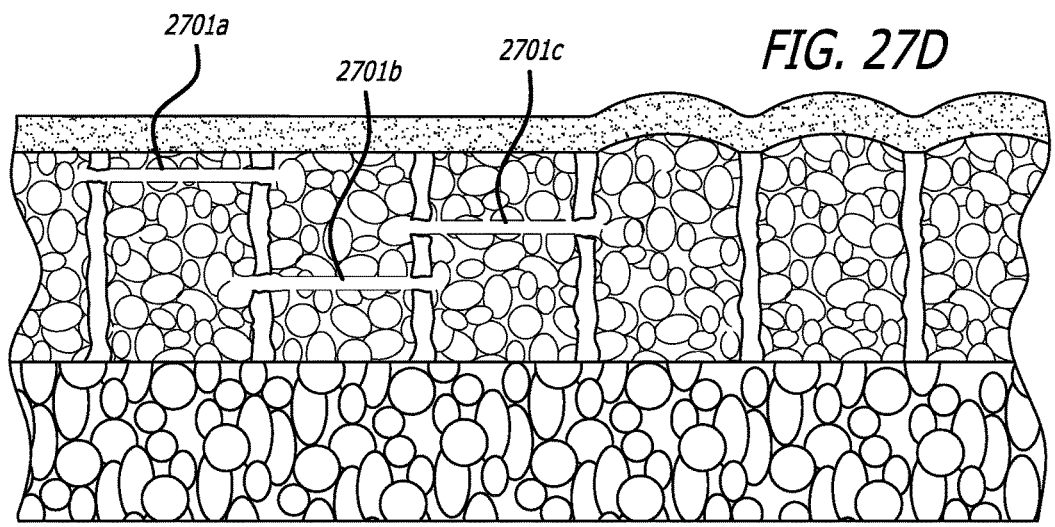

According to further embodiments, a relatively large treatment area is divided into a plurality of smaller treatment sites. FIGS. 27B and 27C show two or more treatment sites 2701a, 2701b, 2701c surrounded by untreated tissue 2702. In some embodiments, the spacing in the X-Y plane (parallel to the dermis) between adjacent treatment sites is reduced or eliminated. In some embodiments, the treatment sites could even overlap. Zero spacing (or overlapping) between adjacent sites is possible if adjacent treatment sites are at different treatment depths (measured perpendicularly from the dermis) and the bridge of untreated tissue can be greatly diminished without impacting the tissue healing time. In the embodiment depicted by FIG. 27C, treatment sites 2701a and 2701c are at a different treatment depth than 2701b. According to a further embodiment, treatment sites may not be contiguous, meaning that there are no multiple connected lesions. For instance, a further treatment area may include unconnected treatment sites 2703.

According to yet another aspect of the invention, adjacent treatment sites 2701 touch or even overlap but are at different treatment depths (measured in a direction perpendicular from the dermis). Thus, from a top view (FIG. 27C) the plurality of treatment zones 2701a, 2701b, 2701c appear to be continuous, but from a side view, depicted by FIG. 27D, it is clear that the "checkerboard" lesions 2701a, 2701b, 2701c are at different treatment depths. In other words, adjacent sites are at different treatment depths.

The interspersing of treatment sites at different treatment depths is believed to accommodate rapid healing. More specifically, the interspersing of treatment sites at different treatment depths allows for closer spacing between treatment sites while accommodating for a more rapid healing response time of the injured tissue. As the treatment area(s) heal, the tissue in the treated subcutaneous area regrows with minimal adipose tissue and minimal thickness such as to alleviate and substantially reduce the appearance of cellulite.

According to yet another aspect of the invention, the benefits realized by the multiple depth treatment enabled by the embodiments may be based on the severity of the specific lesion(s) or the specific area on the body being treated. For instance, it may be desirable to treat a deeper lesion at a deeper depth. Dimples or lesions on the thighs, for example, may be treated at a different depth than lesions on the buttocks. According to yet another aspect of the invention, the size of the dissection may also be adjusted by incomplete or partial movement of the cutting means within the guidance track. For example, with reference to FIGS. 6A and 6B, a smaller area may be treated than the total area accessible by guidance track 302 by not completing movement of the cutting module throughout all the arcs 602 or by not moving laterally as far along the arcs.

Methods according to the invention may be used to perform subcutaneous surgery in a minimally invasive manner. Steps comprised in exemplary methods of the invention to create a subcutaneous lesion are schematically outlined in the flowchart of FIG. 28B. Briefly, a section of skin and underlying tissue to be treated is anesthetized. Alternatively, general anesthesia may be employed. Next, a handpiece with a recessed area according to the invention is positioned over the section of skin. The air pressure inside the recessed area of the handpiece is reduced to lift the skin and the underlying tissue into the recessed area. The depth of the handpiece may be set at a level that allows the tissue plane to be dissected to align with a tool conduit in the handpiece. A lesion creation tool is inserted, and a lesion created, typically by moving the lesion creation tool along a guidance track. After completion of the lesion, the lesion creation tool is removed, the reduced air pressure returned to ambient, and the handpiece removed. Commonly created lesion types include dissections and thermal and chemical ablations. A number of different lesion creation tools may be used in methods according to the invention, and may be selected based on the type of lesion desired. For instance, to achieve a dissection a blade, needle or cutting wire may be employed. Also, cauterization, radio frequency, laser and water jet probes may be used in a cutting mode. Alternatively, if tissue ablation rather than dissection is desired, ultrasound probes, radiofrequency probes, laser probes, steam ablation probes, or other thermal probes may be used in a tissue ablation mode, thus thermally ablating the target tissue. Chemical ablation may be achieved by infusing sclerosants like ethanol, hypertonic salt or surfactant solutions. An RF or other type of energy tool can be used to coagulate and cut tissue at the same time with the same tool.

As described in more detail below, the reduced air pressure applied during the procedure may aid in creating an effective lesion, especially a dissection, possibly through the tension it puts on the tissue. As an optional step, as illustrated in FIG. 28C, the reduced air pressure may be maintained after completion of the lesion, for a period of time determined by the physician performing the procedure.

Previously, the use of increased rather than reduced pressure while creating a subcutaneous lesion has been described in the art, for instance by pressure infusion of an anesthetic solution during tumescent anesthesia. This increased pressure has been used to achieve more complete separation of the tissue layers surrounding a dissection plane.

It has now been observed that applying reduced pressure while creating the subcutaneous lesion, and optionally, maintaining the reduced pressure, for a period of time to be determined by the physician performing the procedure after completing the lesion, resulted in improved and more durable outcomes of the procedures. While the mechanism for this improved efficacy is not known with certainty, without being bound by theory, it is possible that the reduced pressure transmitted to the lesion enhances the tissue separation by forcing endogenous fluids, like blood and other extracellular fluids, to infiltrate into the lesion, thus creating an enlarged subcutaneous pocket. The presence of the endogenous fluids, and the formation of thrombus from the clotting of blood in this subcutaneous pocket, may have beneficial effects on the ensuing wound healing process.

Also, as will be discussed in detail below, a common feature of many subcutaneous tissues in humans is the presence of fibrous septae, connecting the skin to a subcutaneous tissue layer. Methods according to the invention include severing such fibrous septae. Applying reduced air pressure to the skin overlying the tissue and intended lesion may put tension on these septae, allowing for a more efficient severing process, as well as for an instantaneous and effective separation of the severed ends of the septae, preventing possible re-attachment and regrowth. Additionally, any fibrous septae that are not naturally oriented perpendicular to the skin and the plane of the dissection may be forced into a more perpendicular orientation by the force exerted on the skin from the reduced pressure, again allowing for a more efficient severing process.

Figure 28B:
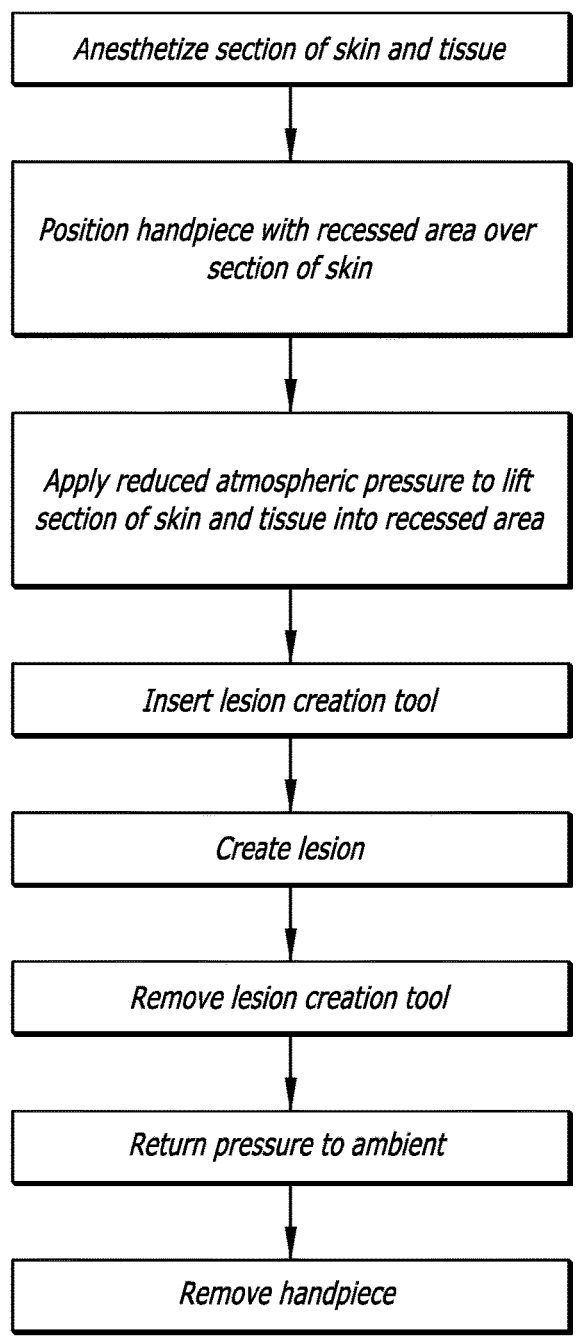
Figure 28C:
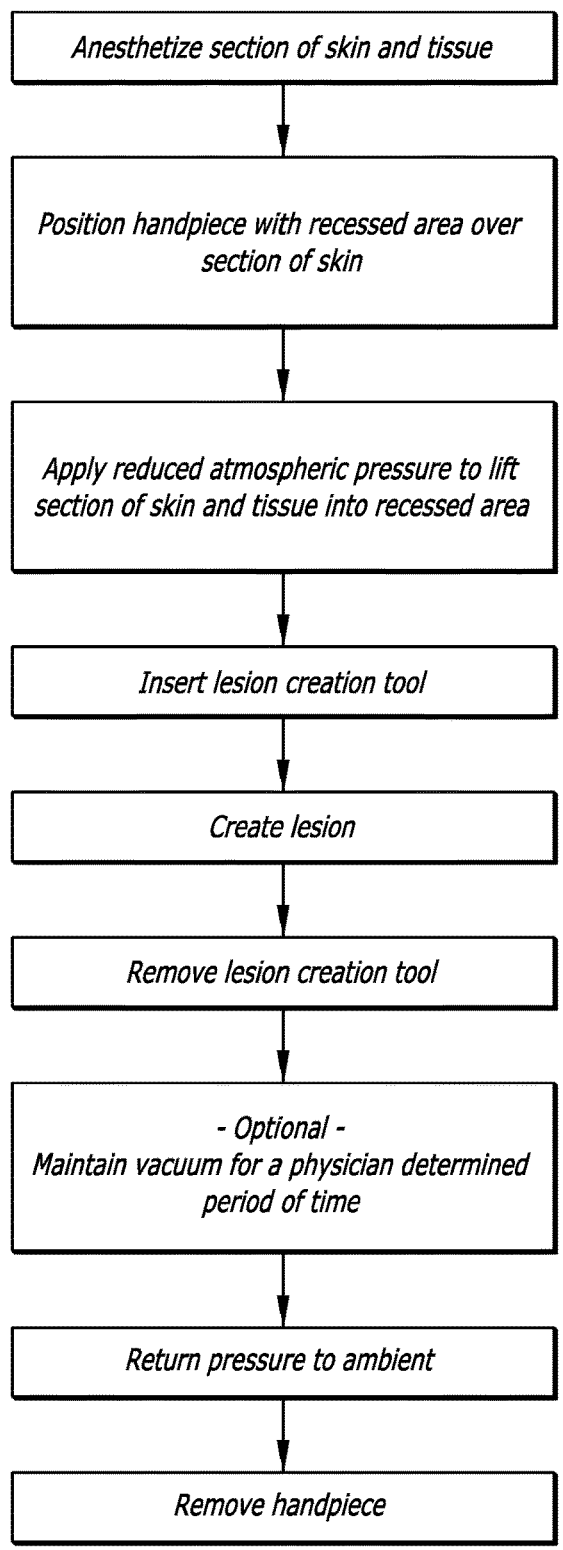

Optionally, the procedures of FIGS. 28B and 28C may be repeated on an adjacent or overlapping section of skin.

Figure 29:
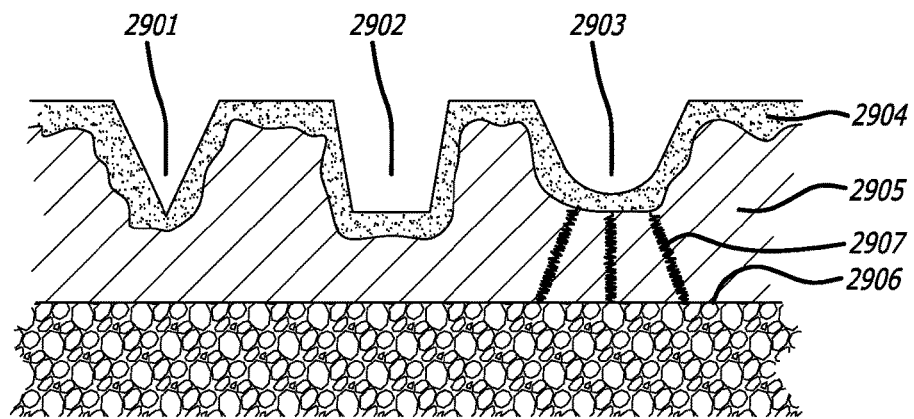
FIG. 29 depicts a cross sectional view of skin affected by acne scars.

Some methods disclosed herein may be especially useful in the performance of therapeutic or cosmetic procedures directed at improving the appearance of skin features. In particular, methods of the invention may be used to improve the appearance of deformities in sections of skin, for instance deformities such as scars, a wrinkles, and surface irregularities resulting from liposuction. The appearance of such deformities can be improved in various ways, including reducing differences in elevation between such deformities and the surrounding skin, making the tissue surface more uniform in texture, smoothness, color, and/or elevation within and/or around a deformity, redistributing fat or other tissue underlying a deformity to create a more smooth and uniform appearance, reducing tension or the appearance of tension within a deformity or between the deformity and surrounding skin, and others ways. Human skin is frequently attached to underlying layers of subcutaneous tissue by fibrous septae, limiting the mobility of the skin with respect to the underlying tissues. Such fibrous septae are often detrimental to the efficacy of corrective surgical procedures, such as cosmetic surgery, the prevention of hypertrophic scars after injury, and implantation procedures for cosmetic or therapeutic substances. An example of such fibrous septae is illustrated in FIG. 29 for the attachment of atrophic scars to underlying tissue. As is illustrated in FIGS. 30A-30D, and as will be discussed in more detail below, preferred methods of the present invention allow for an efficient and minimally invasive severing of such fibrous septae, enabling more effective improvement of the skin features, and, where desired, introduction of therapeutically or cosmetically beneficial substances.

It should be understood that, although the detailed description below, and as illustrated in FIG. 30A-30D is specific to the treatment of atrophic scars, in particular acne scars, the procedure is representative of other methods and treatments generally falling within the scope of the invention.

In some embodiments of the invention, methods to perform subcutaneous surgery are directed at treating atrophic scars, including acne scars. As illustrated in FIG. 29, atrophic scars are characterized by a sunken recess morphology of the epidermis 2904 and the dermis 2905. Several subtypes of acne scars have been described in the literature, and their etiology and patho-physiology are broadly representative of most types of atrophic scars. Other commonly occurring types of atrophic scars are those secondary to chicken pox, skin infections or accidental or surgical trauma.

A common classification divides atrophic acne scars in three groups:

Ice pick scars 2901, with steep walls and a pitted appearance;

Boxcar scars 2902, with steep walls and a more or less defined bottom; and

Rolling scars 2903, typically showing a more gradual depression.

Rolling scar tissue is further characterized by the fact that it is tethered to the underlying subcutaneous tissue 2906 by fibrous septae 2907.

A surgical treatment sometimes used for the treatment of atrophic scars is subcision, in which a tri-beveled needle is repeatedly inserted into the subcutaneous space to cut subcutaneous tissue, specifically the fibrous septae. In a typical procedure the needle may be inserted many times, moving in fan-shape patterns radiating from its access site. This may be followed by a fan-like sweeping action, to ensure full detachment of the tissue layers. This procedure makes the method time consuming and prone to inadvertent deeper injury due to the large number of lancing movements with the needle.

Additionally, in clinical practice, re-depression after an initially seemingly successful procedure is commonly observed. It is thought that initially blood and extracellular fluid fill a pocket around the dissected needle tracks that provides lift to the treated scar. When an inadequate pocket is created, resorption of the coagulated blood and fluids over time may cause the pocket to collapse, causing the late failure.

Achieving a complete dissection plane with reliable severance of all fibrous septae and the creation of an adequate tissue pocket to provide support to the overlying scars after complete healing are considered key factors in the achievement of durable results.

Furthermore, local application of reduced air pressure over individual subcised acne scars has been reported to reduce the incidence of re-depression. In some instances, periodically repeating the application of reduced air pressure over a period of up to two weeks has been reported to be beneficial.

In an exemplary embodiment of the method, illustrated in FIGS. 28B and 28C, and FIGS. 30A and 30B, creation of a dissection plane, severing of the and application of reduced air pressure to create an adequate tissue pocket are performed using a device according to the invention.

Figure 28D:
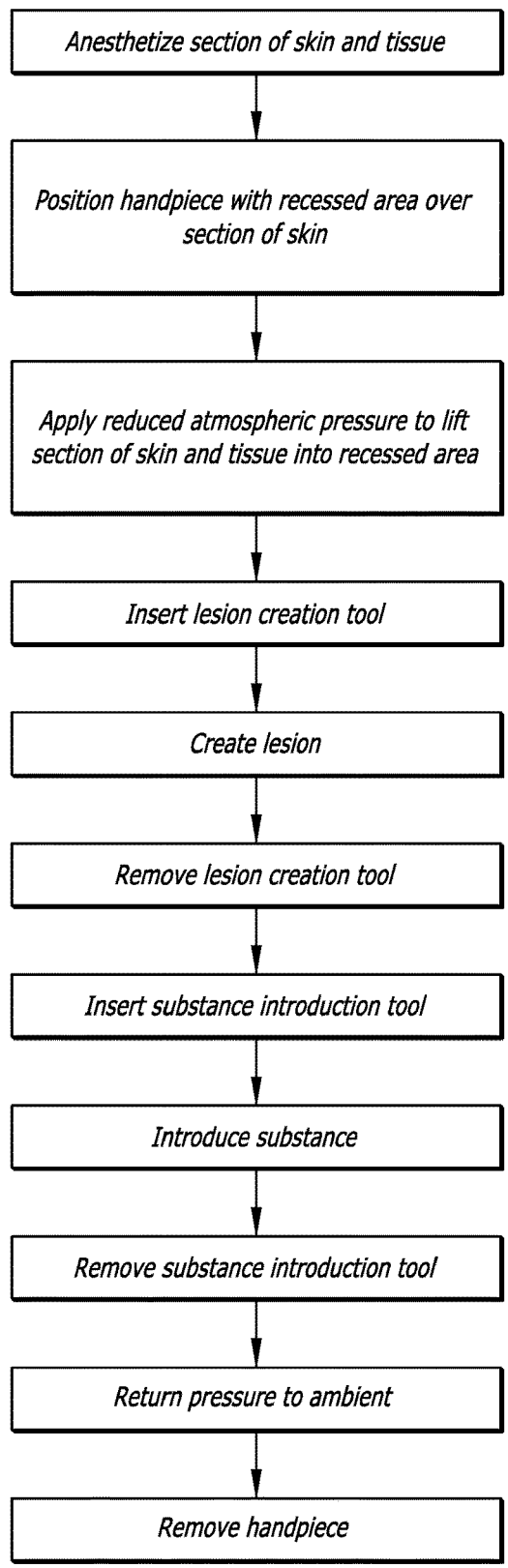

As outlined in the flow chart shown in FIGS. 28B-D, the skin area to be treated is first anesthetized.

Figure 30A:
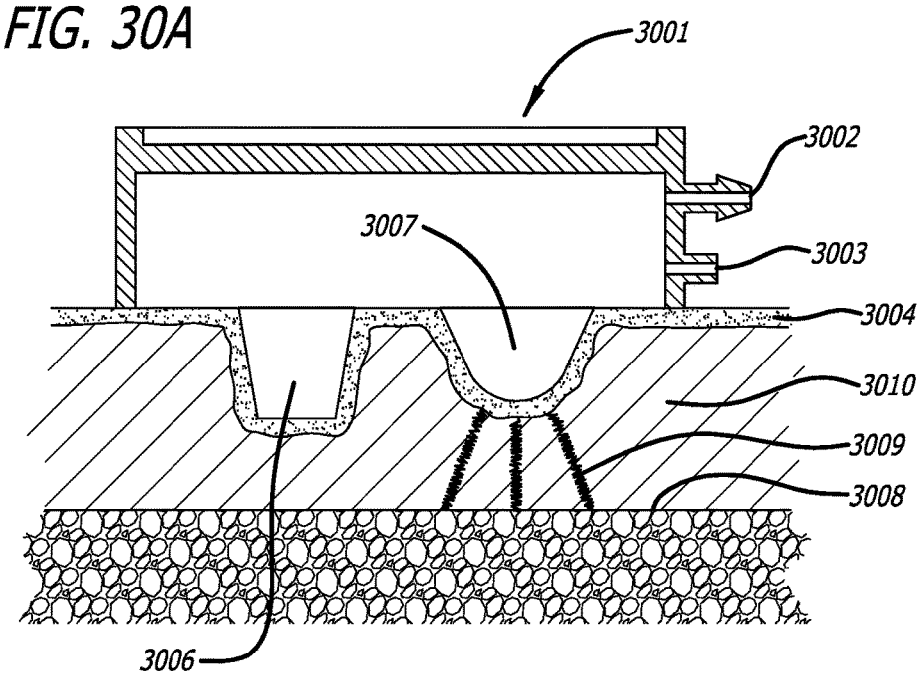

Next, as further illustrated in FIG. 30A, a handpiece 3001 with a recessed area, having a vacuum conduit 3002 and a tool conduit 3003 is placed on top of the epidermis 3004. The handpiece 3001 covers a boxcar scar 3006 and a rolling scar 3007. The tissue of the rolling scar 3007 is attached to the subcutaneous tissue layer 3008 by the fibrous septae 3009 through the dermis 3010.

As illustrated in FIG. 30B, a vacuum is then applied through conduit 3002, pulling the skin area into the recessed area of the handpiece 3001. A dissection tool 3011 is then inserted through the tool conduit 3003 into the subcutaneous tissue underlying the acne scars and a dissection plane 3012 is created, severing the fibrous septae 3009. The dissection tool 3011 is then removed.

In a subsequent step, illustrated in FIG. 30C, a tissue pocket 3013 surrounding the dissection plane 3012 is filled with fluid. The fluid may be actively injected, for instance through tool conduit 3003. The fluid may perform a number of functions, including mechanical support and pharmaceutical activity, as will be described in detail below. Alternatively, endogenous fluids, like blood and extracellular fluids may be allowed to infiltrate the pocket 3013.

Finally, the vacuum is released, the handpiece 3001 removed, and, as illustrated in FIG. 30D, the skin area allowed to assume its post-procedural position, in which the support provided by the fluids in the subcutaneous pocket 3013 may lift the remnants of acne scars 3006 and 3007 closer to the surrounding skin level.

Figure 31:
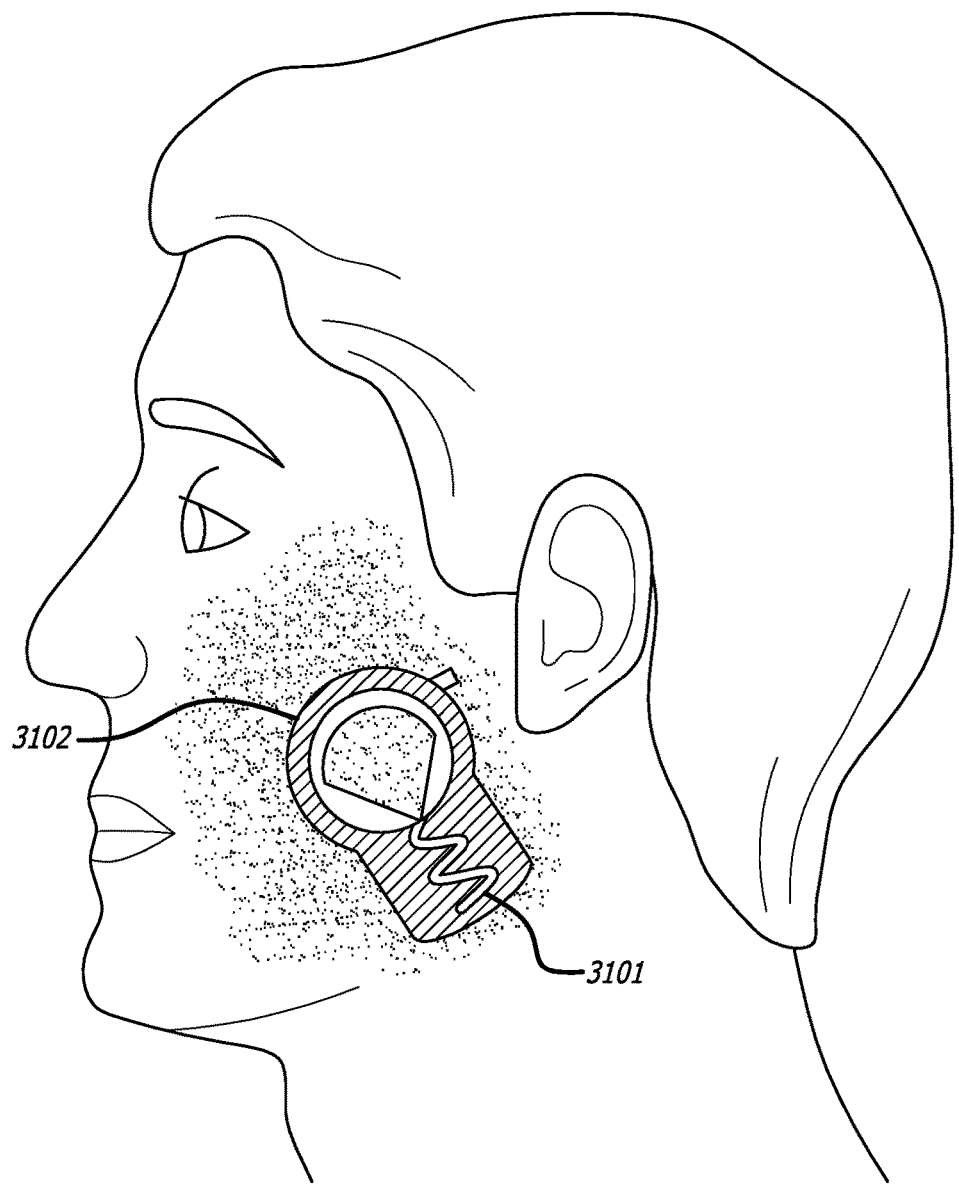
FIG. 31 depicts a position of a handpiece and guidance track on a skin area in the treatment of acne.

As illustrated in FIG. 31 a guidance track 3101 matching the skin area to be treated may be used in addition to the handpiece 3102 at the discretion of the physician.

It should be understood that the method outlined in the flow chart of FIGS. 28B and 28C and illustrated in FIGS. 30A-30E is an example of many variations on the procedure falling under the scope of the present invention that can be performed at the discretion of the physician. For instance, the physician may decide to release the vacuum before injecting a fluid into the dissection pocket. Alternatively, the physician may decide that pulling vacuum in the skin and creating the dissection plane sufficiently releases the overlying skin, and omit the step of actively filling the tissue pocket with fluid.

Also, the procedure may be performed in a single pass with a relatively large handpiece, or may be performed in a repeated sequence, in which a smaller handpiece is used multiple times on adjacent or overlapping skin areas. For instance, a physician may decide to use the method exclusively for the severing of septae connecting individual rolling scars to the underlying tissue layer.

Figure 32A:
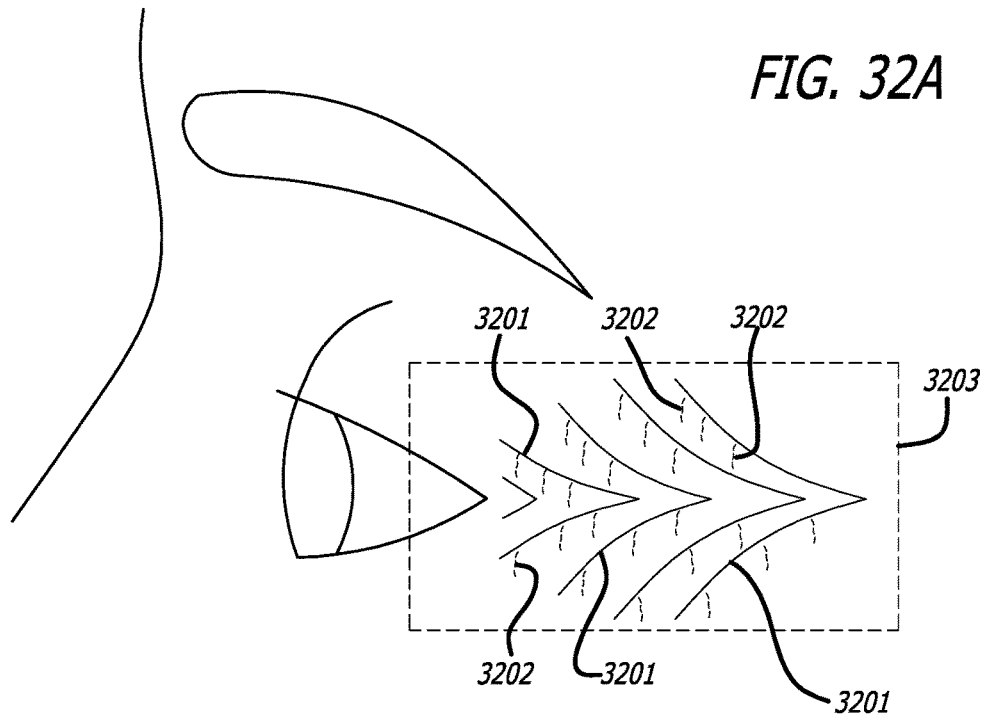
FIG. 32A depicts an area of peri-orbital skin affected by crow's feet wrinkles.

In some embodiments of the invention, methods to perform subcutaneous corrective surgery are directed at treating wrinkles. As illustrated in FIG. 32A, skin tissue at the site of wrinkles, and especially facial wrinkles 3201 near the eye, may have extensive fibrous septae 3202 connecting them to the underlying Superficial Muscular Aponeurotic System (SMAS) 3203. Many cosmetic surgery procedures employ fillers, like collagen or hyaluronic acid to bulk up the space below the skin. This approach by itself often results in unsatisfactory results, because of the fixed attachment of the skin to the underlying SMAS 3203. In these cases, controlled severing of the fibrous septae 3202 may allow for a more effective use of the fillers to reduce the appearance of expression lines. Severing fibrous septae 3202 can be performed by the method and apparatus disclosed in FIGS. 28B-31.

Figure 32B:
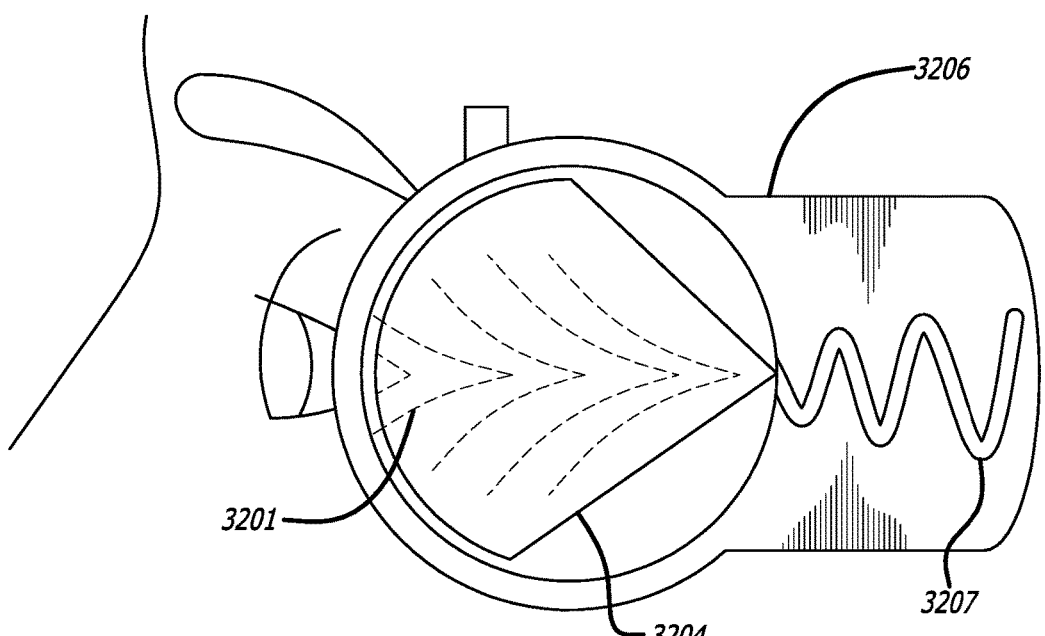
FIG. 32B depicts a position of a handpiece and guidance track on a skin area in the treatment of crow's feet wrinkles.

Some embodiments of methods of the invention are particularly useful to improve such corrective procedures. The steps in these methods are analogous to the steps outlined in the flow charts of FIGS. 28B and 28C and in the procedure of FIGS. 30A-30B for the treatment of atrophic scars. As illustrated in FIG. 32B for treatment of crow's feet 3201 (skin wrinkles near the eye), a handpiece 3206 for applying vacuum advantageously comprises a recessed area 3204 matching the fan-shaped pattern of the crow's feet 3201, and can be combined with a matching guidance track 3207.

Figure 33:
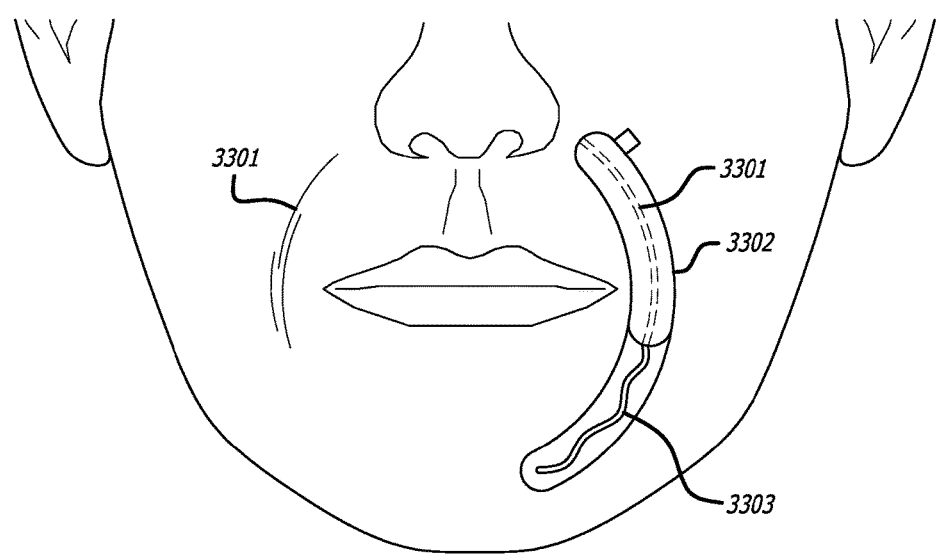
FIG. 33 depicts a position of a handpiece and guidance track on a skin area in the treatment of a laughing line wrinkle.

As illustrated in FIG. 33, an alternative embodiment of the invention may be used to treat wrinkles knows as laughing lines 3301 (skin wrinkles near the mouth). In this embodiment, a more elongated shape for the handpiece 3302 and the guidance track 3303 are preferred, allowing for a motion of a cutting tool matching the contours of the laughing line 3301.

As with the methods described above for the treatment of atrophic scars, many variations of the procedure, available at the discretion of the physician, fall under the scope of the invention. For instance, the physician may decide to insert an implant according to the method described below, rather than to inject a fluid.

In some embodiments of the invention, methods to perform subcutaneous surgery are directed at treating sections of skin overlying tissue that has been previously treated with liposuction. Liposuction procedures frequently remove considerable amounts of fat, and a successful outcome often relies on a redistribution of the remaining fat and on adaptation of other subcutaneous tissues into a smooth body contour, often by aided by application of pressure and post-surgical massage. Insufficient mobility of the fat and subcutaneous tissue may result in an uneven and cosmetically unappealing appearance of the skin. In some of these cases, secondary procedures, sometimes referred to an autologous lipografting, are performed, in which quantities of fat are harvested from sites with excess fat and reintroduced to sites that are in need of augmentation. Similarly to primary liposuction, insufficient mobility of skin and subcutaneous tissue interferes with such procedures.

Major fat deposits frequently comprise substantial internal anatomical structures, often with a Superficial Adipose Tissue (SAT) layer and Deep Adipose Tissue (DAT) layer, separated by a more or less developed fibrous membrane. Extensive fibrous septae often exist in the SAT, between the skin and the fibrous membrane, mostly in a perpendicular orientation to the skin. The presence of these septae, in combination with the deposition of excess fat, is one of the underlying causes of cellulite in women. Fibrous septae are found in the DAT as well, connecting the fibrous membrane to deeper fasciae, albeit less abundant than in the SAT, and often in a more oblique orientation. The presence of this network of fibrous septae tethering various cutaneous and subcutaneous layers may impair the mobility of local tissues and prevent the creation of a smooth body contour. Additionally, trauma caused by the probes used during the procedure occasionally leads to a scar-like healing reaction involving the development of post-surgical subcutaneous adhesions, for instance between the dermis and the underlying fibrous membrane. These adhesions may further impair skin and tissue mobility, and exacerbate the undesirable appearance of the skin.

Methods according to the invention may be particularly suitable for carefully targeted severing of fibrous septae and adhesions at pre-defined depths with respect to the skin. For instance, severing the fibrous septae in the SAT can be achieved by lifting subcutaneous tissue into a recessed area of a handpiece according to the invention, as described in U.S. Pat. No. 8,518,069, which is incorporated hereby in its entirety.

Figure 34A:
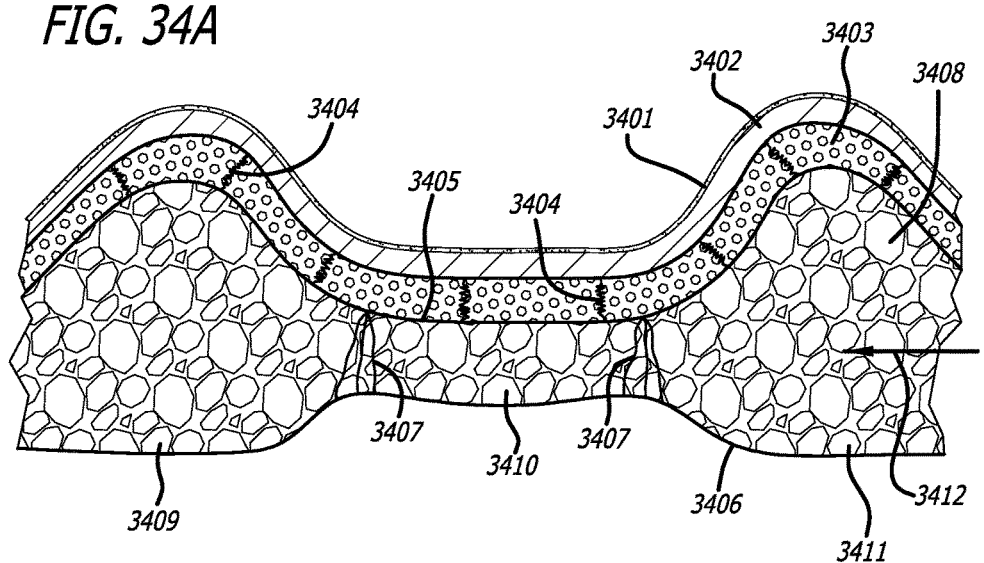
FIGS. 34A-34B depict a cross-sectional view of skin with irregularities due to previous liposuction and a treatment step.

An exemplary method to sever deeper located fibrous septae is illustrated in FIG. 34A. Epidermis 3401 and dermis 3402 overlie a SAT layer 3403 of fat. Fibrous septae 3404 connect the dermis 3402 to the fibrous membrane 3405. SAT layer 3403 has a satisfactorily even distribution of fat, and disturbing the septae 3404 may actually have a detrimental effect, for instance by causing a loss of skin tone in the epidermis 3401 and dermis 3402. Fibrous membrane 3405 is connected to a deeper fascia 3406 by fibrous septae 3407.

The fibrous septae 3407 divide the DAT layer 3408 into compartments 3409, 3410 and 3411. Compartment 3410 has been successfully depleted of fat cells by liposuction, while compartments 3409 and 3411 still contain major fat deposits. The fibrous septae 3407 prevent a more even distribution of fat cells between the compartments 3409, 3410 and 3411.

Current treatments often used subcision techniques, in which sharp canulae with an inverted V-tip, like the V-tip Toledo Canula, are inserted at a shallow angle through the various tissue layers to dissect the septae 3407. The poorly guided direction and repeated lancing action of these canulae has the potential for unwanted collateral tissue damage.

Figure 34B:
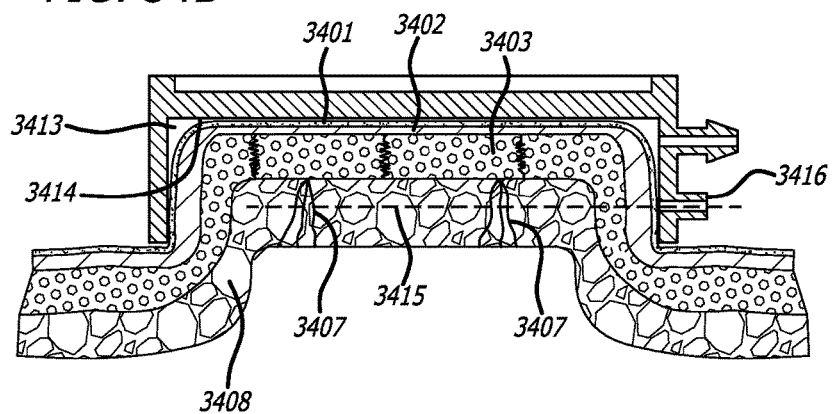

Methods of the current invention, as outlined in FIGS. 28B and 28C, and as described in more detail in FIGS. 30A-30B, allow for a precise depth control of lifting the skin and subcutaneous tissue into a recessed area of a handpiece according to the invention. Subcutaneous fibrous membranes and fibrous septae are detectable by ultrasound, and, if necessary, by CT imaging. These imaging techniques allow for a precise lifting of the tissue, and positioning of a plane of dissection at the level of arrow 3412, to be created through the septae, to align with a tool conduit in the handpiece. As shown in FIG. 34B, the section of skin and the underlying tissue can be lifted into a recessed area 3413 of a handpiece according to the invention, such that epidermis 3401, dermis 3402 and SAT fat layer 3403 are precisely brought into apposition with the top 3414 of the recessed area 3413. The depth of the recessed area 3413 has been calibrated, based on previously mentioned imaging techniques, to align a plane of dissection 3415, comprising the septae 3407, to align with a dissection tool conduit 3416 in the handpiece. In this manner, methods according to the invention allow for precise targeting of culprit fibrous septae, with minimal collateral damage to surrounding and possibly beneficial anatomical structures.

In some embodiments of the invention, methods to perform subcutaneous corrective surgery are directed at promoting wound healing and reducing the occurrence and severity of contractile scars. Contractile scar formation is a serious and sometimes debilitating side effect of wound healing. Tension within the plane of the skin at the site of the wound is generally considered a significant factor in the development of contractile scarring.

Figure 35A:
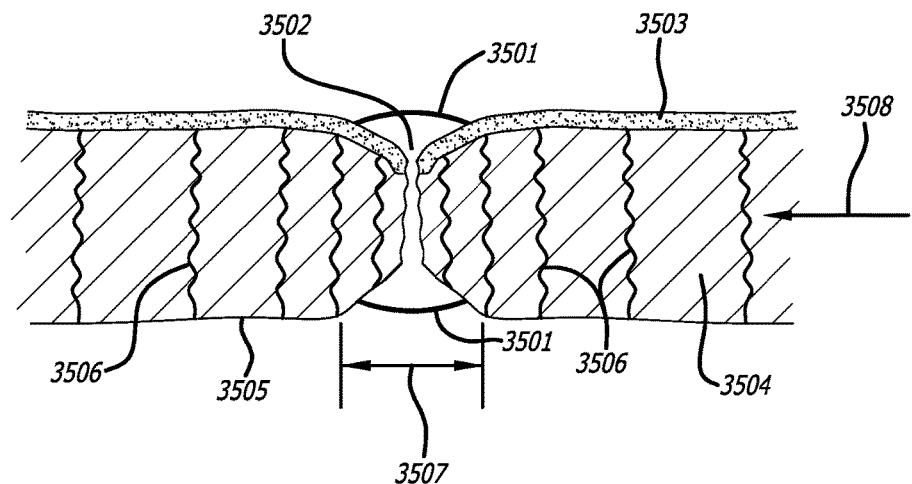
FIGS. 35A-35B depict cross-sectional views of skin in a method of the invention directed at dissipating local tension at the site of a sutured wound.
Figure 35B:
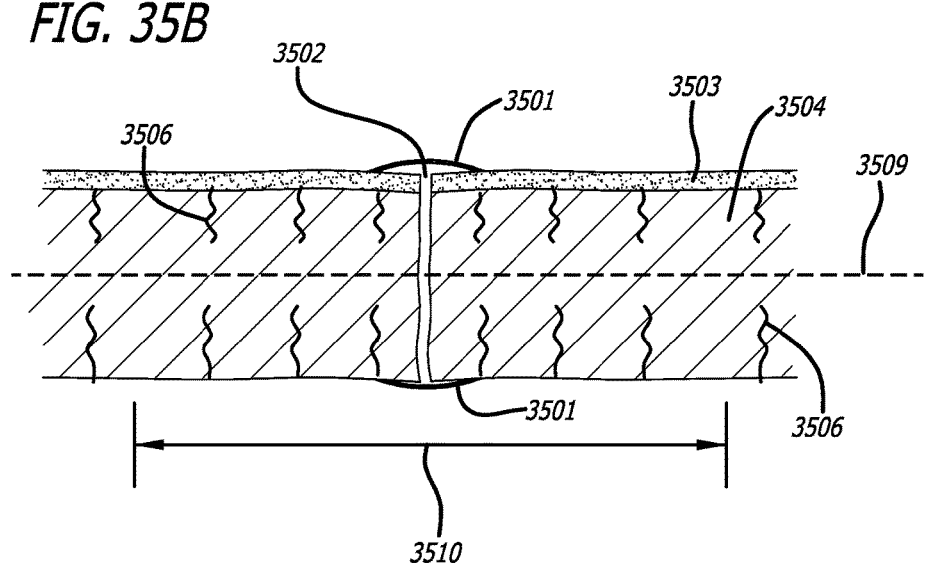

As illustrated in FIG. 35A, the placement of a suture 3501 over wound 3502 may exert forces on the epidermis 3503 and the dermis 3504. The non-elastic fibrous septae 3506 anchor the dermis 3504 and epidermis 3503 to the non-elastic subcutaneous tissue layer 3505, causing a highly localized tension, indicated by line 3507, at the site of the closed wound 3502, essentially creating a local stress riser. The skin itself tends to be more elastic than the fibrous septae 3506 connecting it to the underlying tissue 3505. Severing the inelastic fibrous septae 3506 at the level 3508 and creating a dissection plane 3509 shown in FIG. 35B relieves the local stress by spreading the tension over a significantly wider area, as indicated by line 3510.

Embodiments disclosed herein may be used advantageously to perform the post-wound closure procedure by following the procedure outlined in the flow chart of FIGS. 28B and 28C, and illustrated in FIGS. 30A-30B. In this case the handpiece is placed over a skin area that surrounds the closed wound 3502 and the skin area with the closed wound is vacuum-pulled into the recessed area of the handpiece. Creation of the dissection is then performed as described above in connection with FIG. 30B. Injection of fluids as described above to create additional subcutaneous space may be performed at the discretion of the physician.

Figure 36A:
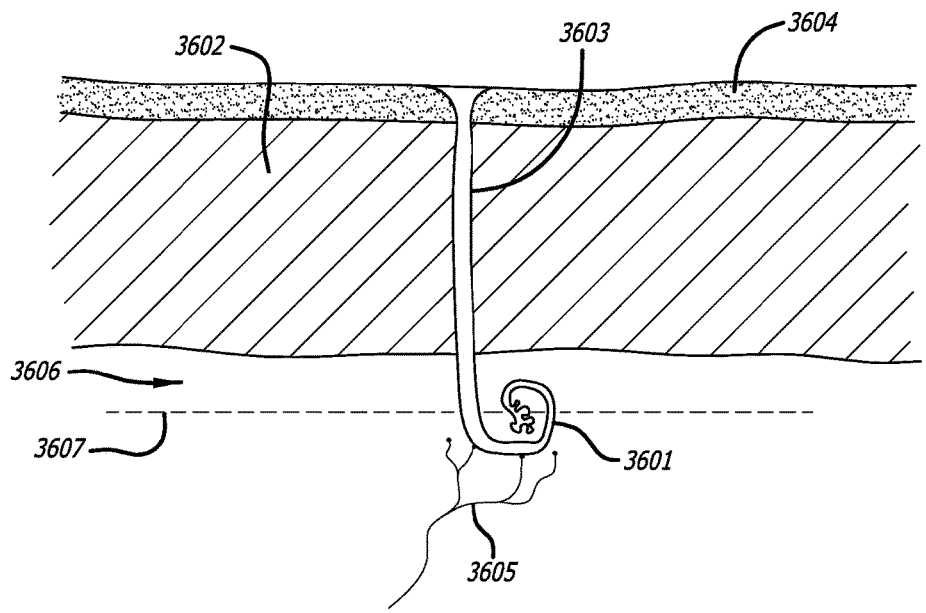
FIGS. 36A-36B depict a cross-sectional view of skin with an eccrine sweat gland and an innervating nerve bundle and a cross sectional view of an RF nerve ablation

In some embodiments of the invention, methods to perform subcutaneous corrective surgery are directed at inhibiting hyperhidrosis. Hyperhidrosis is a condition characterized by an excessive production of sweat by eccrine sweat glands, specifically in the armpits, hands and feet. As illustrated in FIG. 36A, sweat glands 3601 lie in a relatively narrow band of depth underneath the dermis 3602 and secrete sweat through the sweat duct 3603 to the epidermis 3604. Sweat glands can be detected by ultrasound. Sweat glands 3601 are innervated by branches 3605 of the sympathetic nerve system.

Two different approaches to treat hyperhidrosis are available for methods according to the invention. One approach involves obliteration of the sweat glands 3601 by the creation of dissection plane 3607 through the glands 3601 themselves, effectively destroying them. In this case, a handpiece is placed over an area of skin containing sweat glands to be obliterated, and the depth of the recessed area is set such that, after application of reduced air pressure, the sweat glands 3601 are positioned at the level of the tool conduit, facilitating the creation of a dissection plane. The dissection plane 3607 is created at the level of arrow 3606, effectively cutting through the sweat glands 3601. The dissection can be performed with a mechanical dissection tool, like a needle or a blade, or with a heat-enabled cutting tool like an RF probe.

The use of an RF probe may be particularly effective in that the energy output can be chosen to create an area of tissue destruction beyond the immediate dissection plane, allowing obliteration of sweat glands that, because anatomical variability, fall outside the actual dissection plane.

Figure 36B:
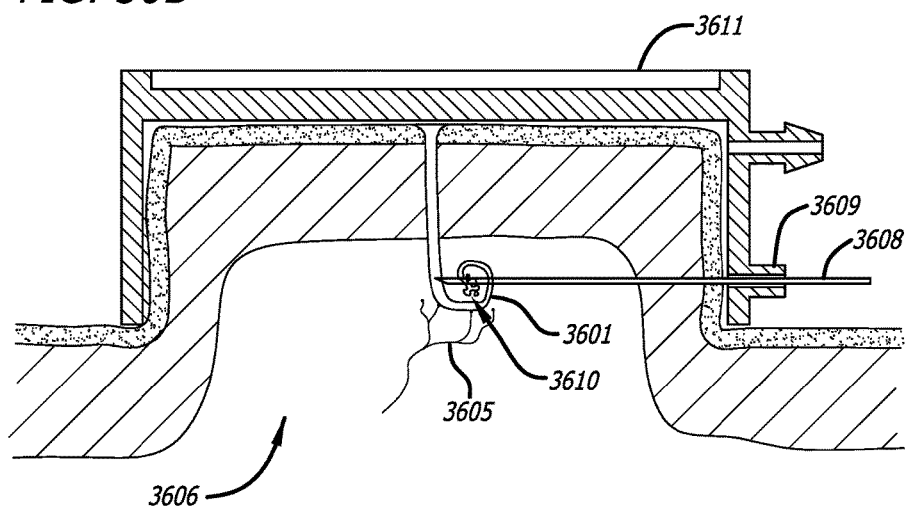

The second approach is directed at denervation of the sweat glands 3601 by severing the sympathetic nerve branches 3605 activating the glands. The nerve branches 3605 approach the glands 3601 from below, as illustrated in FIG. 36B. In this approach the, tissue is pulled slightly deeper into the handpiece than when the sweat glands themselves are targeted, exposing the nerve branches 3605 to a cutting tool. The exact depth of the dissection plane may be selected by the physician based on other considerations of the local anatomy, like vasculature to be avoided, etc. In this approach, subjecting the tissue to adequate tension by the reduced air pressure applied to the recessed area, or injection of fluid into the dissection plane may assist in achieving adequate separation of the nerve ends to prevent re-growth or re-attachment.

FIG. 36B illustrates an exemplary embodiment of a method according to the invention, in which a radiofrequency probe 3608 is used to ablate an anatomical area encompassing a sweat gland 3601 and an efferent sympathetic nerve branch 3605. According to methods outlined in FIGS. 28B and 28C, and described in more detail in FIGS. 30A-30D, a section of skin comprising an epidermis 3604 and a dermis 3602 and a subcutaneous tissue 3606 have been moved into a recessed area of a handpiece 3611. The subcutaneous tissue 3606 comprises sweat gland 3601 and efferent sympathetic nerve 3605. A RF ablation probe 3608 has been inserted through conduit 3609 into the subcutaneous tissue 3606 comprising the sweat gland 3601 and the nerve 3605. Activation of the RF probe 3608 can be used to create a heat zone 3610 in the subcutaneous tissue 3606 comprising the sweat gland 3601 and the nerve 3605, thereby effectively thermally ablating the sweat gland 3601 and the nerve 3605.

Figure 37A:
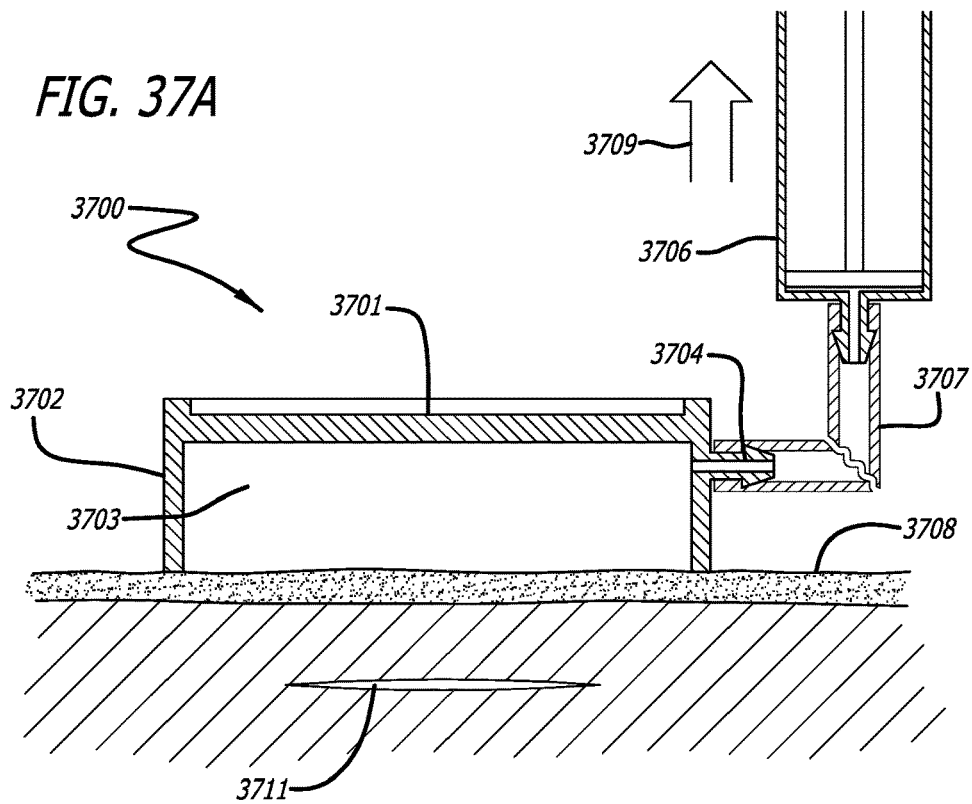
FIGS. 37A-37B depict a method to apply a vacuum assisted suction force on a treated area of skin in a post-procedural treatment.
Figure 37B:
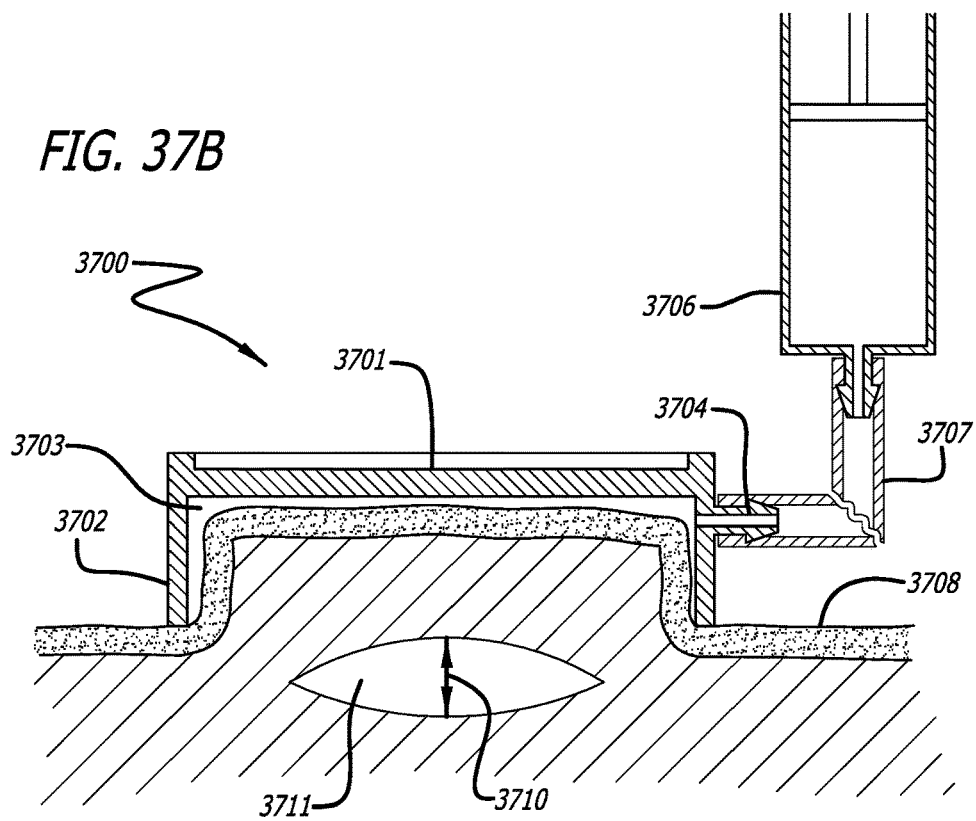

In alternative embodiments, a handpiece may be a stand-alone tool, capable of applying a reduced air pressure to a skin surface located over a previously created subcutaneous lesion, for instance a dissection plane, during the post-procedural healing period. Periodically applying reduced air pressure for brief periods of time to an area of skin after creating a subcutaneous dissection plane and severing subcutaneous septae has been shown to have potential benefits on the healing response. In particular, a reduction in tissue re-depression after treatment of atrophic acne scars has been observed. However, the methods of use are not limited to this indication, and may be combined with any of the treatments described in this disclosure. The device and methods are illustrated in an exemplary embodiment in FIGS. 37A and 37B. A handpiece 3700 in FIG. 37A has a top 3701, a perimeter elevation 3702 defining a recessed area 3703. The perimeter elevation 3702 is fitted with a vacuum conduit 3704. The vacuum conduit is configured to be connected to a vacuum device, for instance a syringe 3706 fitted with length of tubing 3707. After placing the handpiece 3700 on the surface of the skin 3708, reduced air pressure is applied by moving the plunger of the syringe 3706 in the proximal direction 3709, thereby creating a vacuum in the recessed area 3703 and drawing the surface of the skin 3708 into the recessed area 3703, as shown in FIG. 37B. Alternatively reduced air pressure may be applied using a vacuum pump or other suitable source of suction. The reduced air pressure thus applied puts traction 3710 on the pocket 3711 around the subcutaneous plane, potentially improving the local healing response.

In another embodiment the device may be configured as a kit for post-procedural treatment of a previously created lesion or dissection plane in a home setting or by a non-physician medical professional, wherein the kit comprises a handpiece, and vacuum device and a means to couple the handpiece to the vacuum device. Methods of use of the embodiments according to the invention may include in-office procedures performed by a healthcare professional, or use as a home therapy, to be applied by a patient, family member or other non-professional individual. The reduced air pressure may be controlled by any of the means described earlier in this disclosure, including simple manipulation of a syringe.

In some embodiments, methods to perform minimally invasive subcutaneous surgery are directed at creating a lesion configured as a subcutaneous tissue pocket and the introduction of a substance by a physician. The lesion may be specifically configured as a tissue pocket for a particular substance, such as a solid implant, in which case the pocket may be shaped according to the shape of the implant. For instance, for an implant requiring subcutaneous tunneling, an elongated tissue pocket may be created, for a subcutaneous venous access device a circular pocket may be appropriate, and for a shape-correction cosmetic implant a custom-shaped pocket for the implant may be required. In other cases the lesion may be enlarged by the introduction of the implant itself, and the initial configuration of the pocket may such that it accommodates a leading edge of the implant to facilitate its introduction. In some cases a liquid substance may be introduced, and the lesion needs to be configured as a tissue pocket large enough to accommodate the entire injected volume without the risk of the fluid being expelled through the access site by the elasticity of the surrounding tissue.

The substance may comprise a medical device, a drug, a biologic, or a combination device, or any combination of these four categories. The definitions of these categories for the purpose of this disclosure are listed below. They are generally in line with the definitions as used by the United States Food and Drug Administration (FDA) as of September 2013.

Briefly:
- A medical device is a medical product that derives its benefit from a mechanical action.
- A drug is a medical product that derives its benefit from a chemical or biochemical action.
- A biologic is a medical product that is derived from a natural source.
- A combination product is a medical product that combines two or more regulated medical components.

Additionally, the substance may comprise non-regulated components, such as pharmacy-compounded compositions. Also, the substance may comprise autologous tissue harvested from an alternative site on the anatomy of a patient. Adipose tissue and segments of bone are examples of materials frequently used as space-filling implants in corrective cosmetic surgery.

The substances may comprise fluids, semi-solids like injectable gels, and solid implants. Fluids may be actively injected, for instance by using a syringe, or may be drawn into the pocket from an external reservoir by reduced pressure applied to a handpiece. Fluids may perform a number of functions, including enlarging the subcutaneous tissue pocket, providing structural support, and affecting the biological response to the procedure by means of a drug. Simple enlargement of the tissue pocket may be achieved by the injection of, for instance, a physiological saline solution. Support for the pocket and surrounding tissue may be achieved by injection of a fluid containing a liquid polymer formulation to enhance viscosity, or by injection of a suspension of microparticles.

Suitable polymers for injection include commonly used materials for cosmetic and reconstructive surgery, such as collagen and hyaluronic acid. Suitable microparticulate systems include formulations based on biodegradable polymers, like poly-lactic acid and poly-glycolic acid and their copolymers, poly-caprolactone, poly-urethanes, poly-phosphazenes, poly-anhydrides, poly-orthoesters, polypeptides, poly-saccharides and polycarbonates. Permanently implanted materials may include silicones, poly-olefins, poly-urethanes, poly-acrylates and poly-methacrylates, poly alkylene oxides, polyols, such as polyvinyl alcohol, polyvinylpyrrolidones, and poly-fluorinated polymers, such as poly-tetrafluoroethylene. The materials may comprise linear polymers, crosslinked polymers, homo-polymers and co-polymers.

Drugs may include compounds like local anesthetics, anti-inflammatories, anti-biotics, hemostatics, and healing response modifiers like collagen promoters. Multiple functions can be combined in an injected fluid, for instance the polymeric components may be used as controlled release carriers for the drugs.

Solid subcutaneous implants may be used for a variety of purposes. They include shape-enhancing implants used in cosmetic or reconstructive surgery and therapeutically used implants, like electronic devices and drug delivery systems.

Cosmetic or reconstructive solid subcutaneous implants are most commonly used in the face, neck, breast and buttock areas. They typically perform a supporting, enlarging or defect-filling function, and can have a wide variety of shapes and consistencies, depending on the specific cosmetic corrections intended. They may be used in the form of solid implants, in which case a relatively large incision may be required for placement, or they may be of an inflatable design, in which case they may be introduced through a relatively small incision.

Therapeutically used solid subcutaneous implants include vascular access devices like venous infusion ports and subcutaneous hemodialysis catheters, drug delivery devices, like birth control implants or devices releasing chemotherapeutics or hormonal treatments, and a number of electronic devices, like subcutaneous defibrillators and pacemakers, battery packs, identity chips, etc. They are preferably implanted in anatomical areas with relatively little mobility, frequently on the upper chest. Smaller drug delivery implants are often implanted on the medial aspect of the upper arm.

Steps comprised in exemplary methods of the invention for creation of a dissection plane to form a tissue pocket and placement of a substance in the tissue pocket are schematically outlined in the flowchart of FIG. 28D, and described in more detail in FIGS. 38A-38E. Briefly, as outlined in FIG. 28I), a section of skin and underlying tissue to be treated is anesthetized. Alternatively, general anesthesia may be employed. Next, a handpiece having a recessed area according to the invention is placed over the section of skin to be treated. Reduced air pressure is applied to the recessed area of the handpiece, lifting the skin and the underlying tissue into the recessed area. The depth of the handpiece may be set at a level that allows the tissue plane to be dissected to align with a tool conduit. A lesion creation tool is inserted, and a lesion in the form of a tissue pocket created, typically by moving the lesion creation tool along a guidance track. After completion of the lesion the lesion creation tool is removed, and a substance introduction tool inserted. A substance is introduced into the tissue pocket, the substance introduction tool removed, the reduced pressure released, and the handpiece removed.

In some embodiments, the substance to be introduced may comprise a fluid, and the substance introduction tool may be a syringe. In some embodiments of the invention, the substance to be introduced may comprise a solid, and the substance introduction tool may be a probe having a cavity holding the implant and a push rod to advance the implant out of the cavity and into the subcutaneous tissue pocket. In some embodiments the substance introduction tool may serve as a trocar-like conduit to introduce a solid implant. In some embodiments the substance introduction tool may be configured to enlarge the subcutaneous lesion into a larger tissue pocket. In some embodiments of the invention a physician may introduce a solid implant manually, without the aid of an introduction tool. In some embodiments of the invention, the order of steps may be changed. For instance, the reduced air pressure may be released before inserting the substance introduction tool.

Figure 38A:
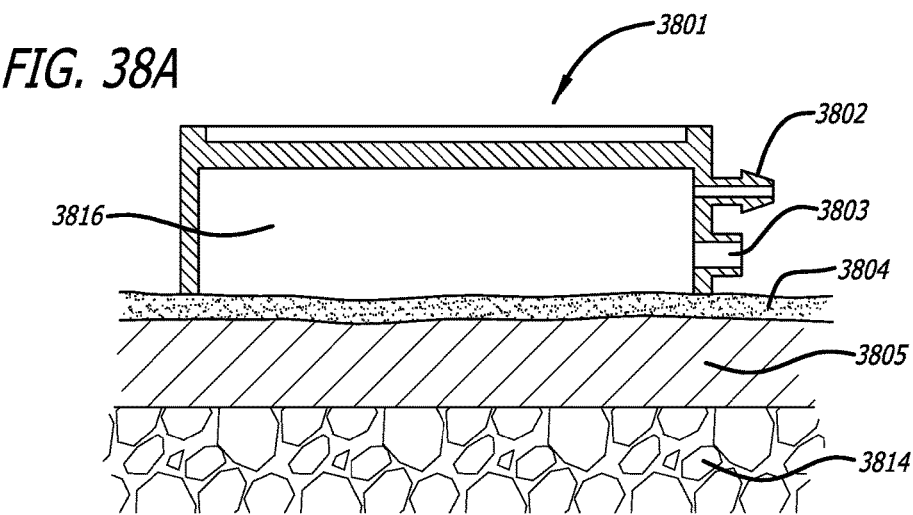
Figure 38B:
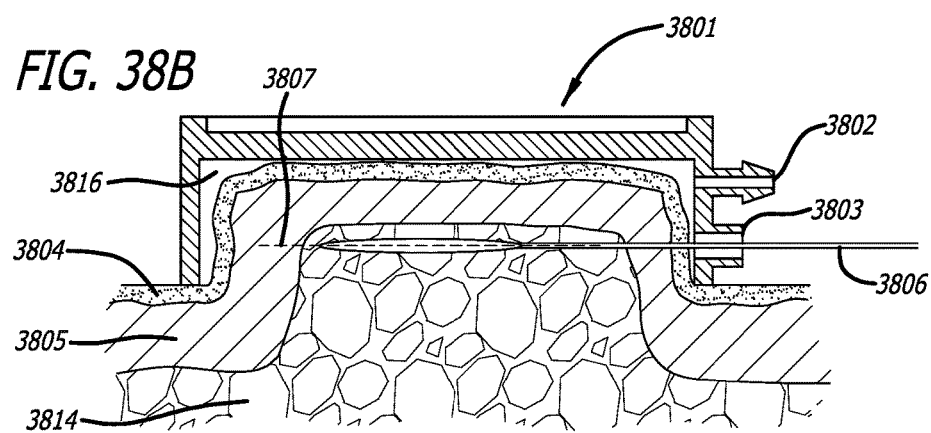

FIGS. 38A-38E further illustrate an exemplary method to create a subcutaneous tissue pocket and introduce a solid implant into the pocket. As outlined in the flow chart shown in FIG. 28D, a section of skin and subcutaneous tissue to be treated is first anesthetized. Next, as further illustrated in FIG. 38A, a handpiece 3801 with a recessed area, having a vacuum conduit 3802 and a tool conduit 3803 is placed on top of the epidermis 3804. As illustrated in FIG. 38B, a reduced air pressure is then applied through conduit 3802, pulling the epidermis 3804 and the dermis 3805 into the recessed area 3816 of the handpiece 3801. A dissection tool 3806 is then inserted through the tool conduit 3803 into subcutaneous tissue 3814 underneath the dermis 3805 and a dissection plane 3807 is created. In a subsequent step, illustrated in FIG. 38C, a tissue pocket 3808 is created or enlarged by inserting a substance introduction tool 3809. The substance introduction tool 3809 comprises a cavity 3810 and a push rod 3811. The cavity 3810 holds a solid implant 3812. In a next step, illustrated in FIG. 38D, the substance introduction tool 3809 is withdrawn in the direction of arrow 3813, while holding push rod 3811 stationary, effectively expelling implant 3812 out of the cavity 3810. The substance introduction tool is removed, the reduced air pressure released and the handpiece removed. As shown in FIG. 38E, this allows the epidermis 3804 and the dermis 3805 to relax, and form a subcutaneous tissue pocket 3808 with subcutaneous tissue 3814 around implant 3812.

Although the present invention has been described in detail with regard to the preferred embodiments and drawings thereof, it should be apparent to those of ordinary skill in the art that various adaptations and modifications of the present invention may be accomplished without departing from the spirit and the scope of the invention. Accordingly, it is to be understood that the detailed description and the accompanying drawings as set forth hereinabove are not intended to limit the breadth of the present invention.

What is claimed is:

1. A system for treating tissue, the system comprising:
   a handpiece comprising:
      a top,
      sidewalls,
      a chamber at least partially defined by the top and sidewalls,
      a tool conduit comprising an entry hole,
      a vacuum port in fluid communication with the chamber, the handpiece configured to elevate target tissue relative to surrounding tissue upon application of vacuum pressure to the chamber through the vacuum port, and
      clip recesses;
   a first tissue treatment tool comprising an injection device including:
      a needle control module,
      a needle extending from the needle control module,
      a first guide pin extending from the needle control module, and
      a supply tube extending from the needle control module, the supply tube configured to be fluidly coupled to a syringe;
   a first guidance track comprising first clips configured to be coupled to the clip recesses of the handpiece, the first guidance track comprising injection guidance tracks, the first guide pin configured to move along the injection guidance tracks to guide the needle through the entry hole and into elevated target tissue;
   a second tissue treatment tool comprising:
      a cutting blade assembly comprising a cutting blade, the cutting blade assembly configured to be coupled to a motor module configured to reciprocate the cutting blade, and
      a second guide pin extending from the cutting blade assembly; and
   a second guidance track comprising second clips configured to be coupled to the clip recesses of the handpiece, the second guidance track comprising cutting guidance tracks, the second guide pin configured to move along the cutting guidance tracks to guide the cutting blade through the entry hole and into elevated target tissue and allow movement of the cutting blade in side-to-side directions in a plane parallel to the top of the handpiece.

2. The tissue treatment system of claim 1, wherein the tool conduit of the handpiece tapers inwardly from an outside of the handpiece to the entry hole.

3. The tissue treatment system of claim 1, wherein the top of the handpiece is transparent and comprises a reference feature.

4. The tissue treatment system of claim 1, wherein the first guidance track comprises a first guide pin entry conduit configured to receive the first guide pin of the first tissue treatment tool and wherein the second guidance track comprises a second guide pin entry conduit configured to receive the second guide pin of the second tissue treatment tool.

5. A system for treating tissue, the system comprising:
   a handpiece comprising:
      a chamber,
      an entry hole,
      a port in fluid communication with the chamber, the handpiece configured to elevate target tissue relative to surrounding tissue upon application of vacuum pressure to the chamber through the port, and
      clip recesses;
   a first tissue treatment tool comprising a needle;
   a first guidance track comprising first clips configured to be coupled to the clip recesses of the handpiece, the first guidance track comprising injection guidance tracks configured to guide the needle through the entry hole and into elevated target tissue;
   a second tissue treatment tool comprising a cutting blade; and
   a second guidance track comprising second clips configured to be coupled to the clip recesses of the handpiece, the second guidance track comprising cutting guidance tracks configured to guide the cutting blade through the entry hole and into elevated target tissue and allow movement of the cutting blade in a plane parallel to the top of the handpiece.

6. The tissue treatment system of claim 5, wherein the handpiece comprises a tool conduit tapering inwardly from an outside of the handpiece to the entry hole.

7. The tissue treatment system of claim 5, wherein the handpiece comprises a transparent top comprising a reference feature.

8. The tissue treatment system of claim 5, wherein the handpiece comprises a top reversible between a first side and a second side to adjust a depth of the entry hole.

9. The tissue treatment system of claim 5, wherein the first guidance track comprises a first guide pin entry conduit configured to receive a first guide pin of the first tissue treatment tool and wherein the second guidance track comprises a second guide pin entry conduit configured to receive a second guide pin of the second tissue treatment tool.

10. A system for treating tissue, the system comprising:
   a handpiece comprising:
      a chamber, and
      an entry hole,
      the handpiece configured to elevate target tissue relative to surrounding tissue upon application of a force to the target tissue;
   a first tissue treatment tool;
   a first guidance track configured to be reversibly coupled to the handpiece, the first guidance track configured to guide the first tissue treatment tool through the entry hole and into elevated target tissue;
   a second tissue treatment tool comprising a cutting blade; and
   a second guidance track configured to be reversibly coupled to the handpiece, the second guidance track configured to guide the second tissue treatment tool through the entry hole and into elevated target tissue and allow movement of the second tissue treatment tool in a pattern different than that of the first guidance track.

11. The tissue treatment system of claim 10, wherein the handpiece comprises clip recesses, wherein the first guidance track comprises first clips configured to be coupled to the clip recesses of the handpiece, and wherein the second guidance track comprises second clips configured to be coupled to the clip recesses of the handpiece.

12. The tissue treatment system of claim 10, wherein the handpiece comprises a tool conduit tapering inwardly from an outside of the handpiece to the entry hole.

13. The tissue treatment system of claim 10, wherein the first tissue treatment tool comprises a needle, and wherein the first guidance track comprises injection guidance tracks configured to guide the needle.

14. The tissue treatment system of claim 10, wherein the second tissue treatment tool comprises a cutting blade, and wherein the second guidance track comprises cutting guidance tracks configured to guide the cutting blade.

15. The tissue treatment system of claim 14, wherein the cutting blade is deployable after insertion through the entry hole.

16. The tissue treatment system of claim 10, wherein the handpiece comprises a transparent top.

17. The tissue treatment system of claim 10, wherein the handpiece comprises a top reversible between a first side and a second side to adjust a depth of the entry hole.

18. The tissue treatment system of claim 10, wherein the handpiece comprises a port in fluid communication with the chamber and wherein the force comprises vacuum pressure.

19. The tissue treatment system of claim 10, wherein the first guidance track comprises a first guide pin entry conduit configured to receive a first guide pin of the first tissue treatment tool and wherein the second guidance track comprises a second guide pin entry conduit configured to receive a second guide pin of the second tissue treatment tool.

20. The tissue treatment system of claim 10, wherein the handpiece comprises a transparent top and a reference feature, wherein the first tissue treatment tool comprises a needle, wherein the first guidance track comprises injection guidance tracks configured to guide the needle, wherein the second tissue treatment tool comprises a cutting blade, and wherein the second guidance track comprises cutting guidance tracks configured to guide the cutting blade.

\* \* \* \* \*